US006475724B1

(12) United States Patent
Nguyen et al.

(10) Patent No.: US 6,475,724 B1
(45) Date of Patent: *Nov. 5, 2002

(54) NUCLEIC ACIDS, KITS, AND METHODS FOR THE DIAGNOSIS, PROGNOSIS AND TREATMENT OF GLAUCOMA AND RELATED DISORDERS

(75) Inventors: Thai D. Nguyen, Mill Valley, CA (US); Jon R. Polansky, Mill Valley, CA (US); Pu Chen, Villiston, VT (US); Hua Chen, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/306,828

(22) Filed: May 7, 1999

Related U.S. Application Data

(63) Continuation-in-part of application No. 09/227,881, filed on Jan. 11, 1999, which is a continuation-in-part of application No. 08/938,669, filed on Sep. 26, 1997, now Pat. No. 6,171,788, which is a continuation-in-part of application No. 08/791,154, filed on Jan. 28, 1997, now abandoned.

(51) Int. Cl.[7] .......... C12Q 1/68; C12P 19/34
(52) U.S. Cl. .......... 435/6; 435/91.1
(58) Field of Search .......... 435/6, 7.1, 69.1, 435/91.1, 325, 366, 320.1; 536/23.1, 24.1, 24.3, 24.33

(56) References Cited

U.S. PATENT DOCUMENTS

| | | | |
|---|---|---|---|
| 3,773,919 | A | 11/1973 | Boswell |
| 3,887,699 | A | 6/1975 | Yolles |
| 4,582,788 | A | 4/1986 | Knepper |
| 4,617,299 | A | 10/1986 | Knepper |
| 4,683,194 | A | 7/1987 | Saiki et al. |
| 4,683,202 | A | 7/1987 | Mullis et al. |
| 4,757,089 | A | 7/1988 | Epstein |
| 4,829,088 | A | 5/1989 | Doulakas |
| 5,075,217 | A | 12/1991 | Weber |
| 5,124,154 | A | 6/1992 | Babcock et al. |
| 5,130,238 | A | 7/1992 | Malek et al. |
| 5,169,766 | A | 12/1992 | Schuster et al. |
| 5,175,082 | A | 12/1992 | Jeffreys |
| 5,190,762 | A | 3/1993 | Yarosh |
| 5,192,535 | A | 3/1993 | Davis et al. |
| 5,270,052 | A | 12/1993 | Callahan et al. |
| 5,420,120 | A | 5/1995 | Boltralik |
| 5,474,985 | A | 12/1995 | Polansky et al. |
| 5,599,535 | A | 2/1997 | Polansky et al. |
| 5,606,043 | A | 2/1997 | Nguyen et al. |
| 5,674,888 | A | 10/1997 | Polansky et al. |
| 5,789,169 | A | 8/1998 | Nguyen et al. |
| 5,854,415 | A | 12/1998 | Nguyen et al. |
| 5,861,497 | A | 1/1999 | Nguyen et al. |
| 5,885,776 | A | 3/1999 | Stone et al. |
| 5,916,778 | A | 6/1999 | Stone |
| 5,925,748 | A | 7/1999 | Stone |
| 6,171,788 | B1 * | 1/2001 | Nguyen et al. ................ 435/6 |

FOREIGN PATENT DOCUMENTS

| | | |
|---|---|---|
| CA | 1176565 | 10/1984 |
| CA | 2216997 | 3/1999 |
| EP | 50424 | 4/1982 |
| EP | 58481 A | 8/1982 |
| EP | 84796 | 8/1983 |
| EP | 158277 A2 | 10/1985 |
| EP | 201184 | 12/1986 |
| EP | 237362 | 9/1987 |
| EP | 258017 | 3/1988 |
| EP | 0 329 822 A2 | 8/1989 |
| EP | 370719 A2 | 5/1990 |
| GB | 2135774 A | 9/1984 |
| WO | WO 88/10315 | 12/1988 |
| WO | WO 89/06700 | 7/1989 |
| WO | WO 89/06964 | 8/1989 |
| WO | WO 90/01069 | 2/1990 |
| WO | WO 90/11369 | 10/1990 |
| WO | WO 90/13668 | 11/1990 |
| WO | WO 91/05771 | 5/1991 |
| WO | WO 93/12234 | 6/1993 |
| WO | WO 94/04557 | 3/1994 |
| WO | WO 96/14411 | 5/1996 |
| WO | WO 96/33287 | 10/1996 |
| WO | WO 98/20131 | 5/1998 |
| WO | WO98/32850 | 7/1998 |
| WO | WO98/44107 | 10/1998 |
| WO | WO 99/16989 | 4/1999 |

OTHER PUBLICATIONS

Escribano et al., GenBank, Accession No. AB006686 (1995).*

Pine, et al., "Purification and cloning of interferon–stimulated gene factor 2 (ISGF2): ISGF2 (IRF–1) can bind to the promoters of both beta interferon–and interferon–stimulated genes but is not a primar transcriptional activator of either", Mol. Cell Biol. (1990) 10:2448–2457.

(List continued on next page.)

*Primary Examiner*—Andrew Wang
*Assistant Examiner*—Karen Lacourciere
(74) *Attorney, Agent, or Firm*—Arnold & Porter

(57) ABSTRACT

In a preferred aspect of the invention, the upstream sequences of the TIGR protein encoding sequence can be used to diagnose a sensivity to steroids and a risk for glaucoma or ocular hypertensive disorders. Methods, kits, and nucleic acids containing polymorphisms, base substitutions, or base additions located within the upstream region and within protein-encoding regions of the TIGR gene are also provided. The upstream sequences disclosed, including the TIGR promoter regions and those regions possessing functional characteristics associated with or possessed by the TIGR gene 5'regulatory region, can also be used to generate cells, vectors, transgenic animals, and nucleic acid constructs useful in a variety of diagnostic and prognostic methods and kits as well as therapeutic compounds, compositions, and methods.

6 Claims, 24 Drawing Sheets

OTHER PUBLICATIONS

Kubota, R et al., "*Genomic organisation of the human myocilin gene* (*MYOC*) *responsible for primary open angle glaucoma*," Biochemical and Biophysical Research Communications, US, Academic Press Inc., vol. 242, No. 242, 1998, pp. 396–400.

Anfossi, G. et al., "An Oligomer Complementary to c–myb–encoded mRNA Inhibits Proliferation of Human Myeloid Leukemia Cell Lines," Proc. Natl. Acad. Sci. (USA) 86:3379 (1989).

Amour, J.A.L. et al., "Recent Advances in Minisatellite Biology," FEBS Lett. 307:113–115 (1992).

Baldino, F. et al., "High–resolution in situ hybridization histochemistry," Methods in Enzymology, 168:761–77 (1989).

Barany, F., "Genetic Disease Detection and DNA Amplification Using Cloned Thermostable Ligase," Proc. Natl. Acad. Sci. (USA) 88:189–93 (1991).

Baumhueter et al., "A varient nuclear protein in dedifferentiated haptoma cells binds to the same functional sequences in the b fibrinogen gene bromoter as HNF–1," EMBO J., 7(8):2485–93(1988).

Beato, "Gene regulation by steroid hormones," Cell, 56:335–44 (1989).

Becker et al., "In Vivo protein—DNA interactions in a glucocorticoid response element require the presence of the hormone," Nature, 324:686–88 (1986).

Becker, D., et al., "Proliferation of human malignant melanomas is inhibited by antisense oligodeoxynucleotides targeted against basibroblast growth factor," EMBO J. 8:3685–91 (1989).

Bengtsson, B., "Incidence of manifest glaucoma," Br. J. Ophthalmol. 73:483–87 (1989).

Botstein, D. et al., "Construction of a genetic linkage man using restriction fragment length polymorphisms," Amn. J. Hum. Genet. 32:314–331 (1980).

Brent, "Mutations of the rat growth hormone promoter which invrease and decrease response to thyroid hormones define a consensus thyroid hormone response element," Molecular Endocrinology, 3:1996–2004 (1989).

Breslauer, K. et al., "Predicting DNA duplex stability from the base sequence," Proc. Natl. Acad. Sci. USA 83:3746–50 (1986).

Chen et al., "Identification of a TIGR Promoter Sequence Variant, TIGR.mt1, in a POAG Pedigree and Estimation of its Frequency in Adult POAG," Abstract #3156, Association for Research in Vision and Ophthalmology Meeting (1998).

Chen et al., "Identification of a TIGR Promoter Sequence Variatin Steroid Responders and Evidence for a Glucocorticoid–induced DNA Binding Protein of the TIGR Gene in TM Cells" Abstract #2666, Association for Research in Vision and Ophthalmology Meeting (1999).

Chen, P, "Expression of Trabecular Meshwork Inducible Glucocorticoid Response (TIGR) peptide in SF9 Cells," Invest. Opthal. Vis. Sci. 34(4) 1385 Abstract (1993).

Chodosh et al., "Human CCAAT–Binding Proteins have heterologous subunits," Cell, 53:11–24 (1988).

Clark, A.F., "Evaluation of anti–glaucoma compounds and discovery of pathogenic mechanisms using perfusion cultured human eyes" Exper. Eye Res. 55:265 Abstract (1992).

Claverie et al, "Alu Alert," Nature 371: 751–52 (1994).

Coles et al., "An H1 histone gene–specific 5' element and evolution of H1 and H5 genes," Nucleic Acids Research, 13:585–94 (1985).

Comb et al., "CpG methylation inhibits proenkephalin gene expression and binding of the transcription factor AP–2," Nucleic Acids Research, 18:3975–82 (1990).

Courtois et al., "Nuclear factor–1 and activator protein–2 bind in a mutually exclusive way to overlapping promoter sequences and trans–activate the human growth hormone gene," Nucleic Acids Research, 18:57–64 (1990).

deVemeuil et al., "The lack of transcriptional activation of the v–erb A oncogene is in part due to a mutation present in the DNA binding domain of the protein," Nucleic Acids Research, 18:4489–97 (1990).

deWet et al., "Firefly luciferase gene: structure and expression in mammalian cells," Molecular and Cellular Biology, 7:725–37 (1987).

Escribano, J. et al., "Isolation and Characterization of Cell–Specific cDNA Clones from a Subtractive Library of the Ocular Cileary Body of a Single Normal Human Donor: Transcription and Synthesis of Plasma Proteins" J. Biochem. 118(5):921–31 (1995).

Evans, "The steroid and thyroid homone receptor superfamily," Science, 240:889–895 (1988).

Faisst et al., "Compilation of vertebrate–encoded transcription factors," Nucleic Acids Research, 20:3–26 (1992).

Fauss, D., "Comparisons of glucocorticoid (GC) effects and oxidative stress on protein/glycoprotein synthesis in cultured human lens epithelium (HLE) vs. human trabecular meshwork (HTM) cells" Invest. Ophthamol. Vis. Science 31(4) 432 Abstract (1990).

Forman et al., "Interactions among a subfamily of nuclear hormone receptors: the regulatory zipper model," Molecular Endocrinology, 4:1293–1301 (1990).

Frazer et al., "A radiation hybrid map of the region on huyman chromosome 22 containing the neurofibrosmatosis type 2 locus," Genomics 14(3):574–78 (1992).

Freier, S.M. et al., "Improved free–energy parameters for predictions of RNA duplex stability," Proc. Natl. Acad. Sci. (USA) 83:9373–9377 (1986).

Frohman, M.A. et al., "Rapid production of full–length cDNAs from rare transcripts: Amplification using a single gene–specific oligonucleotide primer," Proc. Natl. Acad. Sci. (USA) 85:8998–9002 (1988).

Gaub et al., "Activation of the ovalbumin gene by the estrogen receptor involves the fos–jun complex," Cell, 63:1267–76 (1990).

Gerwitz, A.M. et al., "A c–myb antisense oligodeoxynucleotide inhibits normal human hematopoiesis in vitro," Science 242:1303 (1988).

Gewitz et al., "Facilitating oligonucleotide delivery: helping antisense deliver on its promise," Proc. Natl. Acad. Sci. (USA) 93:3161–63 (1996).

Glass et al., "The thyroid hormone receptor binds with opposite transcriptional effects to a common sequence motif in thyroid hormone and estrogen response elements," Cell, 54:313–23 (1988).

Goodchild et al., "Inhibition of human immunodeficiency virus replication by antisense oligodeoxynucleotides," Proc. Natl. Acad. Sci. (USA) 85:5507 (1988).

Gounari et al., "Amino–terminal domain of NF1 binds as a dimer and activates adenovirus DNA replication," EMBO J. 10:559–66 (1990).

Goyal et al., "Analysis of multiple forms of nuclear factor I in human and murine cell lines," Molecular and cellular biology, 10:1041–48 (1990).

Gray, I.C. et al., "Evolutionary transience of hypervariable minisatellites in man and the primates," Proc. R. Acad. Soc. Lond. 243:241–53 (1991).

Greve, M. et al., "Comparison of the oculokinetic perimetry glaucoma screener with two types of visual field analyser," Can. J. Ophthamol. 28:201–06 (1993).

Gronostajski et al., "Site-specific DNA binding of nuclear factor I: Analyses of cellular binding sites," Molecular and Cellular Biology, 5:964–71 (1985).

Gusella, J.F., "DNA polymorphism and human disease," Ann. Rev. Biochem. 55:831–854 (1986).

Gutman et al., "The collagenase gene promoter contains a TPA and oncogene-responsive unit encompassing the PEA3 and AP-1 binding sites," EMBO J. 9(7): 2241–46 (1990).

Harada et al., "Absence of the Type 1 IFN system in EC cells: transcriptional activator (IRF-1) and repressor (IRF-2) genes are developmentally regulated," Cell 63:303–12 (1990).

Hecht et al., "A progesterone responsive element maps to the far upstream steroid dependent Dnase hypersensitive site of chicken iysozyme chromath," EMBO J. 7:2063–73 (1988).

Henninghausen et al., "Nuclaer factor 1 interacts with five DNA elements in the promoter region of the human cytomegalovirus major immediate early gene," EMBO J., 5:1367–71 (1986).

Hillel, J. et al., "DNA fingerprints applied to gene introgression breeding programs," Genet. 124:783–89 (1990).

Hillel, J. et al., "DNA fingerprints of poultry," Anim. Genet. 20:145–55 (1989).

Hitchings, R.A., "Glaucoma Screening," Br. J. Ophthamol. 77:326 (1993).

Holt, J.T. et al, "An oligomer complementary to c-myc mRNA inhibits proliferation of HL-60 promyelocytic cells and induces differentiation," Molec. Cell. Biol. 8:963 (1988).

Imam et al., "Transcription factors induced by interferons a and g," Nucleic Acids Research, 18:6573–80 (1990).

Ioannou et al., "A new bacteriophage P1-derived vector for the propagation of large human DNA fragments," Nature Genetics, 6:84–89 (1994).

Jefferson et al., "GUS fusions: b-glucuronidase as a sensitive and versatile gene fusion marker in higher plants," EMBO J. 6:3901–07 (1987).

Jeffreys, A.J. et al., "DNA 'fingerprints' and segregation analysis of multiple markers in human pedigrees," Amer. J. Hum. Genet. 39:11–24 (1986).

Jeffreys, A.J. et al., "DNA fingerprints of dogs and cats," Anim. Genet. 18:1–15 (1987).

Jeffreys, A.J. et al., "Individual-specific 'fingerprints' of human DNA," Nature 316:76–79 (1985).

Jones et al., "Trans-acting protein factors and the regulation of eukaryotic transcription: lessons from studies on DNA tumor viruses," Genes and Development, 2:267–81 (1988).

Jones, L. et al., "Identical twin marrow transplantation for 5 patients with chronic myeloid leukaemia: Role of DNA finger printing to confirm monozygosity in 3 cases," Eur. J. Haematol. 39:144–47 (1987).

Jurka et al. "Reconstruction and analysis of human alu genes," J. Mol. Evolution 32: 105–121 (1991).

Kern et al., "Identification of p53 as a Sequence-specific DNA-binding protein," Science 252: 1708–1711 (1991).

Kim et al., "Autoinduction of transforming growth factor b1 is mediated by the AP-1 complex," Molecular and Cellular Biology, 10:1492–97 (1990).

Kitazawa et al., "The prognosis of corticosteroid-responsive individuals" Arch. Ophthalmol. 99:819–23 (1981).

Klemitti, A., "The dexamethason provocative test: a predictive tool for glaucoma?" Acta Ophthamol. 68:29–33 (1990).

Korner, J.S. et al., "Mutation detection using nucleotide analogs that alter electrophoretic mobility," Nucl. Acids. Res. 17:7779–7784 (1989).

Kuppuswamy, M.N. et al., "Single nucleotide primer extension to detect genetic diseases: experimental application to hemophilia B (Factor IX) and cystic fibrosis genes," Proc. Natl. Acad. Sci. (USA) 88:1143–47 (1991).

Kwoh, D.Y. et al., "Transcription-based amplification system and detection of amplified human immunodeficiency virus type 1 with a bead-based sandwich hyubridization format," Proc. Natl. Acad. Sci. (USA), 86:1173–77 (1989).

Landegren, U. et al., "A ligase-mediated gene detection technique," Science 241:1077–80 (1988).

Langer, R. et al., "Controlled release of macromolecules," Chem. Tech. 12:98 (1982).

Lathe R., "Synthetic oligonucleotide probes deduced from amino acid sequence data—theoretical and practical considerations," Journal of Molecular Biology, 183:1–12 (1985).

Lee et al., "Mutational analysis by a combined application of the multiple restriction fragment-sibngle strand conformation polymorphism and the direct linear amplification DNA sequencing protocols," Analytical Biochemistry, 205:289–93 (1992).

Lenardo et al., "NF-kB: A pleiotropic mediator of inducible and tissue-specific gene control," Cell 58:227–29 (1989).

Lenardo et al., "Protein-binding sites in Ig gene enhancers determine transcriptional activity and inducibility," Science 236:1573–77 (1987).

Lewis et al., "Intraocular pressure response to topical dexamethasone as a predictor for the development of primary open angle glaucoma" Am. J. Ophthamol. 106:607–12 (1988).

Liberman et al., "Involvement of a second lymphoid-specific enhancer element in the regulation of immunoglobulin heavy-chain gene expression," Molecular and Cellular Biology, 10:3155–62 (1990).

Linderson et al., "NFE, A new transcriptional activator that facilitates p50 and c-red-dependent IgH 3' enhancer activity," European J. Immunology 27: 468–475 (1997).

Lo et al., "Analysis of complex genetic systems by ARMS-SSCP: application to HLA genotyping," Nucleic Acids Research, 29:1005–09 (1992).

Martin et al., "Activation of the polyomavirus enhancer by a murine activator protein 1 (AP1) homolog and two contiguous proteins," Proc. Natl. Acad. Sci. (USA), 85:5839–43 (1988).

Mermod et al., "Enhancer binding factors AP-4 and AP-1 act in concert to activate SV40 late transcription in vitro," Nature, 332:557–61 (1988).

Mitchell, et al., "Transcription factor AP-2 is expressed in neural crest cell lineages during mounse embryogenesis," Genes and Development, 5:105–19 (1991).

Moore, S.S. et al., "The conservation of dinucleotide microsatellites among mammalian genomes allow the use of heterologous PCR primer pairs in closely related species," Genomics 10:654–660 (1991).

Mullis, K. et al., "Specific enzymatic amplification of DNA in vitro: the polymerase chain reaction," Cold Spring Harbor Symp. Quant. Biol. 51:263–73 (1986).

Murnane et al., "Use of a mammalian interspersed repetitive (MIR) element in the coding and processing sequences of mammalian genes," Nucleic Acids Research 15:2837–39 (1995).
Muscat et al., "A common factor regulates skeletal and cardiac a–Actin gene transcription in muscle," Molecular and Cellular Biology 10:4120–33 (1988).
Nguyen et al., "A TIGR (or MYOC, GLC1A) Gene Promoter Polymorphism Associates with Steroid–Glaucoma and Evidence for its Tissue Specific Expression in the Human Trabecular Meshwork Cells" Abstract #422, American Society of Human Genetics Meeting (1999).
Nguyen et al., "Cloning of glucocorticoid–induced proteins in HTM cells: vertification of progressive, high dose dependent, cDNAs to correlate with effects on IOP," Invest. Ophthalmol. Vis. Sci. 31:505 Abstract (1990).
Nguyen et al., "Gene structure and properties of TIGR, an olfactomedin–related glycoprotein cloned from glucocorticoid–induced trabecular meshwork cells" J. Biol. Chem. 273:6341–50 (1998).
Nguyen et al., "Mutation Anayses of the TIGR (Trabecular Meshwork Inducible Glucocorticoid Response) Promoter in a POAG Pedigree" Abstract #1999, American Society of Human Genetics Meeting (1997).
Nguyen, T.D. et al., "Glucocorticoid (GC) effects on HTM cells: molecular biology approaches," In: "Schriftenreihe de academie der wissenschaften und der diteratur mainz," 331–43 (1993).
Nguyen, T.D. et al., "Molecular Biology Studies of Steroid–Induced glaucoma model using cultured human trabecular meshwork," Invest. Ophthalmol. Vis. Sci. 32:789 Abstract (1991).
Nickerson, D.A. et al., "Automated DNA diganostics using an ELISA–based oligonucleotide ligation assay," Proc. Natl. Acad. Sci. (USA) 87:8923–27 (1990).
Nyren, P. et al., "Solid phase DNA minisequencing by an enzymatic luminometric inorganic pyrophosphate detection assay," Anal. Biochem. 208:171–175 (1993).
Ohara, O. et al., "One–sided polymerase chain reaction: the amplification of cDNA," Proc. Natl. Acad. Sci. (USA) 86:5673–77 (1989).
Orita et al., "Rapid and sensitive detection of point mutations and DNA polymorphisms using the polymerase chain reaction," Genomics, 5:874–79 (1989).
Ortego, J., "Cloning and characterization of subtracted cDNAs from a human ciliary body library encoding TIGR, a protein involved in juvenile open angle glaucoma with homology to ayosin and olfactomedin" FEBS Letters 413:349–53 (1997).
Partidge et al., "Dexamethasone induces specific proteins in human trabecular meshwork cells," Invest. Ophthalmol. Visual Sci. 30(8):1843–47 (1989).
Polansky, J.R. et al., "Cellular pharmacology and molecular biology of the trabecular meshwork inducible glucocorticoid response gene product," Ophthalmologica 211:126–139 (1997).
Polansky, J.R. et al., "Eicosanoid production and glucocorticoid regulatory mechanisms in cultured human trabecular meshwork cells," Prog. Clin. Biol. Res. 312:113–138 (1989).
Polansky, J.R. et al., "Glucocorticoid receptors and steroid glaucoma mechanisms," Encounters in Glaucoma Research 1: Receptor Biology and Glaucoma, Fogliazza Editore, Milan pp. 273–299 (1994).
Polansky, J.R. et al., "Growth factor effects and modulation of gluvovorticoid (GC) and other stress responses in human trabecular meshwork (HTM) cells," Exp. Eye Research 55:265 Abstract (1992).
Polansky, J.R. et al., "In vitro correlates of glucocorticoid effects on intraocular pressure," In: Glaucoma Update IV, Springer–Verlag, Berlin, pp. 20–29 (1991).
Polansky, J.R. et al., "Studies on Human trabecular cells propagated In Vitro," Vision Research 21:155–60 (1981).
Polansky, J.R., "HTM cell culture model for steroid effects on intraocular pressure: overview" In: "Schriftenreihe de academie der wissenschaften und der diteratur mainz," 307–18 (1993).
Polansky, J.R., "Side effects of topical ophthalmic therapy with anti–inflammatory steroids and b–blockers," Current Opinion in Ophthalmology 3:259–72 (1992).
Polansky, J.R., et al., "Cellular mechanisms influencing the aqueous outflow pathway," In: Principles and practice of ophthalmology, Albert, D.M. et al., Eds., B. Saunders & Co. Philadelphia, pp. 226–251 (1994).
Polansky, J.R., et al., "Human trabecular meshwork inducible glucocorticoid response protein mRNA" Abstract (1997).
Prezant et al., "Trapped Oligonucleotide Nulceotide Incorporation (TONI) assay, a simple method for screening point mutations," Hum. Mutat. 1:159–64 (1992).
Rajnarayan et al., "Reconstitution of Protein Kinase a regulation of the rat prolactin promotor in HeLa nonpituitary cells: identification of both GHF–1/Pit–1–dependent and –independent mechanisms," Molecular Endochronology 4:502–12 (1995).
Redondo et al., "A T cell–specific transcriptional enhancer within the human T cell receptor & locus," Science, 247:1225–28 (1990).
Regec et al., "The cloning and characterization of the human transcobalamin II gene," Blook 85:2711–2719 (1995).
Resnick et al., "Platelet–derived growth factor B chain promotor contains a cis–acting fluid shear–stress–responsive element," Proc. Natl. Acad. Sci. (USA) 80:4591–95 (1993).
Richard et al., "A radiation hybrid map of the distal short arm of human chromosome 11, containing the Beckwith–Weidemann and associated embryonal tomor disease loci," American Journal of Human Genetics 52(5):915–21 (1993).
Richards et al., "Mapping of a gene for autosomal dominant juvenile–onset open–angle glaucoma to chromosome 1q," Am. J. Hum. Genet. 51(1): 62–70 (1994).
Rojanasakul, "Antisense oligonucleotide therapeutics: drug delivery and targeting," Advanced Drug Delivery Reviews 18:115–31 (1996).
Rossi et al., "A nuclear factor 1 binding site mediates the transcriptional activation of a type 1 collagen promoter by transforming growth factor–b," Cell, 52:405–14 (1988).
Rychlik, W. et al., "A computer program for choosing optimal oligonucleotides for filter hybridization, sequencing and in vitro amplification of DNA," Nucleic Acids Research, 17:8543–51 (1989).
Sakai et al., "Hormone–mediated repression: a negative glucocorticoid response element from the bovine prolactin gene," Genes & Development, 2:1144–54 (1988).
Sambrook et al., In: "Molecular cloning, laboratory manual, 2nd edition" Cold Spring Harbor Press, Cold Spring Harbor, NY (1989).
Sarfarazi, "Recent advances in molecular genetics of glaucomas," Human Molecular Genetics 6:1667–77 (1997).

Sarkar, et al., "Dideoxy fingerprinting (ddF): A rapid and efficient screen for the presence of mutations," Genomics, 13:441–43 (1992).

Schildkraut, C. et al., "Dependence of the Melting Temperature of DNA on salt concentration," Biopolymers, 3:195–208 (1965).

Shirayoshi et al., "Interferon–induced transcription of a major histocompatibility class I gene accompanies binding of inducible nuclear factors to the interferon consensus sequence," Proc. Natl. Acad. Sci. (USA) 85:5884–88 (1988).

Shore et al., "Identification of silencer binding proteins from yeast: possible roles in SIR control and DNA replication," EMBO J., 6:461–67 (1987).

Sidman et al., "Controlled release of macromolecules and pharmaceuticals from synthetic polypeptides based on glutamic acid," Biopolymers 22:547 (1983).

Snyder et al., "Olfactomedin: purification, characterization, and localization of a novel olfactory glycoprotein," Biochemistry 30:9143–53 (1991).

Stanojevic et al., "Regulation of a segmentation struipe by overlapping activators and repressors in the drosophila embryo," Science, 254:1385–87 (1991).

Stone, E.M. et al., "Identification of a Gene that Causes Primary Open Angle Glaucoma," Science 275(31):668–70 (1997).

Sunden, S.L.F. et al., "Fine Mapping of the Autosomal Dominant Juvenile Open Angle Glaucoma (GLC1A) Region and Evaluation of Candidate Genes" Genome Research 6(9):862–69 (1996).

Suzuki et al., "Allele–specific polymerase chain reaction: a method for amplification and sequence determination of a single component among a mixture of sequence variants," Analytical Biochemistry, 192:82–84 (1991).

Syvanen, A.C. et al., "A primer–guided nucleotide incorporation assay in the genotyping of apolipoprotein E," Genomics 8:684–92 (1990).

Taniguchi et al., "Interaction site of *Escherichia coli* cyclic AMP receptor protein on DNA of galactose operon promoters," Poc. Natl. Acad. Sci. (USA) 76:5090–94 (1979).

Tuck, M.W. et al., "Relative effectiveness of different modes of glaucoma screening in optometric practive," Ophthal. Physiol. Opt. 13:227–232 (1993).

Ugozzoli, L. et al., "Detection of specific alleles by using allele specific primer extension followed by capture on solid support," GATA 9:107–12 (1992).

Vaughan, D. et al., "Glaucoma" In: General Ophthalmology, Appleton & Lange, Norwalk, CT, pp. 213–230 (1992).

Vernon, S.A., "Intra–eye pressure range and pulse profiles in normals with the pulsair non–contact tonometer," Eye 7:134–37 (1993).

Von der Ahe et al., "Glucocorticoid and progesterone receptors bind to the same sites in two hormonally regulated promoters," Nature 313:706–09 (1985).

Vriz et al., "The sry protein, like HMG 1, recognizes (CA)n sequences, an abundant repeat sequence in vertebrates," Biochemistry and Molecular Biology International 37:1137–46 (1995).

Walker, G.T. et al., "Isothermal in vitro amplification of DNA by a restriction enzyme/DNA polymerase system" Proc. Natl. Acad. Sci. (USA) 89:392–96 (1992).

Weinreb, R.N. et al., "Detection of glucocorticoid receptors in cultured human trabecular cells," Invest. Ophthalmol. Vis. Sci. 21:403–407 (1981).

West et al., "Interaction of a tissue–specific factor with an essential rat growth hormone gene promoter element," Molecular and Cellular Biology, 7:1193–97 (1987).

Wickstrom et al., "Human Promyelocytic Leukemia HL–60 cell proliferation and c–myc protein expression are inhibited by an antisense pentadecadeoxynucleotide targeted against c–myc mRNA," Proc. Natl. Acad. Sci. (USA) 85:1028 (1988).

Williams et al., "Analysis of the DNA–binding and activation properties of the human transcription factor AP–2," Genes and Development, 5:670–82 (1991).

Winning et al., "Developmental regulation of transcription factor AP–2 during xenopus laevis embryogenesis," Nucleic Acids Research, 19:3709–14 (1991).

Wu, D.Y. et al., "The ligation amplification reaction (LAR)—amplification of specific DNA sequences using sequential rounds of template–dependent ligation," Genomics 4:560 (1989).

Yokoe, et al., "Molecular cloning of olfactomedin, an extracellular matrix protein specific to olfactory neuroepithelium," Proc. Natl. Acad. Sci. 90:4655–59 (1993).

Yu–Lee et al., "Interferon–regulatory factor 1 is an immediate–early gene under transcriptional regulation by prolactin in Nb2 T cells," Molecular and Cellular Biology, 10:3087–94 (1990).

Yun, A.J., et al., "Proteins secreted by human trabecular cells," Invest. Ophthalmol. Vis. Sci. 30:2012–22 (1989).

Zhan, G.L. et al., "Steroid glaucoma: cortiocosteroid–induced ocular hypertension in cats," Exper. Eye Res. 54:211–218 (1992).

Nguyen et al., "Molecular Biology and Genetic Studies of the Major Extracellular Glucocorticoid(GC)–Induced Glycoprotein Cloned from the Human Trabecular Meshwork (HTM) Cells," Abstract, ARVO meeting, (1997).

* cited by examiner

```
1                                ATC TTTGTTCAGT TTACCTCAGG GCTATTATGA  33

34 AATGAAATGA GATAACCAAT GTGAAAGTCC TATAAACTGT ATAGCCTCCA TTCGGATGTA  93

94 TGTCTTTGGC AGGATGATAA AGAATCAGGA AGAAGGAGTA TCCACGTTAG CCAAGTGTCC  153

154 AGGCTGTGTC TGCTCTTATT TTAGTGACAG ATGTTGCTCC TGACAGAAGC TATTCTTCAG 213

214 GAAACATCAC ATCCAATATG GTAAATCCAT CAAACAGGAG CTAAGAAACA GGAATGAGAT 273

274 GGGCACTTGC CCAAGGAAAA ATGCCAGGAG AGCAAATAAT GATGAAAAAT AAACTTTTCC 333

334 CTTTGTTTTT AATTTCAGGA AAAAATGATG AGGACCAAAA TCAATGAATA AGGAAAACAG 393
                                 (Prl.FPIII) CCTG AAAATGAATA AGAAA

394 CTCAGAAAAA AGATGTTTCC AAATTGGTAA TTAAGTATTT GTTCCTTGGG AAGAGACCTC 453
                                  (PR/GR-MMTV) T GTTCTTTTGG AA
                                                    (SSRE)  GAGACC

454 CATGTGAGCT TGATGGGAAA ATGGGAAAAA CGTCAAAAGC ATGATCTGAT CAGATCCCAA 513

514 AGTGGATTAT TATTTTAAAA ACCAGATGGC ATCACTCTGG GGAGGCAAGT TCAGGAAGGT 573

574 CATGTTAGCA AAGGACATAA CAATAACAGC AAAATCAAAA TTCCGCAAAT GCAGGAGGAA 633
    CCTTTTAG-A AAGGACAAAA CAGAATG (nGRE-PRL)

634 AATGGGGACT GGGAAAGCTT TCATAACAGT GATTAGGCAG TTGACCATGT TCGCAACACC 693

694 TCCCCGTCTA TACCAGGGAA CACAAAAATT GACTGGGCTA AGCCTGGACT TTCAAGGGAA 753
                                               GCCTGGACT GTC (CBE-P53)

754 ATATGAAAAA CTGAGAGCAA AACAAAAGAC ATGGTTAAAA GGCAACCAGA ACATTGTGAG 813
                          ATTTTTCTGA TTGGTTAAAA GT (NFEi)

814 CCTTCAAAGC AGCAGTGCCC CTCAGCAGGG ACCCTGAGGC ATTTGCCTTT AGGAAGGCCA 873
                                   G ACCCTGAGGC T (KTF.1-CS)

874 GTTTTCTTAA GGAATCTTAA GAAACTCTTG AAAGATCATG AATTTTAACC ATTTTAAGTA 933

934 TAAAACAAAT ATGCGATGCA TAATCAGTTT AGACATGGGT CCCAATTTTA TAAAGTCAGG 993
                                             (PRE-lysozyme) AGGCCGT

994 CATACAAGGA TAACGTGTCC CAGCTCCGGA TAGGTCAGAA ATCATTAGAA ATCACTGTGT 1053
    GATCCAAGGA GCAGAAGTTC CAGCTATGGT CAG      (GRE-hMT) GG TACACTGTGT

1054 CCCCATCCTA ACTTTTTCAG AATGATCTGT CATAGCCCTC ACACACAGGC CCGATGTGTC 1113
CCT

1114 TGACCTACAA CCACATCTAC AACCCAAGTG CCTCAACCAT TGTTAACGTG TCATCTCAGT 1173
```

FIG.1A

```
1174 AGGTCCCATT ACAAATGCCA CCTCCCCTGT GCAGCCCATC CCGCTCCACA GGAAGTCTCC 1233

1234 CCACTCTAGA CTTCTGCATC ACGATGTTAC AGCCAGAAGC TCCGTGAGGG TGAGGGTCTG 1293
                                                     (SSRE) GGTCTC

1294 TGTCTTACAC CTACCTGTAT GCTCTACACC TGAGCTCACT GCAACCTCTG CCTCCCAGGT 1353

1354 TCAAGCAATT CTCCTGTCTC AGCCTCCCGC GTAGCTGGGA CTACAGGCGC ACGCCCGGCT 1413
                        C AGCCCCCCGC GCAGC (ETF.EGFR)

1414 AATTTTTGTA TTGTTAGTAG AGATGGGGTT TCACCATATT AGCCCGGCTG GTCTTGAACT 1473
        Alu Repeat Region                CCATATT AGG (SRE-cFos)

1474 CCTGACCTCA GGTGATCCAC CCACCTCAGC CTCCTAAAGT GCTGGGATTA CAGGCATGAG 1533

1534 TCACCGCGCC CGGCCAAGGG TCAGTGTTTA ATAAGGAATA ACTTGAATGG TTTACTAAAC 1593

1594 CAACAGGGAA ACAGACAAAA GCTGTGATAA TTTCAGGGAT TCTTGGGATG GGGAATGGTG 1653

1654 CCATGAGCTG CCTGCCTAGT CCCAGACCAC TGGTCCTCAT CACTTTCTTC CCTCATCCTC 1713

1714 ATTTTCAGGC TAAGTTACCA TTTTATTCAC CATGCTTTTG TGGTAAGCCT CCACATCGTT 1773

1774 ACTGAAATAA GAGTATACAT AAACTAGTTC CATTTGGGGC CATCTGTGTG TGTGTATAGG 1833
              GTTTACAT AAAC (VBP-vitel)                              GG

1834 GGAGGAGGGC ATACCCCAGA GACTCCTTGA AGCCCCCGGC AGAGGTTTCC TCTCCAGCTG 1893
     GGAKGAGG (MalT-CS)

1894 GGGGAGCCCT GCAAGCACCC GGGGTCCTGG GTGTCCTGAG CAACCTGCCA GCCCGTGCCA 1953

1954 CTGGTTGTTT TGTTATCACT CTCTAGGGAC CTGTTGCTTT CTATTTCTGT GTGACTCGTT 2013

2014 CATTCATCCA GGCATTCATT GACAATTTAT TGAGTACTTA TATCTGCCAG ACACCAGAGA 2073

2074 CAAAATGGTG AGCAAAGCAG TCACTGCCCT ACCTTCGTGG AGGTGACAGT TTCTCATGGA 2133

2134 AGACGTGCAG AAGAAAATTA ATAGCCAGCC AACTTAAACC CAGTGCTGAA AGAAAGGAAA 2193
                                      GCGTGAC CGGAGCTGAA AGAAAGGAAC

2194 TAAACACCAT CTTGAAGAAT TGTGCGCAGC ATCCCTTAAC AAGGCCACCT CCCTAGCGCC 2253
     AC (ERE-c.vitel)

2254 CCCTGCTGCC TCCATCGTGC CCGGAGGCCC CCAAGCCCGA GTCTTCCAAG CCTCCTCCTC 2313

2314 CATCAGTCAC AGCGCTGCAG CTGGCCTGCC TCGCTTCCcG TGAATCGTCC TGGTGCATCT 2373
                     AGCAG CTGGC (NF-mutagen)

2374 GAGCTGGAGA CTCCTTGGCT CCAGGCTCCA GAAAGGAAAT GGAGAGGGAA ACTAGTCTAA 2433
                                    A GAAAGGGAAA GGA (PRF-myc)

2434 CGGAGAATCT GGAGGGGACA GTGTTTCCTC AGAGGGAAAG GGGCCTCCAC GTCCAGGAGA 2493
                ACCCGGTACA CTGTGTCCTC CCGCT (GRE-hMT.IIa)
             CC CTTTGGGCCA ATGTGTCCTG AGGGGA (GRE-hGH)
```

FIG. 1B

```
2494 ATTCCAGGAG GTGGGGACTG CAGGGAGTGG GGACGCTGGG GCTGAGCGGG TGCTGAAAGG 2553
                                CTGG GGAGCCTGGG GA (AP.2-SV40)

2554 CAGGAAGGTG AAAAGGGCAA GGCTGAAGCT GCCCAGATGT TCAGTGTTGT TCACGGGGCT 2613

2614 GGGAGTTTTC CGTTGCTTCC TGTGAGCCTT TTTATCTTTT CTCTGCTTGG AGGAGAAGAA 2673
             CT CGTTGCTTCG AG (HSTF-hsp70)

2674 GTCTATTTCA TGAAGGGATG CAGTTTCATA AAGTCAGCTG TTAAAATTCC AGGGTGTGCA 2733
                                                                   A

2734 TGGGTTTTCC TTCACGAAGG CCTTTATTTA ATGGGAATAT AGGAAGCGAG CTCATTTCCT 2793
     TGGGTTTTTG (SBF.yeast)

2794 AGGCCGTTAA TTCACGGAAG AAGTGACTGG AGTCTTTTCT TTCATGTCTT CTGGGCAACT 2853

2854 ACTCAGCCCT GTGGTGGACT TGGCTTATGC AAGACGGTCG AAAACCTTGG AATCAGGAGA 2913

2914 CTCGGTTTTC TTTCTGGTTC TGCCATTGGT TGGCTGTGCG ACCGTGGGCA AGTGTCTCTC 2973
              C TTTCTGGTTT TGCAG (NF.1-bithorax)
                (NF-MHCII/)CCATTGGT T

2974 CTTCCCTGGG CCATAGTCTT CTCTGCTATA AAGACCCTTG CAGCTCTCGT GTTCTGTGAA 3033

3034 CACTTCCCTG TGATTCTCTG TGAGGGGGGA TGTTGAGAGG GGAAGGAGGC AGAGCTGGAG 3093

3094 CAGCTGAGCC ACAGGGGAGG TGGAGGGGGA CAGGAAGGCA GGCAGAAGCT GGGTGCTCCA 3153

3154 TCAGTCCTCA CTGATCACGT CAGACTCCAG GACCGAGAGC CACAATGCTT CAGGAAAGCT 2943

2944 CAATGAACCC AACAGCCACA TTTTCCTTCC CTAAGCATAG ACAATGGCAT TTGCCAATAA 3273

3274 CCAAAAAGAA TGCAGAGACT AACTGGTGGT AGCTTTTGCC TGGCATTCAA AAACTGGGCC 3333
                GAAGTGACT AACTG (PEA.1-Polyoma)

3334 AGAGCAAGTG GAAAATGCCA GAGATTGTTA AACTTTTCAC CCTGACCAGC ACCCCACGCA 3393

3394 GCTCAGCAGT GACTGCTGAC AGCACGGAGT GACCTGCAGC GCAGGGGAGG AGAAGAAAAA 3453
                         C AGGTCAGAGT GACCTG (ERE.2-Vitel.)

3454 GAGAGGGATA GTGTATGAGC AAGAAAGACA GATTCATTCA AGGGCAGTGG GAATTGACCA 3513

3514 CAGGGATTAT AGTCCACGTG ATCCTGGGTT CTAGGAGGCA GGGCTATATT GTGGGGGGAA 3573
                (GRE-FLV) CGGGATAC CGAGAGAACA GGGCTATAGG

3574 AAAATCAGTT CAAGGGAAGT CGGGAGACCT GATTTCTAAT ACTATATTTT TCCTTTACAA 3633
                              GAGACC (SSRE)

3634 GCTGAGTAAT TCTGAGCAAG TCACAAGGTA GTAACTGAGG CTGTAAGATT ACTTAGTTTC 3693
                                        (ICS-MTII/ HLA-DR/)AGTTTC

3694 TCCTTATTAG GAACTCTTTT TCTCTGTGGA GTTAGCAGCA CAAGGGCAAT CCCGTTTCTT 3753
     TCCTCT

3754 TTAACAGGAA GAAAACATTC CTAAGAGTAA AGCCAAACAG ATTCAAGCCT AGGTCTTGCT 3813

3814 GACTATATGA TTGGTTTTTT GAAAAATCAT TTCAGCGATG TTTACTATCT GATTCAGAAA 3873
```

FIG.1C

```
3874 ATGAGACTAG TACCCTTTGG TCAGCTGTAA ACAAACACCC ATTTGTAAAT GTCTCAAGTT 3933
                          GG TCA (1/2 ERE)

3934 CAGGCTTAAC TGCAGAACCA ATCAAATAAG AATAGAATCT TTAGAGCAAA CTGTGTTTCT 3993

3994 CCACTCTGGA GGTGAGTCTG CCAGGGCAGT TTGGAAATAT TTACTTCACA AGTATTGACA 4053

4054 CTGTTGTTGG TATTAACAAC ATAAAGTTGC TCAAAGGCAA TCATTATTTC AAGTGGCTTA 4113

4114 AAGTTACTTC TGACAGTTTT GGTATATTTA TTGGCTATTG CCATTTGCTT TTTGTTTTTT 4173
                             (NF.1-HCMV)TTGGCTATTG GCCA             CTTT

4174 CTCTTTGGGT TTATTAATGT AAAGCAGGGA TTATTAACCT ACAGTCCAGA AAGCCTGTGA 4233
     CTCTTT (ISGF2)

4234 ATTTGAATGA GGAAAAAATT ACATTTTTGT TTTTACCACC TTCTAACTAA ATTTAACATT 4293
                                              (Zn binding)---------

4294 TTATTCCATT GCGAATAGAG CCATAAACTC AAAGTGGTAA TAACAGTACC TGTGATTTTG 4353

4354 TCATTACCAA TAGAAATCAC AGACATTTTA TACTATATTA CAGTTGTTGC AGATACGTTG 4413
                    (CAP-gal0) ATTTA TTCCATGTCA CACTTTTCGC A

4414 TAAGTGAAAT ATTTATACTC AAAACTACTT TGAAATTAGA CCTCCTGCTG GATCTTGTTT 4473
                    TTACTC A (AP-1)

4474 TTAACATATT AATAAAACAT GTTTAAAATT TTGATATTTT GATAATCATA TTTCATTATC 4533
                          GAT GTTTAAAAT (PRL-FPII)

4534 ATTTGTTTCC TTTGTAATCT ATATTTTATA TATTTGAAAA CATCTTTCTG AGAAGAGTTC 4593
                                   (GRE-MuRFV) TGTTTTTCTG AGAACATCAG

4594 CCCAGATTTC ACCAATGAGG TTCTTGGCAT GCACACACAC AGAGTAAGAA CTGATTTAGA 4653
       CCAGATCTC ACCATCATTAT (nGRE)     CACACACAC A (CACA)
CTCTGG                                       GGACAC AGAGTAGGG (AP.1-TGFb)

4654 GGCTAACATT GACATTGGTG CCTGAGATGC AAGACTGAAA TTAGAAAGTT CTCCCAAAGA 4713
                             (GC2) GATGCT GATGGATAAT TTAGAAGCTT CTCCCACA

4714 TACACAGTTG TTTTAAAGCT AGGGGTGAGG GGGGAAATCT GCCGCTTCTA TAGGAATGCT 4773
                                                     (PEA.3)AGGAA GGT_

4774 CTCCCTGGAG CCTGGTAGGG TGCTGTCCTT GTGTTCTGGC TGGCTGTTAT TTTTCTCTGT 4833
    CTC (SSRE)              MIR Repeat Region

4834 CCCTGCTACG TCTTAAAGGA CTTGTTTGGA TCTCCAGTTC CTAGCATAGT GCCTGGCACA 4893
                          GGA CTTGTTTGTT CT (GRE-rTAT-II)        TGGGCACA
                GCAAAAAGGA TCTATTTGGA A (GRE-MMTV)

4894 GTGCAGGTTC TCAATGAGTT TGCAGAGTGA ATGGAAATAT AAACTAGAAA TATATCCTTG 4953
     GTGCCAA (NF-1           (HNF-1)C TGTGAAATAT TAACTAAA

4954 TTGAAATCAG CACACCAGTA GTCCTGGTGT AAGTGTGTGT ACGTGTGTGT GTGTGTGTGT 5013
```

FIG. 1D

```
5014 GTGTGTGTGT AAAACCAGGT GGAGATATAG GAACTATTAT TGGGGTATGG GTGCATAAAT 5073
                                                         cat/reverse cat box

5074 TGGGATGTTC TTTTTAAAAA GAAACTCCAA ACAGACTTCT GGAAGGTTAT TTTCTAAGAA 5133
  (1/2GRE)TGTTC T       (HSTF)         GAAACTTCT GGAATATTCC CGAACTTTC
              C CTTTTAGAAA GGA---CAAA ACAGAATG(nGRE-Prl)

5134 TCTTGCTGGC AGCGTGAAGG CAACCCCCCT GTGCACAGCC CCACCCAGCC TCACGTGGCC 5193
             (1/2 TRE)AGG CAA                T-CC CCAGGCTCCC -CAG(AP.2-SV40)
                                       GGAGAGCC CC (NF-KB)

5194 ACCTCTGTCT TCCCCCATGA AGGGCTGGCT CCCCAGTATA TATAAACCTC TCTGGAGCTC 5253
                                            tata box GGTC TC (SSRE)

5254 GGGCATGAGC CAGCAAGGC*C* ACCCATCCAG GCACCTCTCA GCACAGC 5300
                      Start Sites
```

FIG.1E

```
1                                                     ATC TTTGTTCAGT TTACCTCAGG GCTATTATGA 33
34 AATGAAATGA GATAACCAAT GTGAAAGTCC TATAAACTGT ATAGCCTCCA TTCGGATGTA 93
94 TGTCTTTGGC AGGATGATAA AGAATCAGGA AGAAGGAGTA TCCACGTTAG CCAAGTGTCC 153
154 AGGCTGTGTC TGCTCTTATT TTAGTGACAG ATGTTGCTCC TGACAGAAGC TATTCTTCAG 213
214 GAAACATCAC ATCCAATATG GTAAATCCAT CAAACAGGAG CTAAGAAACA GGAATGAGAT 273
274 GGGCACTTGC CCAAGGAAAA ATGCCAGGAG AGCAAATAAT GATGAAAAAT AAACTTTTCC 333
334 CTTTGTTTTT AATTTCAGGA AAAAATGATG AGGACCAAAA TCAATGAATA AGGAAAACAG 393
394 CTCAGAAAAA AGATGTTTCC AAATTGGTAA TTAAGTATTT GTTCCTTGGG AAGAGACCTC 453
454 CATGTGAGCT TGATGGGAAA ATGGGAAAAA CGTCAAAAGC ATGATCTGAT CAGATCCCAA 513
514 AGTGGATTAT TATTTTAAAA ACCAGATGGC ATCACTCTGG GGAGGCAAGT TCAGGAAGGT 573
574 CATGTTAGCA AAGGACATAA CAATAACAGC AAAATCAAAA TTCCGCAAAT GCAGGAGGAA 633
634 AATGGGGACT GGGAAAGCTT TCATAACAGT GATTAGGCAG TTGACCATGT TCGCAACACC 693
694 TCCCCGTCTA TACCAGGGAA CACAAAAATT GACTGGGCTA AGCCTGGACT TTCAAGGGAA 753
754 ATATGAAAAA CTGAGAGCAA AACAAAAGAC ATGGTTAAAA GGCAACCAGA ACATTGTGAG 813
814 CCTTCAAAGC AGCAGTGCCC CTCAGCAGGG ACCCTGAGGC ATTTGCCTTT AGGAAGGCCA 873
874 GTTTTCTTAA GGAATCTTAA GAAACTCTTG AAAGATCATG AATTTTAACC ATTTTAAGTA 933
934 TAAAACAAAT ATGCGATGCA TAATCAGTTT AGACATGGGT CCCAATTTTA TAAAGTCAGG 993
994 CATACAAGGA TAACGTGTCC CAGCTCCGGA TAGGTCAGAA ATCATTAGAA ATCACTGTGT 1053
1054 CCCCATCCTA ACTTTTTCAG AATGATCTGT CATAGCCCTC ACACACAGGC CCGATGTGTC 1113
1114 TGACCTACAA CCACATCTAC AACCCAAGTG CCTCAACCAT TGTTAACGTG TCATCTCAGT 1173
1174 AGGTCCCATT ACAAATGCCA CCTCCCCTGT GCAGCCCATC CCGCTCCACA GGAAGTCTCC 1233
1234 CCACTCTAGA CTTCTGCATC ACGATGTTAC AGCCAGAAGC TCCGTGAGGG TGAGGGTCTG 1293
1294 TGTCTTACAC CTACCTGTAT GCTCTACACC TGAGCTCACT GCAACCTCTG CCTCCCAGGT 1353
1354 TCAAGCAATT CTCCTGTCTC AGCCTCCCGC GTAGCTGGGA CTACAGGCGC ACGCCCGGCT 1413
1414 AATTTTTGTA TTGTTAGTAG AGATGGGGTT TCACCATATT AGCCCGGCTG GTCTTGAACT 1473
```

FIG.2A

```
1474 CCTGACCTCA GGTGATCCAC CCACCTCAGC CTCCTAAAGT GCTGGGATTA CAGGCATGAG 1533
1534 TCACCGCGCC CGGCCAAGGG TCAGTGTTTA ATAAGGAATA ACTTGAATGG TTTACTAAAC 1593
1594 CAACAGGGAA ACAGACAAAA GCTGTGATAA TTTCAGGGAT TCTTGGGATG GGGAATGGTG 1653
1654 CCATGAGCTG CCTGCCTAGT CCCAGACCAC TGGTCCTCAT CACTTTCTTC CCTCATCCTC 1713
1714 ATTTTCAGGC TAAGTTACCA TTTTATTCAC CATGCTTTTG TGGTAAGCCT CCACATCGTT 1773
1774 ACTGAAATAA GAGTATACAT AAACTAGTTC CATTTGGGGC CATCTGTGTG TGTGTATAGG 1833
1834 GGAGGAGGGC ATACCCCAGA GACTCCTTGA AGCCCCCGGC AGAGGTTTCC TCTCCAGCTG 1893
1894 GGGGAGCCCT GCAAGCACCC GGGGTCCTGG GTGTCCTGAG CAACCTGCCA GCCCGTGCCA 1953
1954 CTGGTTGTTT TGTTATCACT CTCTAGGGAC CTGTTGCTTT CTATTTCTGT GTGACTCGTT 2013
2014 CATTCATCCA GGCATTCATT GACAATTTAT TGAGTACTTA TATCTGCCAG ACACCAGAGA 2073
2074 CAAAATGGTG AGCAAAGCAG TCACTGCCCT ACCTTCGTGG AGGTGACAGT TTCTCATGGA 2133
2134 AGACGTGCAG AAGAAAATTA ATAGCCAGCC AACTTAAACC CAGTGCTGAA AGAAAGGAAA 2193
2194 TAAACACCAT CTTGAAGAAT TGTGCGCAGC ATCCCTTAAC AAGGCCACCT CCCTAGCGCC 2253
2254 CCCTGCTGCC TCCATCGTGC CCGGAGGCCC CCAAGCCCGA GTCTTCCAAG CCTCCTCCTC 2313
2314 CATCAGTCAC AGCGCTGCAG CTGGCCTGCC TCGCTTCCCG TGAATCGTCC TGGTGCATCT 2373
2374 GAGCTGGAGA CTCCTTGGCT CCAGGCTCCA GAAAGGAAAT GGAGAGGGAA ACTAGTCTAA 2433
2434 CGGAGAATCT GGAGGGGACA GTGTTTCCTC AGAGGGAAAG GGGCCTCCAC GTCCAGGAGA 2493
2494 ATTCCAGGAG GTGGGGACTG CAGGGAGTGG GGACGCTGGG GCTGAGCGGG TGCTGAAAGG 2553
2554 CAGGAAGGTG AAAAGGGCAA GGCTGAAGCT GCCCAGATGT TCAGTGTTGT TCACGGGGCT 2613
2614 GGGAGTTTTC CGTTGCTTCC TGTGAGCCTT TTTATCTTTT CTCTGCTTGG AGGAGAAGAA 2673
2674 GTCTATTTCA TGAAGGGATG CAGTTTCATA AAGTCAGCTG TTAAAATTCC AGGGTGTGCA 2733
2734 TGGGTTTTCC TTCACGAAGG CCTTTATTTA ATGGGAATAT AGGAAGCGAG CTCATTTCCT 2793
2794 AGGCCGTTAA TTCACGGAAG AAGTGACTGG AGTCTTTTCT TTCATGTCTT CTGGGCAACT 2853
2854 ACTCAGCCCT GTGGTGGACT TGGCTTATGC AAGACGGTCG AAAACCTTGG AATCAGGAGA 2913
2914 CTCGGTTTTC TTTCTGGTTC TGCCATTGGT TGGCTGTGCG ACCGTGGGCA AGTGTCTCTC 2973
2974 CTTCCCTGGG CCATAGTCTT CTCTGCTATA AAGACCCTTG CAGCTCTCGT GTTCTGTGAA 3033
3034 CACTTCCCTG TGATTCTCTG TGAGGGGGGA TGTTGAGAGG GGAAGGAGGC AGAGCTGGAG 3093
```

FIG.2B

3094 CAGCTGAGCC ACAGGGGAGG TGGAGGGGGA CAGGAAGGCA GGCAGAAGCT GGGTGCTCCA 3153
3154 TCAGTCCTCA CTGATCACGT CAGACTCCAG GACCGAGAGC CACAATGCTT CAGGAAAGCT 2943
2944 CAATGAACCC AACAGCCCACA TTTTCCTTCC CTAAGCATAG ACAATGGCAT TTGCCAATAA 3273
3274 CCAAAAAGAA TGCAGAGACT AACTGGTGGT AGCTTTTGCC TGGCATTCAA AAACTGGGCC 3333
3334 AGAGCAAGTG GAAAATGCCA GAGATTGTTA AACTTTTCAC CCTGACCAGC ACCCCACGCA 3393
3394 GCTCAGCAGT GACTGCTGAC AGCACGGAGT GACCTGCAGC GCAGGGGAGG AGAAGAAAAA 3453
3454 GAGAGGGATA GTGTATGAGC AAGAAAGACA GATTCATTCA AGGGCAGTGG GAATTGACCA 3513
3514 CAGGGATTAT AGTCCACGTG ATCCTGGGTT CTAGGAGGCA GGGCTATATT GTGGGGGGAA 3573
3574 AAAATCAGTT CAAGGGAAGT CGGGAGACCT GATTTCTAAT ACTATATTTT TCCTTTACAA 3633
3634 GCTGAGTAAT TCTGAGCAAG TCACAAGGTA GTAACTGAGG CTGTAAGATT ACTTAGTTTC 3693
3694 TCCTTATTAG GAACTCTTTT TCTCTGTGGA GTTAGCAGCA CAAGGGCAAT CCCGTTTCTT 3753
3754 TTAACAGGAA GAAAACATTC CTAAGAGTAA AGCCAAACAG ATTCAAGCCT AGGTCTTGCT 3813
3814 GACTATATGA TTGGTTTTTT GAAAAATCAT TTCAGCGATG TTTACTATCT GATTCAGAAA 3873
3874 ATGAGACTAG TACCCTTTGG TCAGCTGTAA ACAAACACCC ATTTGTAAAT GTCTCAAGTT 3933
3934 CAGGCTTAAC TGCAGAACCA ATCAAATAAG AATAGAATCT TTAGAGCAAA CTGTGTTTCT 3993
3994 CCACTCTGGA GGTGAGTCTG CCAGGGCAGT TTGGAAATAT TTACTTCACA AGTATTGACA 4053
4054 CTGTTGTTGG TATTAACAAC ATAAAGTTGC TCAAAGGCAA TCATTATTTC AAGTGGCTTA 4113
4114 AAGTTACTTC TGACAGTTTT GGTATATTTA TTGGCTATTG CCATTTGCTT TTTGTTTTTT 4173
4174 CTCTTTGGGT TTATTAATGT AAAGCAGGGA TTATTAACCT ACAGTCCAGA AAGCCTGTGA 4233
4234 ATTTGAATGA GGAAAAAATT ACGTTTTTAT TTTTACCACC TTCTAACTAA ATTTAACATT 4293
4294 TTATTCCATT GCGAATAGAG CCATAAACTC AAAGTGGTAA TAAGAGTACC TGTGATTTTG 4353
4354 TCATTACCAA TAGAAATCAC AGACATTTTA TACTATATTA CAGTTGTTGC AGGTACGTTG 4413
4414 TAAGTGAAAT ATTTATACTC AAAACTACTT TGAAATTAGA CCTCCTGCTG GATCTTGTTT 4473
4474 TTAACATATT AATAAAACAT GTTTAAAATT TTGATATTTT GATAATCATA TTTCATTATC 4533
4534 ATTTGTTTCC TTTGTAATCT ATATTTTATA TATTTGAAAA CATCTTTCTG AGAAGAGTTC 4593
4594 CCCAGATTTC ACCAATGAGG TTCTTGGCAT GCACACACAC AGAGTAAGAA CTGATTTAGA 4653
4654 GGCTAACATT GACATTGGTG CCTGAGATGC AAGACTGAAA TTAGAAAGTT CTCCCAAAGA 4713

FIG.2C

4714 TACACAGTTG TTTTAAAGCT AGGGGTGAGG GGGGAAATCT GCCGCTTCTA TAGGAATGCT 4773

4774 CTCCCTGGAG CCTGGTAGGG TGCTGTCCTT GTGTTCTGGC TGGCTGTTAT TTTTCTCTGT 4833

4834 CCCTGCTACG TCTTAAAGGA CTTGTTTGGA TCTCCAGTTC CTAGCATAGT GCCTGGCACA 4893

4894 GTGCAGGTTC TCAATGAGTT TGCAGAGTGA ATGGAAATAT AAACTAGAAA TATATCTTTG 4953

4954 TTGAAATCAG CACACCAGTA GTCCTGGTGT AAGTGTGTGT ACGTGTGTGTGTGT GTGTGTGTGT5017

5018 GTGTGTGTGT AAAACCAGGT GGAGATATAG GAACTATTAT TGGGGTATGG GTGCATAAAT 5077

5078 TGGGATGTTC TTTTTAAAAA GAAACTCCAA ACAGACTTCT GGAAGGTTAT TTTCTAAGAA 5137

5138 TCTTGCTGGC AGCGTGAAGG CAACCCCCCT GTGCACAGCC CCACCCAGCC TCACGTGGCC 5197

5198 ACCTCTGTCT TCCCCCATGA AGGGCTGGCT CCCCAGTATA TATAAACCTC TCTGGAGCTC 5257

5258 GGGCATGAGC CAGCAAGGCC ACCCATCCAG GCACCTCTCA GCACAGC 5304

FIG.2D

```
   1 ATCTTTGTTC AGTTTACCTC AGGGCTATTA TGAAATGAAA TGAGATAACC
  51 AATGTGAAAG TCCTATAAAC TGTATAGCCT CCATTCGGAT GTATGTCTTT
 101 GGCAGGATGA TAAAGAATCA GGAAGAAGGA GTATCCACGT TAGCCAAGTG
 151 TCCAGGCTGT GTCTGCTCTT ATTTTAGTGA CAGATGTTGC TCCTGACAGA
 201 AGCTATTCTT CAGGAAACAT CACATCCAAT ATGGTAAATC CATCAAACAG
 251 GAGCTAAGAA ACAGGAATGA GATGGGCACT TGCCCAAGGA AAAATGCCAG
 301 GAGAGCAAAT AATGATGAAA AATAAACTTT TCCCTTTGTT TTTAATTTCA
 351 GGAAAAAATG ATGAGGACCA AAATCAATGA ATAAGGAAAA CAGCTCAGAA
 401 AAAAGATGTT TCCAAATTGG TAATTAAGTA TTTGTTCCTT GGGAAGAGAC
 451 CTCCATGTGA GCTTGATGGG AAAATGGGAA AAACGTCAAA AGCATGATCT
 501 GATCAGATCC CAAAGTGGAT TATTATTTTA AAAACCAGAT GGCATCACTC
 551 TGGGGAGGCA AGTTCAGGAA GGTCATGTTA GCAAAGGACA TAACAATAAC
 601 AGCAAAATCA AAATTCCGCA AATGCAGGAG GAAAATGGGG ACTGGGAAAG
 651 CTTTCATAAC AGTGATTAGG CAGTTGACCA TGTTCGCAAC ACCTCCCCGT
 701 CTATACCAGG GAACACAAAA ATTGACTGGG CTAAGCCTGG ACTTTCAAGG
 751 GAAATATGAA AAACTGAGAG CAAAACAAAA GACATGGTTA AAAGGCAACC
 801 AGAACATTGT GAGCCTTCAA AGCAGCAGTG CCCCTCAGCA GGGACCCTGA
 851 GGCATTTGCC TTTAGGAAGG CCAGTTTTCT TAAGGAATCT TAAGAAACTC
 901 TTGAAAGATC ATGAATTTTA ACCATTTTAA GTATAAAACA AATATGCGAT
 951 GCATAATCAG TTTAGACATG GGTCCCAATT TTATAAAGTC AGGCATACAA
1001 GGATAACGTG TCCCAGCTCC GGATAGGTCA GAAATCATTA GAAATCACTG
1051 TGTCCCCATC CTAACTTTTT CAGAATGATC TGTCATAGCC CTCACACACA
1101 GGCCCGATGT GTCTGACCTA CAACCACATC TACAACCCAA GTGCCTCAAC
1151 CATTGTTAAC GTGTCATCTC AGTAGGTCCC ATTACAAATG CCACCTCCCC
1201 TGTGCAGCCC ATCCCGCTCC ACAGGAAGTC TCCCCACTCT AGACTTCTGC
1251 ATCACGATGT TACAGCCAGA AGCTCCGTGA GGGTGAGGGT CTGTGTCTTA
```

FIG.3A

1301 CACCTACCTG TATGCTCTAC ACCTGAGCTC ACTGCAACCT CTGCCTCCCA
1351 GGTTCAAGCA ATTCTCCTGT CTCAGCCTCC CGCGTAGCTG GGACTACAGG
1401 CGCACGCCCG GCTAATTTTT GTATTGTTAG TAGAGATGGG GTTTCACCAT
1451 ATTAGCCCGG CTGGTCTTGA ACTCCTGACC TCAGGTGATC CACCCACCTC
1501 AGCCTCCTAA AGTGCTGGGA TTACAGGCAT GAGTCACCGC GCCCGGCCAA
1551 GGGTCAGTGT TTAATAAGGA ATAACTTGAA TGGTTTACTA AACCAACAGG
1601 GAAACAGACA AAAGCTGTGA TAATTTCAGG GATTCTTGGG ATGGGGAATG
1651 GTGCCATGAG CTGCCTGCCT AGTCCCAGAC CACTGGTCCT CATCACTTTC
1701 TTCCCTCATC CTCATTTTCA GGCTAAGTTA CCATTTTATT CACCATGCTT
1751 TTGTGGTAAG CCTCCACATC GTTACTGAAA TAAGAGTATA CATAAACTAG
1801 TTCCATTTGG GGCCATCTGT GTGTGTGTAT AGGGGAGGAG GGCATACCCC
1851 AGAGACTCCT TGAAGCCCCC GGCAGAGGTT TCCTCTCCAG CTGGGGGAGC
1901 CCTGCAAGCA CCCGGGGTCC TGGGTGTCCT GAGCAACCTG CCAGCCCGTG
1951 CCACTGGTTG TTTTGTTATC ACTCTCTAGG GACCTGTTGC TTTCTATTTC
2001 TGTGTGACTC GTTCATTCAT CCAGGCATTC ATTGACAATT TATTGAGTAC
2051 TTATATCTGC CAGACACCAG AGACAAAATG GTGAGCAAAG CAGTCACTGC
2101 CCTACCTTCG TGGAGGTGAC AGTTTCTCAT GGAAGACGTG CAGAAGAAAA
2151 TTAATAGCCA GCCAACTTAA ACCCAGTGCT GAAAGAAAGG AAATAAACAC
2201 CATCTTGAAG AATTGTGCGC AGCATCCCTT AACAAGGCCA CCTCCCTAGC
2251 GCCCCCTGCT GCCTCCATCG TGCCCGGAGG CCCCCAAGCC CGAGTCTTCC
2301 AAGCCTCCTC CTCCATCAGT CACAGCGCTG CAGCTGGCCT GCCTCGCTTC
2351 CCGTGAATCG TCCTGGTGCA TCTGAGCTGG AGACTCCTTG GCTCCAGGCT
2401 CCAGAAAGGA AATGGAGAGG GAAACTAGTC TAACGGAGAA TCTGGAGGGG
2451 ACAGTGTTTC CTCAGAGGGA AAGGGGCCTC CACGTCCAGG AGAATTCCAG
2501 GAGGTGGGGA CTGCAGGGAG TGGGGACGCT GGGGCTGAGC GGGTGCTGAA
2551 AGGCAGGAAG GTGAAAAGGG CAAGGCTGAA GCTGCCCAGA TGTTCAGTGT
2601 TGTTCACGGG GCTGGGAGTT TTCCGTTGCT TCCTGTGAGC CTTTTTATCT

FIG.3B

```
2651 TTTCTCTGCT TGGAGGAGAA GAAGTCTATT TCATGAAGGG ATGCAGTTTC
2701 ATAAAGTCAG CTGTTAAAAT TCCAGGGTGT GCATGGGTTT TCCTTCACGA
2751 AGGCCTTTAT TTAATGGGAA TATAGGAAGC GAGCTCATTT CCTAGGCCGT
2801 TAATTCACGG AAGAAGTGAC TGGAGTCTTT TCTTTCATGT CTTCTGGGCA
2851 ACTACTCAGC CCTGTGGTGG ACTTGGCTTA TGCAAGACGG TCGAAAACCT
2901 TGGAATCAGG AGACTCGGTT TTCTTTCTGG TTCTGCCATT GGTTGGCTGT
2951 GCGACCGTGG GCAAGTGTCT CTCCTTCCCT GGGCCATAGT CTTCTCTGCT
3001 ATAAAGACCC TTGCAGCTCT CGTGTTCTGT GAACACTTCC CTGTGATTCT
3051 CTGTGAGGGG GGATGTTGAG AGGGGAAGGA GGCAGAGCTG GAGCAGCTGA
3101 GCCACAGGGG AGGTGGAGGG GGACAGGAAG GCAGGCAGAA GCTGGGTGCT
3151 CCATCAGTCC TCACTGATCA CGTCAGACTC CAGGACCGAG AGCCACAATG
3201 CTTCAGGAAA GCTCAATGAA CCCAACAGCC ACATTTTCCT TCCCTAAGCA
3251 TAGACAATGG CATTTGCCAA TAACCAAAAA GAATGCAGAG ACTAACTGGT
3301 GGTAGCTTTT GCCTGGCATT CAAAAACTGG GCCAGAGCAA GTGGAAAATG
3351 CCAGAGATTG TTAAACTTTT CACCCTGACC AGCACCCCAC GCAGCTCAGC
3401 AGTGACTGCT GACAGCACGG AGTGACCTGC AGCGCAGGGG AGGAGAAGAA
3451 AAAGAGAGGG ATAGTGTATG AGCAAGAAAG ACAGATTCAT TCAAGGGCAG
3501 TGGGAATTGA CCACAGGGAT TATAGTCCAC GTGATCCTGG GTTCTAGGAG
3551 GCAGGGCTAT ATTGTGGGGG GAAAAAATCA GTTCAAGGGA AGTCGGGAGA
3601 CCTGATTTCT AATACTATAT TTTTCCTTTA CAAGCTGAGT AATTCTGAGC
3651 AAGTCACAAG GTAGTAACTG AGGCTGTAAG ATTACTTAGT TTCTCCTTAT
3701 TAGGAACTCT TTTTCTCTGT GGAGTTAGCA GCACAAGGGC AATCCCGTTT
3751 CTTTTAACAG GAAGAAAACA TTCCTAAGAG TAAAGCCAAA CAGATTCAAG
3801 CCTAGGTCTT GCTGACTATA TGATTGGTTT TTTGAAAAAT CATTTCAGCG
3851 ATGTTTACTA TCTGATTCAG AAAATGAGAC TAGTACCCTT TGGTCAGCTG
3901 TAAACAAACA CCCATTTGTA AATGTCTCAA GTTCAGGCTT AACTGCAGAA
3951 CCAATCAAAT AAGAATAGAA TCTTTAGAGC AAACTGTGTT TCTCCACTCT
```

FIG.3C

```
4001 GGAGGTGAGT CTGCCAGGGC AGTTTGGAAA TATTTACTTC ACAAGTATTG
4051 ACACTGTTGT TGGTATTAAC AACATAAAGT TGCTCAAAGG CAATCATTAT
4101 TTCAAGTGGC TTAAAGTTAC TTCTGACAGT TTTGGTATAT TTATTGGCTA
4151 TTGCCATTTG CTTTTTGTTT TTTCTCTTTG GGTTTATTAA TGTAAAGCAG
4201 GGATTATTAA CCTACAGTCC AGAAAGCCTG TGAATTTGAA TGAGGAAAAA
4251 ATTACATTTT TGTTTTTACC ACCTTCTAAC TAAATTTAAC ATTTTATTCC
4301 ATTGCGAATA GAGCCATAAA CTCAAAGTGG TAATAACAGT ACCTGTGATT
4351 TTGTCATTAC CAATAGAAAT CACAGACATT TTATACTATA TTACAGTTGT
4401 TGCAGATACG TTGTAAGTGA AATATTTATA CTCAAAACTA CTTTGAAATT
4451 AGACCTCCTG CTGGATCTTG TTTTTAACAT ATTAATAAAA CATGTTTAAA
4501 ATTTTGATAT TTTGATAATC ATATTTCATT ATCATTTGTT TCCTTTGTAA
4551 TCTATATTTT ATATATTTGA AAACATCTTT CTGAGAAGAG TTCCCCAGAT
4601 TTCACCAATG AGGTTCTTGG CATGCACACA CACAGAGTAA GAACTGATTT
4651 AGAGGCTAAC ATTGACATTG GTGCCTGAGA TGCAAGACTG AAATTAGAAA
4701 GTTCTCCCAA AGATACACAG TTGTTTTAAA GCTAGGGGTG AGGGGGGAAA
4751 TCTGCCGCTT CTATAGGAAT GCTCTCCCTG GAGCCTGGTA GGGTGCTGTC
4801 CTTGTGTTCT GGCTGGCTGT TATTTTTCTC TGTCCCTGCT ACGTCTTAAA
4851 GGACTTGTTT GGATCTCCAG TTCCTAGCAT AGTGCCTGGC ACAGTGCAGG
4901 TTCTCAATGA GTTTGCAGAG TGAATGGAAA TATAAACTAG AAATATATCC
4951 TTGTTGAAAT CAGCACACCA GTAGTCCTGG TGTAAGTGTG TGTACGTGTG
5001 TGTGTGTGTG TGTGTGTGTG TGTAAAACCA GGTGGAGATA TAGGAACTAT
5051 TATTGGGGTA TGGGTGCATA AATTGGGATG TTCTTTTTAA AAAGAAACTC
5101 CAAACAGACT TCTGGAAGGT TATTTTCTAA GAATCTTGCT GGCAGCGTGA
5151 AGGCAACCCC CCTGTGCACA GCCCCACCCA GCCTCACGTG GCCACCTCTG
5201 TCTTCCCCCA TGAAGGGCTG GCTCCCCAGT ATATATAAAC CTCTCTGGAG
5251 CTCGGGCATG AGCCAGCAAG GCCACCCATC CAGGCACCTC TCAGCACAGC 5300
```

FIG.3D

```
1 AGAGCTTTCCAGAGGAAGCCTCACCAAGCCTCTGCAATGAGGTTCTTCTGTGCACGTTGC 60
61 TGCAGCTTTGGGCCTGAGATGCCAGCTGTCCAGCTGCTGCTTCTGGCCTGCCTGGTGTGG 120
121 GATGTGGGGGCCAGGACAGCTCAGCTCAGGAAGGCCAATGACCAGAGTGGCCGATGCCAG 180
181 TATACCTTCAGTGTGGCCAGTCCCAATGAATCCAGCTGCCCAGAGCAGAGCCAGGCCATG 240
241 TCAGTCATCCATAACTTACAGAGAGACAGCAGCACCCAACGCTTAGACCTGGAGGCCACC 300
301 AAAGCTCGACTCAGCTCCCTGGAGAGCCTCCTCCACCAATTGACCTTGGACCAGGCTGCC 360
361 AGGCCCCAGGAGACCCAGGAGGGGCTGCAGAGGGAGCTGGGCACCCTGAGGCGGGAGCGG 420
421 GACCAGCTGGAAACCCAAACCAGAGAGTTGGAGACTGCCTACAGCAACCTCCTCCGAGAC 480
481 AAGTCAGTTCTGGAGGAAGAGAAGAAGCGACTAAGGCAAGAAAATGAGAATCTGGCCAGG 540

541 AGGTTGGAAAGCAGCAGCCAGGAGGTAGCAAGGCTGAGAAGGGGCCAGTGTCCCCAGACC 600
601 CGAGACACTGCTCGGGCTGTGCCACCAGGCTCCAGAGAAG

                          (intron #1) gtaagaatgcagagtgggggactct
gagttcagcaggtgatatggctcgtagtgacctgctacaggcgctccaggcctccctgccctttctccta
gagactgcacagctagcacaagacagatgaattaaggaaagcacacgatcaccttcaagtattacta
gtaatttagctcctgagagcttcatttagattagtggttcagagttcttgtgcccctccatgtcag-----
------------------------     Intron I ~10 Kb--------------------------
aaggtaggcacattgccctgcaatttataatttatgaggtgttcaattatggaattgtcaaatattaaca
aaagtagagagactacaatgaactccaatgtagccataactcaggcccaactgttatcagcacagtcc
aatcatgttttatctttccttctctgacccccaacccatccccagtccttatctaaaatcaaatatcaaaca
ccatactctttgggagcctatttatttagttagttagttttcagacagagtttctttcttgttcccaagctgg
agtacaatagtgtagtctcggctaacagcaatctccccctccttggttcaagcaattctcctgcctcagtc
tcccaagaagctgggattatagacacctgccaccacatccagctaatttttttgtgttttagaaaagaca
gggtttcaccatgttggccaggctggtttcgaactcctgacctcaggtgatccgcctgcctcggcctccca
aagtgctgggattacaggcatgagccaccacgcctggccggcagcctatttaaatgtcatcctcaacat
agtcaatccttgggccatttttttcttacagtaaaattttgtctctttcttttaatcag

                          (exon #2) TT TCT ACG TGG AAT TTG GAC

661 ACT TTG GCC TTC CAG GAA CTG AAG TCC GAG CTA ACT GAA GTT CCT GCT TCC CGA ATT TTG 720
721 AAG GAG AGC CCA TCT GGC TAT CTC AGG AGT GGA GAG GGA GAC ACCG

(intron #2)
gtatgaagttaagtttcttccctttttgtgcccacgtggtctttattcatgtctagtgctgtgttcagagaa
tcagtatagggtaaatgcccacccaagggggaaattaacttccctgggagcagagggaggggagga
gaagaggaacagaactctctctctctctctgttacccttgt------Intron II ~ 3 kb-------
```

FIG.3E

```
tggctctgccaagcttccgcatgatcattgtctgtgtttggaagattatggattaagtggtgcttcgtttt
ctttctgaatttaccag
                                        (exon #3) GA TGT GGA GAA CTA 780

781  GTT TGG GTA GGA GAG CCT CTC ACG CTG AGA ACA GCA GAA ACA ATT ACT GGC AAG TAT GGT 840
841  GTG TGG ATG CGA GAC CCC AAG CCC ACC TAC CCC TAC ACC CAG GAG ACC ACG TGG AGA ATC 900
901  GAC ACA GTT GGC ACG GAT GTC CGC CAG GTT TTT GAG TAT GAC CTC ATC AGC CAG TTT ATG 960
961  CAG GGC TAC CCT TCT AAG GTT CAC ATA CTG CCT AGG CCA CTG GAA AGC ACG GGT GCT GTG 1020
1021 GTG TAC TCG GGG AGC CTC TAT TTC CAG GGC GCT GAG TCC AGA ACT GTC ATA AGA TAT GAG 1080
1081 CTG AAT ACC GAG ACA GTG AAG GCT GAG AAG GAA ATC CCT GGA GCT GGC TAC CAC GGA CAG 1140
1141 TTC CCG TAT TCT TGG GGT GGC TAC ACG GAC ATT GAC TTG GCT GTG GAT GAA GCA GGC CTC 1200
1201 TGG GTC ATT TAC AGC ACC GAT GAG GCC AAA GGT GCC ATT GTC CTC TCC AAA CTG AAC CCA 1260
1261 GAG AAT CTG GAA CTC GAA CAA ACC TGG GAG ACA AAC ATC CGT AAG CAG TCA GTC GCC AAT 1320
1321 GCC TTC ATC ATC TGT GGC ACC TTG TAC ACC GTC AGC AGC TAC ACC TCA GCA GAT GCT ACC 1380
1381 GTC AAC TTT GCT TAT GAC ACA GGC ACA GGT ATC AGC AAG ACC CTG ACC ATC CCA TTC AAG 1440
1441 AAC CGC TAT AAG TAC AGC AGC ATG ATT GAC TAC AAC CCC CTG GAG AAG AAG CTC TTT GCC 1500
1501 TGG GAC AAC TTG AAC ATG GTC ACT TAT GAC ATC AAG CTC TCC AAG ATG

                                    (3' flanking region) TGA AAA GCC TCC 1560

1561 AAG CTG TAC AGG CAA TGG CAG AAG GAG ATG CTC AGG GCT CCT GGG GGG AGC AGG CTG AAG 1620
1621 GGA GAG CCA GCC AGC CAG GGC CCA GGC AGC TTT GAC TGC TTT CCA AGT TTT CAT TAA TCC 1680
1681 AGA AGG ATG AAC ATG GTC ACC ATC TAA CTA TTC AGG AAT TGT AGT CTG AGG GCG TAG ACA 1740
1741 ATT TCA TAT AAT AAA TAT CCT TTA TCT TCT GTC AGC ATT TAT GGG ATG TTT AAT GAC ATA 1800
1801 GTT CAA GTT TTC TTG TGA TTT GGG GCA AAA GCT GTA AGG CAT AAT AGT CTT TTC CTG AAA 1860
1861 ACC ATT GCT CTT GCA TGT TAC ATG GTT ACC ACA AGC CAC AAT AAA AAG CAT AAC TTC TAA 1920
1921 AGG AAG CAG AAT AGC TCC TCT GGC CAG CAT CGA ATA TAA GTA AGA TGC ATT TAC TAC AGT 1980
1981 TGG CTT CTA ATG CTT CAG ATA GAA TAC AGT TGG GTC TCA CAT AAC CCT TAC ATT GTG AAA 2040
2041 TAA AAT TTT CTT ACC CAA CGT TCT CTT CCT TGA ACT TTG TGG GAA TCT TTG CTT AAG AGA 2100
2101 AGG ATA TAG ATT CCA ACC ATC AGG TAA TTC CTT CAG GTT GGG AGA TGT GAT TGC AGG ATG 2160
```

FIG.3F

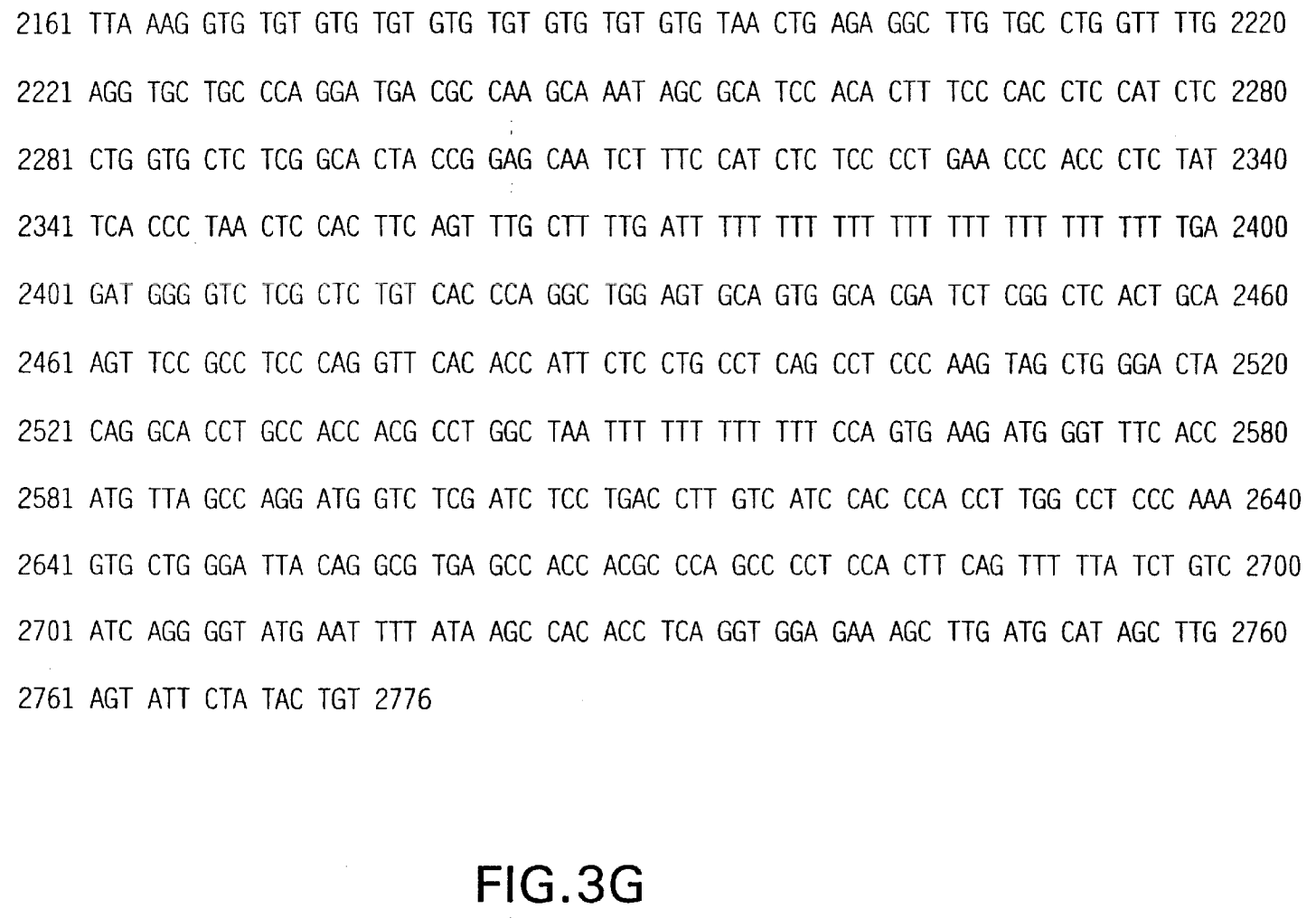

2161 TTA AAG GTG TGT GTG TGT GTG TGT GTG TGT GTG TAA CTG AGA GGC TTG TGC CTG GTT TTG 2220

2221 AGG TGC TGC CCA GGA TGA CGC CAA GCA AAT AGC GCA TCC ACA CTT TCC CAC CTC CAT CTC 2280

2281 CTG GTG CTC TCG GCA CTA CCG GAG CAA TCT TTC CAT CTC TCC CCT GAA CCC ACC CTC TAT 2340

2341 TCA CCC TAA CTC CAC TTC AGT TTG CTT TTG ATT TTT TTT TTT TTT TTT TTT TTT TTT TGA 2400

2401 GAT GGG GTC TCG CTC TGT CAC CCA GGC TGG AGT GCA GTG GCA CGA TCT CGG CTC ACT GCA 2460

2461 AGT TCC GCC TCC CAG GTT CAC ACC ATT CTC CTG CCT CAG CCT CCC AAG TAG CTG GGA CTA 2520

2521 CAG GCA CCT GCC ACC ACG CCT GGC TAA TTT TTT TTT TTT CCA GTG AAG ATG GGT TTC ACC 2580

2581 ATG TTA GCC AGG ATG GTC TCG ATC TCC TGAC CTT GTC ATC CAC CCA CCT TGG CCT CCC AAA 2640

2641 GTG CTG GGA TTA CAG GCG TGA GCC ACC ACGC CCA GCC CCT CCA CTT CAG TTT TTA TCT GTC 2700

2701 ATC AGG GGT ATG AAT TTT ATA AGC CAC ACC TCA GGT GGA GAA AGC TTG ATG CAT AGC TTG 2760

2761 AGT ATT CTA TAC TGT 2776

FIG.3G

```
TIGR        -TGAVVYSGS LYFQGAESRT VIRYELNTET VKAEKEIPGA GYHGQFPYSW GGYTDIDLAV 59
ym08h12.rl  ---------- ---------- --RFDLKTET ILKTRSLDYA GYNNMYHYAW GGHSDIDLMV 38
1B426bAMZ   GTGQVVYNGS IYFNKFQSHI IIRFDLKTET ILKTRSLDYA GYNNMYHYAW GGHSDIDLMV 60
ranofm      GAGVVVHNNN LYYNCFNSHD MCRASL-TSG VYQKKPLLNA LFNNRFSYAG TMFQDMDFSS 59
Consensus   ..G.VV.... .Y.....S.. ..R..L.TET ......L..A GYNN...YAW GG..DIDL.V 60

TIGR        DEAGLWVIYS TDEAKGAIVL SKLNPENLEL EQTWETNIRK QSVANAFIIC GTLYTVSSYT 119
ym08h12.rl  DESGLWAVYA TNQNAGNIVV SRLDPVSLQT LQTWNTSYPK RXPGXAFIIC GTCYVTNGY- 97
1B426bAMZ   DENGLWAVYA TNQNAGNIVI SKLDPVSLQI LQTWNTSYPK RSAGEAFIIC GTLYVTNGYS 120
ranofm      DEKGLWVIFT TEKSAGKIVV GKVNVATFTV DNIWITTQNK SDASNAFMIC GVLYVVTRSLG 119
Consensus   DE.GLW..Y. T...AG.IV. SKL.P..L.. .QTW.T...K .....AFIIC GTLYVT..Y. 120

TIGR        SADATVNFAY DTGTGISKTL TIPFKNRYKY SSMIDYNPLE KKLFAWDNLN MVTYDIKLS  178
ym08h12.rl  SGGTKVHYAY QTNAST---- -------YEY ---IDI-PFQ NKLXP----- --HFPC---  131
1B426bAMZ   GG-TKVHYAY QTNASTYEYI DIPFQNKYSH ISMLDYNPKD RALYAWNNGH QTLYNVTLF  178
ranofm      PKMEEVFYMF DTKTGKEGHL SIMMEKMAEK VHSLSYNSND RKLYMFSEGY LLHYDIAL-  177
Consensus   .....V.YAY .T........ .I.....Y.. ....DYNP.. .KL....... ...Y...L.  178
```

FIG.6

```
  1 AGA GCT TTC CAG AGG AAG CCT CAC CAA GCC TCT GCA ATG AGG TTC TTC TGT GCA CGT TGC 60
 61 TGC AGC TTT GGG CCT GAG ATG CCA GCT GTC CAG CTG CTG CTT CTG GCC TGC CTG GTG TGG 120
121 GAT GTG GGG GCC AGG ACA GCT CAG CTC AGG AAG GCC AAT GAC CAG AGT GGC CGA TGC CAG 180
181 TAT ACC TTC AGT GTG GCC AGT CCC AAT GAA TCC AGC TGC CCA GAG CAG AGC CAG GCC ATG 240
241 TCA GTC ATC CAT AAC TTA CAG AGA GAC AGC AGC ACC CAA CGC TTA GAC CTG GAG GCC ACC 300
301 AAA GCT CGA CTC AGC TCC CTG GAG AGC CTC CTC CAC CAA TTG ACC TTG GAC CAG GCT GCC 360
361 AGG CCC CAG GAG ACC CAG GAG GGG CTG CAG AGG GAG CTG GGC ACC CTG AGG CGG GAG CGG 420
421 GAC CAG CTG GAA ACC CAA ACC AGA GAG TTG GAG ACT GCC TAC AGC AAC CTC CTC CGA GAC 480
481 AAG TCA GTT CTG GAG GAA GAG AAG AAG CGA CTA AGG CAA GAA AAT GAG AAT CTG GCC AGG 540
541 AGG TTG GAA AGC AGC AGC CAG GAG GTA GCA AGG CTG AGA AGG GGC CAG TGT CCC CAG ACC 600
601 CGA GAC ACT GCT CGG GCT GTG CCA CCA GGC TCC AGA GAA GTT TCT ACG TGG AAT TTG GAC 660
661 ACT TTG GCC TTC CAG GAA CTG AAG TCC GAG CTA ACT GAA GTT CCT GCT TCC CGA ATT TTG 720
721 AAG GAG AGC CCA TCT GGC TAT CTC AGG AGT GGA GAG GGA GAC ACC GGA TGT GGA GAA CTA 780
781 GTT TGG GTA GGA GAG CCT CTC ACG CTG AGA ACA GCA GAA ACA ATT ACT GGC AAG TAT GGT 840
841 GTG TGG ATG CGA GAC CCC AAG CCC ACC TAC CCC TAC ACC CAG GAG ACC ACG TGG AGA ATC 900
```

FIG.7A

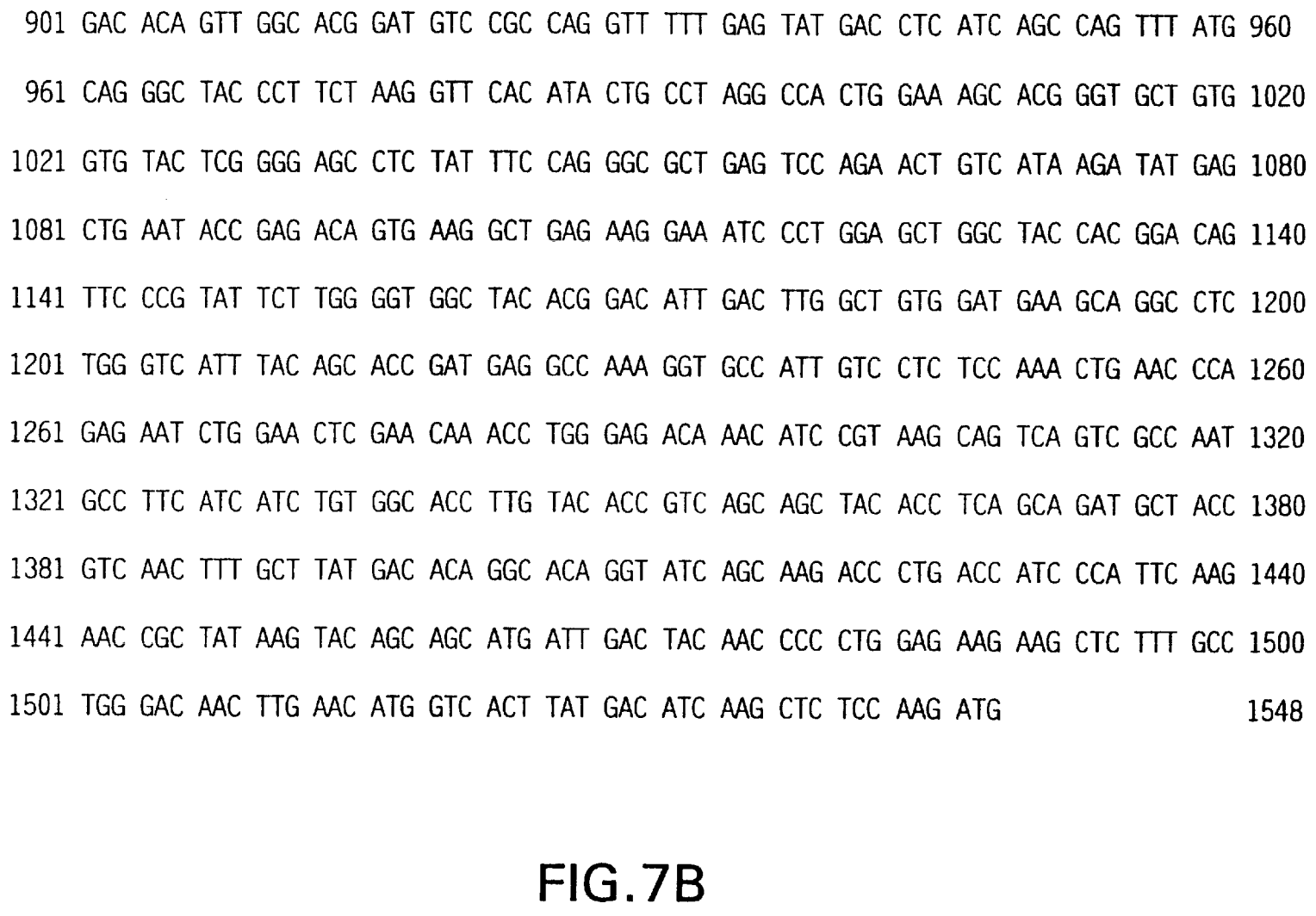

901 GAC ACA GTT GGC ACG GAT GTC CGC CAG GTT TTT GAG TAT GAC CTC ATC AGC CAG TTT ATG 960

961 CAG GGC TAC CCT TCT AAG GTT CAC ATA CTG CCT AGG CCA CTG GAA AGC ACG GGT GCT GTG 1020

1021 GTG TAC TCG GGG AGC CTC TAT TTC CAG GGC GCT GAG TCC AGA ACT GTC ATA AGA TAT GAG 1080

1081 CTG AAT ACC GAG ACA GTG AAG GCT GAG AAG GAA ATC CCT GGA GCT GGC TAC CAC GGA CAG 1140

1141 TTC CCG TAT TCT TGG GGT GGC TAC ACG GAC ATT GAC TTG GCT GTG GAT GAA GCA GGC CTC 1200

1201 TGG GTC ATT TAC AGC ACC GAT GAG GCC AAA GGT GCC ATT GTC CTC TCC AAA CTG AAC CCA 1260

1261 GAG AAT CTG GAA CTC GAA CAA ACC TGG GAG ACA AAC ATC CGT AAG CAG TCA GTC GCC AAT 1320

1321 GCC TTC ATC ATC TGT GGC ACC TTG TAC ACC GTC AGC AGC TAC ACC TCA GCA GAT GCT ACC 1380

1381 GTC AAC TTT GCT TAT GAC ACA GGC ACA GGT ATC AGC AAG ACC CTG ACC ATC CCA TTC AAG 1440

1441 AAC CGC TAT AAG TAC AGC AGC ATG ATT GAC TAC AAC CCC CTG GAG AAG AAG CTC TTT GCC 1500

1501 TGG GAC AAC TTG AAC ATG GTC ACT TAT GAC ATC AAG CTC TCC AAG ATG 1548

FIG.7B

```
1                                                    Met Arg Phe Phe Cys Ala Arg Cys 20
21  Cys Ser Phe Gly Pro Glu Met Pro Ala Val Gln Leu Leu Leu Leu Ala Cys Leu Val Trp 40
41  Asp Val Gly Ala Arg Thr Ala Gln Leu Arg Lys Ala Asn Asp Gln Ser Gly Arg Cys Gln 60
61  Tyr Thr Phe Ser Val Ala Ser Pro Asn Glu Ser Ser Cys Pro Glu Gln Ser Gln Ala Met 80
81  Ser Val Ile His Asn Leu Gln Arg Asp Ser Ser Thr Gln Arg Leu Asp Leu Glu Ala Thr 100
101 Lys Ala Arg Leu Ser Ser Leu Glu Ser Leu Leu His Gln Leu Thr Leu Asp Gln Ala Ala 120
121 Arg Pro Gln Glu Thr Gln Glu Gly Leu Gln Arg Glu Leu Gly Thr Leu Arg Arg Glu Arg 140
141 Asp Gln Leu Glu Thr Gln Thr Arg Glu Leu Glu Thr Ala Tyr Ser Asn Leu Leu Arg Asp 160
161 Lys Ser Val Leu Glu Glu Glu Lys Lys Arg Leu Arg Gln Glu Asn Glu Asn Leu Ala Arg 180
181 Arg Leu Glu Ser Ser Ser Gln Glu Val Ala Arg Leu Arg Arg Gly Gln Cys Pro gln Thr 200
201 Arg Asp Thr Ala Arg Ala Val Pro Pro Gly Ser Arg Glu Val Ser Thr Trp Asn Leu Asp 220
221 Thr Leu Ala Phe Gln Glu Leu Lys Ser Glu Leu Thr Glu Val Pro Ala Ser Arg Ile Leu 240
241 Lys Glu Ser Pro Ser Gly Tyr Leu Arg Ser Gly Glu Gly Asp Thr Gly Cys Gly Glu Leu 260
261 Val Trp Val Gly Glu Pro Leu Thr Leu Arg Thr Ala Glu Thr Ile Thr Gly Lys Tyr Gly 280
281 Val Trp Met Arg Asp Pro Lys Pro Thr Tyr Pro Tyr Thr Gln Glu Thr Thr Trp Arg Ile 300
```

FIG.8A

301 Asp Thr Val Gly Thr Asp Val Arg Gln Val Phe Glu Tyr Asp Leu Ile Ser Gln Phe Met 320

321 Gln Gly Tyr Pro Ser Lys Val His Ile Leu Pro Arg Pro Leu Glu Ser Thr Gly Ala Val 340

341 Val Tyr Ser Gly Ser Leu Tyr Phe Gln Gly Ala Glu Ser Arg Thr Val Ile Arg Tyr Glu 360

361 Leu Asn Thr Glu Thr Val Lys Ala Glu Lys Glu Ile Pro Gly Ala Gly Tyr His Gly Gln 380

381 Phe Pro Tyr Ser Trp Gly Gly Tyr Thr Asp Ile Asp Leu Ala Val Asp Glu Ala Gly Leu 400

401 Trp Val Ile Tyr Ser Thr Asp Glu Ala Lys Gly Ala Ile Val Leu Ser Lys Leu Asn Pro 420

421 Glu Asn Leu Glu Leu Glu Gln Thr Trp Glu Thr Asn Ile Arg Lys Gln Ser Val Ala Asn 440

441 Ala Phe Ile Ile Cys Gly Thr Leu Tyr Thr Val Ser Ser Tyr Thr Ser Ala Asp Ala Thr 460

461 Val Asn Phe Ala Tyr Asp Thr Gly Thr Gly Ile Ser Lys Thr Leu Thr Ile Pro Phe Lys 480

481 Asn Arg Tyr Lys Tyr Ser Ser Met Ile Asp Tyr Asn Pro Leu Glu Lys Lys Leu Phe Ala 500

501 Trp Asp Asn Leu Asn Met Val Thr Tyr Asp Ile Lys Leu Ser Lys Met

FIG.8B

SEQUENCE LISTING

<160> NUMBER OF SEQ ID NOS: 38

<210> SEQ ID NO 1
<211> LENGTH: 5300
<212> TYPE: DNA
<213> ORGANISM: Homo sapiens

<400> SEQUENCE: 1
atctttgttc agtttacctc agggctatta tgaaatgaaa tgagataacc aatgtgaaag 60
tcctataaac tgtatagcct ccattcggat gtatgtcttt ggcaggatga taaagaatca 120
ggaagaagga gtatccacgt tagccaagtg tccaggctgt gtctgctctt attttagtga 180
cagatgttgc tcctgacaga agctattctt caggaaacat cacatccaat atggtaaatc 240
catcaaacag gagctaagaa acaggaatga gatgggcact tgcccaagga aaaatgccag 300
gagagcaaat aatgatgaaa aataaacttt tccctttgtt tttaatttca ggaaaaaatg 360
atgaggacca aaatcaatga ataaggaaaa cagctcagaa aaaagatgtt tccaaattgg 420
taattaagta tttgttcctt gggaagagac ctccatgtga gcttgatggg aaaatgggaa 480
aaacgtcaaa agcatgatct gatcagatcc caaagtggat tattatttta aaaaccagat 540
ggcatcactc tggggaggca agttcaggaa ggtcatgtta gcaaaggaca taacaataac 600
agcaaaatca aaattccgca aatgcaggag gaaaatgggg actgggaaag ctttcataac 660
agtgattagg cagttgacca tgttcgcaac acctccccgt ctataccagg gaacacaaaa 720
attgactggg ctaagcctgg actttcaagg gaaatatgaa aaactgagag caaaacaaaa 780
gacatggtta aaaggcaacc agaacattgt gagccttcaa agcagcagtg cccctcagca 840
gggaccctga ggcatttgcc tttaggaagg ccagttttct taaggaatct taagaaactc 900
ttgaaagatc atgaatttta accattttaa gtataaaaca aatatgcgat gcataatcag 960
tttagacatg ggtcccaatt ttataaagtc aggcatacaa ggataacgtg tcccagctcc 1020
ggataggtca gaaatcatta gaaatcactg tgtccccatc ctaacttttt cagaatgatc 1080
tgtcatagcc ctcacacaca ggcccgatgt gtctgaccta caaccacatc tacaacccaa 1140
gtgcctcaac cattgttaac gtgtcatctc agtaggtccc attacaaatg ccacctcccc 1200
tgtgcagccc atcccgctcc acaggaagtc tccccactct agacttctgc atcacgatgt 1260
tacagccaga agctccgtga gggtgagggt ctgtgtctta cacctacctg tatgctctac 1320
acctgagctc actgcaacct ctgcctccca ggttcaagca attctcctgt ctcagcctcc 1380
cgcgtagctg ggactacagg cgcacgcccg gctaattttt gtattgttag tagagatggg 1440
gtttcaccat attagcccgg ctggtcttga actcctgacc tcaggtgatc cacccacctc 1500
agcctcctaa agtgctggga ttacaggcat gagtcaccgc gcccggccaa gggtcagtgt 1560
ttaataagga ataacttgaa tggtttacta aaccaacagg gaaacagaca aaagctgtga 1620

-continued

```
taatttcagg gattcttggg atggggaatg gtgccatgag ctgcctgcct agtcccagac   1680
cactggtcct catcactttc ttccctcatc ctcattttca ggctaagtta ccattttatt   1740
caccatgctt ttgtggtaag cctccacatc gttactgaaa taagagtata cataaactag   1800
ttccatttgg ggccatctgt gtgtgtgtat aggggaggag ggcatacccc agagactcct   1860
tgaagccccc ggcagaggtt tcctctccag ctgggggagc cctgcaagca cccggggtcc   1920
tgggtgtcct gagcaacctg ccagcccgtg ccactggttg ttttgttatc actctctagg   1980
gacctgttgc tttctatttc tgtgtgactc gttcattcat ccaggcattc attgacaatt   2040
tattgagtac ttatatctgc cagacaccag agacaaaatg gtgagcaaag cagtcactgc   2100
cctaccttcg tggaggtgac agtttctcat ggaagacgtg cagaagaaaa ttaatagcca   2160
gccaacttaa acccagtgct gaaagaaagg aaataaacac catcttgaag aattgtgcgc   2220
agcatccctt aacaaggcca cctccctagc gccccctgct gcctccatcg tgcccggagg   2280
cccccaagcc cgagtcttcc aagcctcctc ctccatcagt cacagcgctg cagctggcct   2340
gcctcgcttc ccgtgaatcg tcctggtgca tctgagctgg agactccttg gctccaggct   2400
ccagaaagga aatggagagg gaaactagtc taacggagaa tctggagggg acagtgtttc   2460
ctcagaggga aaggggcctc cacgtccagg agaattccag gaggtgggga ctgcagggag   2520
tggggacgct ggggctgagc gggtgctgaa aggcaggaag gtgaaaaggg caaggctgaa   2580
gctgcccaga tgttcagtgt tgttcacggg gctgggagtt ttccgttgct tcctgtgagc   2640
ctttttatct tttctctgct tggaggagaa gaagtctatt tcatgaaggg atgcagtttc   2700
ataaagtcag ctgttaaaat tccagggtgt gcatgggttt tccttcacga aggcctttat   2760
ttaatgggaa tataggaagc gagctcattt cctaggccgt taattcacgg aagaagtgac   2820
tggagtcttt tctttcatgt cttctgggca actactcagc cctgtggtgg acttggctta   2880
tgcaagacgg tcgaaaacct tggaatcagg agactcggtt ttctttctgg ttctgccatt   2940
ggttggctgt gcgaccgtgg gcaagtgtct ctccttccct gggccatagt cttctctgct   3000
ataaagaccc ttgcagctct cgtgttctgt gaacacttcc ctgtgattct ctgtgagggg   3060
ggatgttgag aggggaagga ggcagagctg gagcagctga gccacagggg aggtggaggg   3120
ggacaggaag gcaggcagaa gctgggtgct ccatcagtcc tcactgatca cgtcagactc   3180
caggaccgag agccacaatg cttcaggaaa gctcaatgaa cccaacagcc acattttcct   3240
tccctaagca tagacaatgg catttgccaa taaccaaaaa gaatgcagag actaactggt   3300
ggtagctttt gcctggcatt caaaaactgg gccagagcaa gtggaaaatg ccagagattg   3360
ttaaactttt caccctgacc agcaccccac gcagctcagc agtgactgct gacagcacgg   3420
agtgacctgc agcgcagggg aggagaagaa aaagagaggg atagtgtatg agcaagaaag   3480
acagattcat tcaagggcag tgggaattga ccacagggat tatagtccac gtgatcctgg   3540
gttctaggag gcagggctat attgtggggg gaaaaaatca gttcaaggga agtcgggaga   3600
cctgatttct aatactatat ttttccttta caagctgagt aattctgagc aagtcacaag   3660
gtagtaactg aggctgtaag attacttagt ttctccttat taggaactct ttttctctgt   3720
ggagttagca gcacaagggc aatcccgttt cttttaacag gaagaaaaca ttcctaagag   3780
taaagccaaa cagattcaag cctaggtctt gctgactata tgattggttt tttgaaaaat   3840
catttcagcg atgtttacta tctgattcag aaaatgagac tagtaccctt tggtcagctg   3900
taaacaaaca cccatttgta aatgtctcaa gttcaggctt aactgcagaa ccaatcaaat   3960
aagaatagaa tctttagagc aaactgtgtt tctccactct ggaggtgagt ctgccagggc   4020
```

```
agtttggaaa tatttacttc acaagtattg acactgttgt tggtattaac aacataaagt   4080

tgctcaaagg caatcattat ttcaagtggc ttaaagttac ttctgacagt tttggtatat   4140

ttattggcta ttgccatttg ctttttgttt tttctctttg ggtttattaa tgtaaagcag   4200

ggattattaa cctacagtcc agaaagcctg tgaatttgaa tgaggaaaaa attacatttt   4260

tgtttttacc accttctaac taaatttaac attttattcc attgcgaata gagccataaa   4320

ctcaaagtgg taataacagt acctgtgatt ttgtcattac caatagaaat cacagacatt   4380

ttatactata ttacagttgt tgcagatacg ttgtaagtga aatatttata ctcaaaacta   4440

ctttgaaatt agacctcctg ctggatcttg tttttaacat attaataaaa catgtttaaa   4500

attttgatat tttgataatc atatttcatt atcatttgtt tcctttgtaa tctatatttt   4560

atatatttga aaacatcttt ctgagaagag ttccccagat ttcaccaatg aggttcttgg   4620

catgcacaca cacagagtaa gaactgattt agaggctaac attgacattg gtgcctgaga   4680

tgcaagactg aaattagaaa gttctcccaa agatacacag ttgttttaaa gctaggggtg   4740

agggggggaaa tctgccgctt ctataggaat gctctccctg gagcctggta gggtgctgtc   4800

cttgtgttct ggctggctgt tatttttctc tgtccctgct acgtcttaaa ggacttgttt   4860

ggatctccag ttcctagcat agtgcctggc acagtgcagg ttctcaatga gtttgcagag   4920

tgaatggaaa tataaactag aaatatatcc ttgttgaaat cagcacacca gtagtcctgg   4980

tgtaagtgtg tgtacgtgtg tgtgtgtgtg tgtgtgtgtg tgtaaaacca ggtggagata   5040

taggaactat tattggggta tgggtgcata aattgggatg ttctttttaa aaagaaactc   5100

caaacagact tctggaaggt tattttctaa gaatcttgct ggcagcgtga aggcaacccc   5160

cctgtgcaca gccccaccca gcctcacgtg gccacctctg tcttccccca tgaagggctg   5220

gctccccagt atatataaac ctctctggag ctcgggcatg agccagcaag gccacccatc   5280

caggcacctc tcagcacagc                                               5300
```

<210> SEQ ID NO 2
<211> LENGTH: 5304
<212> TYPE: DNA
<213> ORGANISM: Homo sapiens

<400> SEQUENCE: 2

```
atctttgttc agtttacctc agggctatta tgaaatgaaa tgagataacc aatgtgaaag     60

tcctataaac tgtatagcct ccattcggat gtatgtcttt ggcaggatga taaagaatca    120

ggaagaagga gtatccacgt tagccaagtg tccaggctgt gtctgctctt attttagtga    180

cagatgttgc tcctgacaga agctattctt caggaaacat cacatccaat atggtaaatc    240

catcaaacag gagctaagaa acaggaatga gatgggcact tgcccaagga aaaatgccag    300

gagagcaaat aatgatgaaa aataaacttt tccctttgtt tttaatttca ggaaaaaatg    360

atgaggacca aaatcaatga ataaggaaaa cagctcagaa aaaagatgtt tccaaattgg    420

taattaagta tttgttcctt gggaagagac ctccatgtga gcttgatggg aaaatgggaa    480

aaacgtcaaa agcatgatct gatcagatcc caaagtggat tattatttta aaaaccagat    540

ggcatcactc tggggaggca agttcaggaa ggtcatgtta gcaaaggaca taacaataac    600

agcaaaatca aaattccgca aatgcaggag gaaaatgggg actgggaaag ctttcataac    660

agtgattagg cagttgacca tgttcgcaac acctccccgt ctataccagg gaacacaaaa    720

attgactggg ctaagcctgg actttcaagg gaaatatgaa aaactgagag caaaacaaaa    780
```

-continued

```
gacatggtta aaaggcaacc agaacattgt gagccttcaa agcagcagtg cccctcagca    840
gggaccctga ggcatttgcc tttaggaagg ccagttttct taaggaatct taagaaactc    900
ttgaaagatc atgaatttta accattttaa gtataaaaca aatatgcgat gcataatcag    960
tttagacatg ggtcccaatt ttataaagtc aggcatacaa ggataacgtg tcccagctcc   1020
ggataggtca gaaatcatta gaaatcactg tgtccccatc ctaacttttt cagaatgatc   1080
tgtcatagcc ctcacacaca ggcccgatgt gtctgaccta caaccacatc tacaacccaa   1140
gtgcctcaac cattgttaac gtgtcatctc agtaggtccc attacaaatg ccacctcccc   1200
tgtgcagccc atcccgctcc acaggaagtc tccccactct agacttctgc atcacgatgt   1260
tacagccaga agctccgtga gggtgagggt ctgtgtctta cacctacctg tatgctctac   1320
acctgagctc actgcaacct ctgcctccca ggttcaagca attctcctgt ctcagcctcc   1380
cgcgtagctg ggactacagg cgcacgcccg gctaattttt gtattgttag tagagatggg   1440
gtttcaccat attagcccgg ctggtcttga actcctgacc tcaggtgatc cacccacctc   1500
agcctcctaa agtgctggga ttacaggcat gagtcaccgc gcccggccaa gggtcagtgt   1560
ttaataagga ataacttgaa tggtttacta aaccaacagg gaaacagaca aaagctgtga   1620
taatttcagg gattcttggg atggggaatg gtgccatgag ctgcctgcct agtcccagac   1680
cactggtcct catcactttc ttccctcatc ctcattttca ggctaagtta ccattttatt   1740
caccatgctt ttgtggtaag cctccacatc gttactgaaa taagagtata cataaactag   1800
ttccatttgg ggccatctgt gtgtgtgtat aggggaggag ggcatacccc agagactcct   1860
tgaagccccc ggcagaggtt tcctctccag ctgggggagc cctgcaagca cccggggtcc   1920
tgggtgtcct gagcaacctg ccagcccgtg ccactggttg ttttgttatc actctctagg   1980
gacctgttgc tttctatttc tgtgtgactc gttcattcat ccaggcattc attgacaatt   2040
tattgagtac ttatatctgc cagacaccag agacaaaatg gtgagcaaag cagtcactgc   2100
cctaccttcg tggaggtgac agtttctcat ggaagacgtg cagaagaaaa ttaatagcca   2160
gccaacttaa acccagtgct gaaagaaagg aaataaacac catcttgaag aattgtgcgc   2220
agcatccctt aacaaggcca cctccctagc gccccctgct gcctccatcg tgcccggagg   2280
cccccaagcc cgagtcttcc aagcctcctc ctccatcagt cacagcgctg cagctggcct   2340
gcctcgcttc ccgtgaatcg tcctggtgca tctgagctgg agactccttg gctccaggct   2400
ccagaaagga aatggagagg gaaactagtc taacggagaa tctggagggg acagtgtttc   2460
ctcagaggga aaggggcctc cacgtccagg agaattccag gaggtgggga ctgcagggag   2520
tggggacgct ggggctgagc gggtgctgaa aggcaggaag gtgaaaaggg caaggctgaa   2580
gctgcccaga tgttcagtgt tgttcacggg gctgggagtt ttccgttgct tcctgtgagc   2640
ctttttatct tttctctgct tggaggagaa gaagtctatt tcatgaaggg atgcagtttc   2700
ataaagtcag ctgttaaaat tccagggtgt gcatgggttt tccttcacga aggcctttat   2760
ttaatgggaa tataggaagc gagctcattt cctaggccgt taattcacgg aagaagtgac   2820
tggagtcttt tctttcatgt cttctgggca actactcagc cctgtggtgg acttggctta   2880
tgcaagacgg tcgaaaacct tggaatcagg agactcggtt ttctttctgg ttctgccatt   2940
ggttggctgt gcgaccgtgg gcaagtgtct ctccttccct gggccatagt cttctctgct   3000
ataaagaccc ttgcagctct cgtgttctgt gaacacttcc ctgtgattct ctgtgagggg   3060
ggatgttgag aggggaagga ggcagagctg gagcagctga gccacagggg aggtggaggg   3120
ggacaggaag gcaggcagaa gctgggtgct ccatcagtcc tcactgatca cgtcagactc   3180
```

-continued

```
caggaccgag agccacaatg cttcaggaaa gctcaatgaa cccaacagcc acattttcct   3240
tccctaagca tagacaatgg catttgccaa taaccaaaaa gaatgcagag actaactggt   3300
ggtagctttt gcctggcatt caaaaactgg gccagagcaa gtggaaaatg ccagagattg   3360
ttaaactttt caccctgacc agcaccccac gcagctcagc agtgactgct gacagcacgg   3420
agtgacctgc agcgcagggg aggagaagaa aaagagaggg atagtgtatg agcaagaaag   3480
acagattcat tcaagggcag tgggaattga ccacagggat tatagtccac gtgatcctgg   3540
gttctaggag gcagggctat attgtggggg gaaaaaatca gttcaaggga agtcgggaga   3600
cctgatttct aatactatat ttttccttta caagctgagt aattctgagc aagtcacaag   3660
gtagtaactg aggctgtaag attacttagt ttctccttat taggaactct ttttctctgt   3720
ggagttagca gcacaagggc aatcccgttt cttttaacag gaagaaaaca ttcctaagag   3780
taaagccaaa cagattcaag cctaggtctt gctgactata tgattggttt tttgaaaaat   3840
catttcagcg atgtttacta tctgattcag aaaatgagac tagtaccctt tggtcagctg   3900
taaacaaaca cccatttgta aatgtctcaa gttcaggctt aactgcagaa ccaatcaaat   3960
aagaatagaa tctttagagc aaactgtgtt tctccactct ggaggtgagt ctgccagggc   4020
agtttggaaa tatttacttc acaagtattg acactgttgt tggtattaac aacataaagt   4080
tgctcaaagg caatcattat ttcaagtggc ttaaagttac ttctgacagt tttggtatat   4140
ttattggcta ttgccatttg ctttttgttt tttctctttg ggtttattaa tgtaaagcag   4200
ggattattaa cctacagtcc agaaagcctg tgaatttgaa tgaggaaaaa attacgtttt   4260
tatttttacc accttctaac taaatttaac attttattcc attgcgaata gagccataaa   4320
ctcaaagtgg taataagagt acctgtgatt ttgtcattac caatagaaat cacagacatt   4380
ttatactata ttacagttgt tgcaggtacg ttgtaagtga aatatttata ctcaaaacta   4440
ctttgaaatt agacctcctg ctggatcttg tttttaacat attaataaaa catgtttaaa   4500
attttgatat tttgataatc atatttcatt atcatttgtt tcctttgtaa tctatatttt   4560
atatatttga aaacatcttt ctgagaagag ttccccagat ttcaccaatg aggttcttgg   4620
catgcacaca cacagagtaa gaactgattt agaggctaac attgacattg gtgcctgaga   4680
tgcaagactg aaattagaaa gttctcccaa agatacacag ttgttttaaa gctaggggtg   4740
aggggggaaa tctgccgctt ctataggaat gctctccctg gagcctggta gggtgctgtc   4800
cttgtgttct ggctggctgt tatttttctc tgtccctgct acgtcttaaa ggacttgttt   4860
ggatctccag ttcctagcat agtgcctggc acagtgcagg ttctcaatga gtttgcagag   4920
tgaatggaaa tataaactag aaatatatct ttgttgaaat cagcacacca gtagtcctgg   4980
tgtaagtgtg tgtacgtgtg tgtgtgtgtg tgtgtgtgtg tgtgtgtaaa accaggtgga   5040
gatataggaa ctattattgg ggtatgggtg cataaattgg gatgttcttt ttaaaaagaa   5100
actccaaaca gacttctgga aggttatttt ctaagaatct tgctggcagc gtgaaggcaa   5160
ccccctgtg cacagcccca cccagcctca cgtggccacc tctgtcttcc cccatgaagg    5220
gctggctccc cagtatatat aaacctctct ggagctcggg catgagccag caaggccacc   5280
catccaggca cctctcagca cagc                                          5304
```

<210> SEQ ID NO 3
<211> LENGTH: 6169
<212> TYPE: DNA
<213> ORGANISM: Homo sapiens

<400> SEQUENCE: 3

```
atctttgttc agtttacctc agggctatta tgaaatgaaa tgagataacc aatgtgaaag     60
tcctataaac tgtatagcct ccattcggat gtatgtcttt ggcaggatga taaagaatca    120
ggaagaagga gtatccacgt tagccaagtg tccaggctgt gtctgctctt attttagtga    180
cagatgttgc tcctgacaga agctattctt caggaaacat cacatccaat atggtaaatc    240
catcaaacag gagctaagaa acaggaatga gatgggcact tgcccaagga aaaatgccag    300
gagagcaaat aatgatgaaa aataaacttt tccctttgtt tttaatttca ggaaaaaatg    360
atgaggacca aaatcaatga ataaggaaaa cagctcagaa aaaagatgtt tccaaattgg    420
taattaagta tttgttcctt gggaagagac ctccatgtga gcttgatggg aaaatgggaa    480
aaacgtcaaa agcatgatct gatcagatcc caaagtggat tattatttta aaaaccagat    540
ggcatcactc tggggaggca agttcaggaa ggtcatgtta gcaaaggaca taacaataac    600
agcaaaatca aaattccgca aatgcaggag gaaaatgggg actgggaaag ctttcataac    660
agtgattagg cagttgacca tgttcgcaac acctccccgt ctataccagg gaacacaaaa    720
attgactggg ctaagcctgg actttcaagg gaaatatgaa aaactgagag caaaacaaaa    780
gacatggtta aaaggcaacc agaacattgt gagccttcaa agcagcagtg cccctcagca    840
gggaccctga ggcatttgcc tttaggaagg ccagttttct taaggaatct taagaaactc    900
ttgaaagatc atgaatttta accattttaa gtataaaaca aatatgcgat gcataatcag    960
tttagacatg ggtcccaatt ttataaagtc aggcatacaa ggataacgtg tcccagctcc   1020
ggataggtca gaaatcatta gaaatcactg tgtccccatc ctaacttttt cagaatgatc   1080
tgtcatagcc ctcacacaca ggcccgatgt gtctgaccta caaccacatc tacaacccaa   1140
gtgcctcaac cattgttaac gtgtcatctc agtaggtccc attacaaatg ccacctcccc   1200
tgtgcagccc atcccgctcc acaggaagtc tccccactct agacttctgc atcacgatgt   1260
tacagccaga agctccgtga gggtgagggt ctgtgtctta cacctacctg tatgctctac   1320
acctgagctc actgcaacct ctgcctccca ggttcaagca attctcctgt ctcagcctcc   1380
cgcgtagctg ggactacagg cgcacgcccg gctaattttt gtattgttag tagagatggg   1440
gtttcaccat attagcccgg ctggtcttga actcctgacc tcaggtgatc cacccacctc   1500
agcctcctaa agtgctggga ttacaggcat gagtcaccgc gcccggccaa gggtcagtgt   1560
ttaataagga ataacttgaa tggtttacta aaccaacagg gaaacagaca aaagctgtga   1620
taatttcagg gattcttggg atggggaatg gtgccatgag ctgcctgcct agtcccagac   1680
cactggtcct catcactttc ttccctcatc ctcattttca ggctaagtta ccattttatt   1740
caccatgctt ttgtggtaag cctccacatc gttactgaaa taagagtata cataaactag   1800
ttccatttgg ggccatctgt gtgtgtgtat aggggaggag ggcatacccc agagactcct   1860
tgaagccccc ggcagaggtt tcctctccag ctgggggagc cctgcaagca cccggggtcc   1920
tgggtgtcct gagcaacctg ccagcccgtg ccactggttg ttttgttatc actctctagg   1980
gacctgttgc tttctatttc tgtgtgactc gttcattcat ccaggcattc attgacaatt   2040
tattgagtac ttatatctgc cagacaccag agacaaaatg gtgagcaaag cagtcactgc   2100
cctaccttcg tggaggtgac agtttctcat ggaagacgtg cagaagaaaa ttaatagcca   2160
gccaacttaa acccagtgct gaaagaaagg aaataaacac catcttgaag aattgtgcgc   2220
agcatccctt aacaaggcca cctccctagc gccccctgct gcctccatcg tgcccggagg   2280
cccccaagcc cgagtcttcc aagcctcctc ctccatcagt cacagcgctg cagctggcct   2340
```

-continued

```
gcctcgcttc ccgtgaatcg tcctggtgca tctgagctgg agactccttg gctccaggct   2400
ccagaaagga aatggagagg gaaactagtc taacggagaa tctggagggg acagtgtttc   2460
ctcagaggga aaggggcctc cacgtccagg agaattccag gaggtgggga ctgcagggag   2520
tggggacgct ggggctgagc gggtgctgaa aggcaggaag gtgaaaaggg caaggctgaa   2580
gctgcccaga tgttcagtgt tgttcacggg gctgggagtt ttccgttgct tcctgtgagc   2640
ctttttatct tttctctgct tggaggagaa gaagtctatt tcatgaaggg atgcagtttc   2700
ataaagtcag ctgttaaaat tccagggtgt gcatgggttt tccttcacga aggcctttat   2760
ttaatgggaa tataggaagc gagctcattt cctaggccgt taattcacgg aagaagtgac   2820
tggagtcttt tctttcatgt cttctgggca actactcagc cctgtggtgg acttggctta   2880
tgcaagacgg tcgaaaacct tggaatcagg agactcggtt ttctttctgg ttctgccatt   2940
ggttggctgt gcgaccgtgg gcaagtgtct ctccttccct gggccatagt cttctctgct   3000
ataaagaccc ttgcagctct cgtgttctgt gaacacttcc ctgtgattct ctgtgagggg   3060
ggatgttgag aggggaagga ggcagagctg gagcagctga gccacagggg aggtggaggg   3120
ggacaggaag gcaggcagaa gctgggtgct ccatcagtcc tcactgatca cgtcagactc   3180
caggaccgag agccacaatg cttcaggaaa gctcaatgaa cccaacagcc acattttcct   3240
tccctaagca tagacaatgg catttgccaa taaccaaaaa gaatgcagag actaactggt   3300
ggtagctttt gcctggcatt caaaaactgg gccagagcaa gtggaaaatg ccagagattg   3360
ttaaactttt caccctgacc agcaccccac gcagctcagc agtgactgct gacagcacgg   3420
agtgacctgc agcgcagggg aggagaagaa aaagagaggg atagtgtatg agcaagaaag   3480
acagattcat tcaagggcag tgggaattga ccacagggat tatagtccac gtgatcctgg   3540
gttctaggag gcagggctat attgtggggg gaaaaaatca gttcaaggga agtcgggaga   3600
cctgatttct aatactatat ttttccttta caagctgagt aattctgagc aagtcacaag   3660
gtagtaactg aggctgtaag attacttagt ttctccttat taggaactct ttttctctgt   3720
ggagttagca gcacaagggc aatcccgttt cttttaacag gaagaaaaca ttcctaagag   3780
taaagccaaa cagattcaag cctaggtctt gctgactata tgattggttt tttgaaaaat   3840
catttcagcg atgtttacta tctgattcag aaaatgagac tagtaccctt tggtcagctg   3900
taaacaaaca cccagttgta aatgtctcaa gttcaggctt aactgcagaa ccaatcaaaa   3960
agaatagaat ctttagagca aactgtgttt ctccacatct ggaggtgagt ctgccagggc   4020
agtttggaaa tatttacttc acaagtattg acactgttgt tggtattaac aacataaagt   4080
tgctcaaagg caatcattat ttcaagtggc ttaaagttac ttctgacagt tttggtatat   4140
ttattggcta ttgccatttg ctttttgttt tttctctttg ggtttattaa tgtaaagcag   4200
ggattattaa cctacagtcc agaaagcctg tgaatttgaa tgaggaaaaa attacatttt   4260
tgtttttacc accttctaac taaatttaac attttattcc attgcgaata gagccataaa   4320
ctcaaagtgg taataacagt acctgtgatt ttgtcattac caatagaaat cacagacatt   4380
ttatactata ttacagttgt tgcagatacg ttgtaagtga aatatttata ctcaaaacta   4440
ctttgaaatt agacctcctg ctggatcttg tttttaacat attaataaaa catgtttaaa   4500
attttgatat tttgataatc atatttcatt atcatttgtt tcctttgtaa tctatatttt   4560
atatatttga aaacatcttt ctgagaagag ttccccagat ttcaccaatg aggttcttgg   4620
catgcacaca cacagagtaa gaactgattt agaggctaac attgacattg gtgcctgaga   4680
```

-continued

```
tgcaagactg aaattagaaa gttctcccaa agatacacag ttgttttaaa gctaggggtg   4740

agggggggaaa tctgccgctt ctataggaat gctctccctg gagcctggta gggtgctgtc   4800

cttgtgttct ggctggctgt tatttttctc tgtccctgct acgtcttaaa ggacttgttt   4860

ggatctccag ttcctagcat agtgcctggc acagtgcagg ttctcaatga gtttgcagag   4920

tgaatggaaa tataaactag aaatatatcc ttgttgaaat cagcacacca gtagtcctgg   4980

tgtaagtgtg tgtacgtgtg tgtgtgtgtg tgtgtgtgtg tgtaaaacca ggtggagata   5040

taggaactat tattggggta tgggtgcata aattgggatg ttctttttaa aaagaaactc   5100

caaacagact tctggaaggt tattttctaa gaatcttgct ggcagcgtga aggcaacccc   5160

cctgtgcaca gccccaccca gcctcacgtg gccacctctg tcttccccca tgaagggctg   5220

gctccccagt atatataaac ctctctggag ctcgggcatg agccagcaag gccacccatc   5280

caggcacctc tcagcacagc agagctttcc agaggaagcc tcaccaagcc tctgcaatga   5340

ggttcttctg tgcacgttgc tgcagctttg ggcctgagat gccagctgtc cagctgctgc   5400

ttctggcctg cctggtgtgg gatgtggggg ccaggacagc tcagctcagg aaggccaatg   5460

accagagtgg ccgatgccag tataccttca gtgtggccag tcccaatgaa tccagctgcc   5520

cagagcagag ccaggccatg tcagtcatcc ataacttaca gagagacagc agcacccaac   5580

gcttagacct ggaggccacc aaagctcgac tcagctccct ggagagcctc ctccaccaat   5640

tgaccttgga ccaggctgcc aggccccagg agacccagga ggggctgcag agggagctgg   5700

gcaccctgag gcgggagcgg gaccagctgg aaacccaaac cagagagttg gagactgcct   5760

acagcaacct cctccgagac aagtcagttc tggaggaaga gaagaagcga ctaaggcaag   5820

aaaatgagaa tctggccagg aggttggaaa gcagcagcca ggaggtagca aggctgagaa   5880

ggggccagtg tccccagacc cgagacactg ctcgggctgt gccaccaggc tccagagaag   5940

gtaagaatgc agagtggggg gactctgagt tcagcaggtg atatggctcg tagtgacctg   6000

ctacaggcgc tccaggcctc cctgcccttt ctcctagaga ctgcacagct agcacaagac   6060

agatgaatta aggaaagcac acgatcacct tcaagtatta ctagtaattt agctcctgag   6120

agcttcattt agattagtgg ttcagagttc ttgtgcccct ccatgtcag               6169
```

<210> SEQ ID NO 4
<211> LENGTH: 926
<212> TYPE: DNA
<213> ORGANISM: Homo sapiens

<400> SEQUENCE: 4

```
aaggtaggca cattgccctg caatttataa tttatgaggt gttcaattat ggaattgtca     60

aatattaaca aaagtagaga gactacaatg aactccaatg tagccataac tcaggcccaa    120

ctgttatcag cacagtccaa tcatgtttta tctttccttc tctgaccccc aacccatccc    180

cagtccttat ctaaaatcaa atatcaaaca ccatactctt tgggagccta tttatttagt    240

tagttagttt tcagacagag tttctttctt gttcccaagc tggagtacaa tagtgtagtc    300

tcggctaaca gcaatctccc cctccttggt tcaagcaatt ctcctgcctc agtctcccaa    360

gaagctggga ttatagacac ctgccaccac atccagctaa tttttttgtg ttttagaaaa    420

gacagggttt caccatgttg gccaggctgg tttcgaactc ctgacctcag gtgatccgcc    480

tgcctcggcc tcccaaagtg ctgggattac aggcatgagc caccacgcct ggccggcagc    540

ctatttaaat gtcatcctca acatagtcaa tccttgggcc attttttctt acagtaaaat    600

tttgtctctt tcttttaatc agtttctacg tggaatttgg acactttggc cttccaggaa    660
```

-continued

```
ctgaagtccg agctaactga agttcctgct tcccgaattt tgaaggagag cccatctggc    720

tatctcagga gtggagaggg agacaccggt atgaagttaa gtttcttccc ttttgtgccc    780

acgtggtctt tattcatgtc tagtgctgtg ttcagagaat cagtataggg taaatgccca    840

cccaaggggg aaattaactt ccctgggagc agagggaggg gaggagaaga ggaacagaac    900

tctctctctc tctctgttac ccttgt                                         926
```

<210> SEQ ID NO 5
<211> LENGTH: 2099
<212> TYPE: DNA
<213> ORGANISM: Homo sapiens

<400> SEQUENCE: 5

```
tggctctgcc aagcttccgc atgatcattg tctgtgtttg gaagattatg gattaagtgg     60

tgcttcgttt tctttctgaa tttaccagga tgtggagaac tagtttgggt aggagagcct    120

ctcacgctga gaacagcaga aacaattact ggcaagtatg gtgtgtggat gcgagacccc    180

aagcccacct accctacac ccaggagacc acgtggagaa tcgacacagt tggcacggat    240

gtccgccagg tttttgagta tgacctcatc agccagttta tgcagggcta cccttctaag    300

gttcacatac tgcctaggcc actggaaagc acgggtgctg tggtgtactc ggggagcctc    360

tatttccagg gcgctgagtc cagaactgtc ataagatatg agctgaatac cgagacagtg    420

aaggctgaga aggaaatccc tggagctggc taccacggac agttcccgta ttcttggggt    480

ggctacacgg acattgactt ggctgtggat gaagcaggcc tctgggtcat ttacagcacc    540

gatgaggcca aaggtgccat tgtcctctcc aaactgaacc cagagaatct ggaactcgaa    600

caaacctggg agacaaacat ccgtaagcag tcagtcgcca atgccttcat catctgtggc    660

accttgtaca ccgtcagcag ctacacctca gcagatgcta ccgtcaactt tgcttatgac    720

acaggcacag gtatcagcaa gaccctgacc atcccattca agaaccgcta taagtacagc    780

agcatgattg actacaaccc cctggagaag aagctctttg cctgggacaa cttgaacatg    840

gtcacttatg acatcaagct ctccaagatg tgaaaagcct ccaagctgta caggcaatgg    900

cagaaggaga tgctcagggc tcctgggggg agcaggctga agggagagcc agccagccag    960

ggcccaggca gctttgactg ctttccaagt tttcattaat ccagaaggat gaacatggtc   1020

accatctaac tattcaggaa ttgtagtctg agggcgtaga caatttcata taataaatat   1080

cctttatctt ctgtcagcat ttatgggatg tttaatgaca tagttcaagt tttcttgtga   1140

tttggggcaa aagctgtaag gcataatagt cttttcctga aaaccattgc tcttgcatgt   1200

tacatggtta ccacaagcca caataaaaag cataacttct aaaggaagca gaatagctcc   1260

tctggccagc atcgaatata agtaagatgc atttactaca gttggcttct aatgcttcag   1320

atagaataca gttgggtctc acataaccct tacattgtga aataaaattt tcttacccaa   1380

cgttctcttc cttgaacttt gtgggaatct ttgcttaaga gaaggatata gattccaacc   1440

atcaggtaat tccttcaggt tgggagatgt gattgcagga tgttaaaggt gtgtgtgtgt   1500

gtgtgtgtgt gtgtgtaact gagaggcttg tgcctggttt tgaggtgctg cccaggatga   1560

cgccaagcaa atagcgcatc cacactttcc cacctccatc tcctggtgct ctcggcacta   1620

ccggagcaat ctttccatct ctcccctgaa cccaccctct attcacccta actccacttc   1680

agtttgcttt tgattttttt tttttttttt tttttttttt gagatggggt ctcgctctgt   1740

cacccaggct ggagtgcagt ggcacgatct cggctcactg caagttccgc ctcccaggtt   1800
```

-continued

```
cacaccattc tcctgcctca gcctcccaag tagctgggac tacaggcacc tgccaccacg   1860

cctggctaat tttttttttt tccagtgaag atgggtttca ccatgttagc caggatggtc   1920

tcgatctcct gaccttgtca tccacccacc ttggcctccc aaagtgctgg gattacaggc   1980

gtgagccacc acgcccagcc cctccacttc agtttttatc tgtcatcagg ggtatgaatt   2040

ttataagcca cacctcaggt ggagaaagct tgatgcatag cttgagtatt ctatactgt    2099


<210> SEQ ID NO 6
<211> LENGTH: 19
<212> TYPE: DNA
<213> ORGANISM: Homo sapiens

<400> SEQUENCE: 6

tgaggcttcc tctggaaac                                                  19


<210> SEQ ID NO 7
<211> LENGTH: 20
<212> TYPE: DNA
<213> ORGANISM: Homo sapiens

<400> SEQUENCE: 7

tgaaatcagc acaccagtag                                                 20


<210> SEQ ID NO 8
<211> LENGTH: 21
<212> TYPE: DNA
<213> ORGANISM: Homo sapiens

<400> SEQUENCE: 8

gcacccatac cccaataata g                                               21


<210> SEQ ID NO 9
<211> LENGTH: 20
<212> TYPE: DNA
<213> ORGANISM: Homo sapiens

<400> SEQUENCE: 9

agagttcccc agatttcacc                                                 20


<210> SEQ ID NO 10
<211> LENGTH: 20
<212> TYPE: DNA
<213> ORGANISM: Homo sapiens

<400> SEQUENCE: 10

atctggggaa ctcttctcag                                                 20


<210> SEQ ID NO 11
<211> LENGTH: 19
<212> TYPE: DNA
<213> ORGANISM: Homo sapiens

<400> SEQUENCE: 11

tacagttgtt gcagatacg                                                  19


<210> SEQ ID NO 12
<211> LENGTH: 21
<212> TYPE: DNA
<213> ORGANISM: Homo sapiens

<400> SEQUENCE: 12

acaacgtatc tgcaacaact g                                               21
```

<210> SEQ ID NO 13
<211> LENGTH: 20
<212> TYPE: DNA
<213> ORGANISM: Homo sapiens

<400> SEQUENCE: 13
tcaggcttaa ctgcagaacc 20

<210> SEQ ID NO 14
<211> LENGTH: 19
<212> TYPE: DNA
<213> ORGANISM: Homo sapiens

<400> SEQUENCE: 14
ttggttctgc agttaagcc 19

<210> SEQ ID NO 15
<211> LENGTH: 19
<212> TYPE: DNA
<213> ORGANISM: Homo sapiens

<400> SEQUENCE: 15
agcagcacaa gggcaatcc 19

<210> SEQ ID NO 16
<211> LENGTH: 18
<212> TYPE: DNA
<213> ORGANISM: Homo sapiens

<400> SEQUENCE: 16
acagggctat attgtggg 18

<210> SEQ ID NO 17
<211> LENGTH: 19
<212> TYPE: DNA
<213> ORGANISM: Homo sapiens

<400> SEQUENCE: 17
cctgagatgc cagctgtcc 19

<210> SEQ ID NO 18
<211> LENGTH: 20
<212> TYPE: DNA
<213> ORGANISM: Homo sapiens

<400> SEQUENCE: 18
ctgaagcatt agaagccaac 20

<210> SEQ ID NO 19
<211> LENGTH: 20
<212> TYPE: DNA
<213> ORGANISM: Homo sapiens

<400> SEQUENCE: 19
accttggacc aggctgccag 20

<210> SEQ ID NO 20
<211> LENGTH: 19
<212> TYPE: DNA
<213> ORGANISM: Homo sapiens

<400> SEQUENCE: 20

-continued

```
aggtttgttc gagttccag                                                19


<210> SEQ ID NO 21
<211> LENGTH: 20
<212> TYPE: DNA
<213> ORGANISM: Homo sapiens

<400> SEQUENCE: 21

acaattactg gcaagtatgg                                               20


<210> SEQ ID NO 22
<211> LENGTH: 19
<212> TYPE: DNA
<213> ORGANISM: Homo sapiens

<400> SEQUENCE: 22

ccttctcagc cttgctacc                                                19


<210> SEQ ID NO 23
<211> LENGTH: 20
<212> TYPE: DNA
<213> ORGANISM: Homo sapiens

<400> SEQUENCE: 23

acacctcagc agatgctacc                                               20


<210> SEQ ID NO 24
<211> LENGTH: 19
<212> TYPE: DNA
<213> ORGANISM: Homo sapiens

<400> SEQUENCE: 24

atggatgact gacatggcc                                                19


<210> SEQ ID NO 25
<211> LENGTH: 19
<212> TYPE: DNA
<213> ORGANISM: Homo sapiens

<400> SEQUENCE: 25

aaggatgaac atggtcacc                                                19


<210> SEQ ID NO 26
<211> LENGTH: 1548
<212> TYPE: DNA
<213> ORGANISM: Homo sapiens

<400> SEQUENCE: 26

agagctttcc agaggaagcc tcaccaagcc tctgcaatga ggttcttctg tgcacgttgc      60

tgcagctttg ggcctgagat gccagctgtc cagctgctgc ttctggcctg cctggtgtgg     120

gatgtggggg ccaggacagc tcagctcagg aaggccaatg accagagtgg ccgatgccag     180

tataccttca gtgtggccag tcccaatgaa tccagctgcc cagagcagag ccaggccatg     240

tcagtcatcc ataacttaca gagagacagc agcacccaac gcttagacct ggaggccacc     300

aaagctcgac tcagctccct ggagagcctc ctccaccaat tgaccttgga ccaggctgcc     360

aggccccagg agacccagga ggggctgcag agggagctgg gcaccctgag gcgggagcgg     420

gaccagctgg aaacccaaac cagagagttg gagactgcct acagcaacct cctccgagac     480

aagtcagttc tggaggaaga gaagaagcga ctaaggcaag aaaatgagaa tctggccagg     540

aggttggaaa gcagcagcca ggaggtagca aggctgagaa ggggccagtg tccccagacc     600
```

-continued

```
cgagacactg ctcgggctgt gccaccaggc tccagagaag tttctacgtg gaatttggac     660

actttggcct tccaggaact gaagtccgag ctaactgaag ttcctgcttc ccgaattttg     720

aaggagagcc catctggcta tctcaggagt ggagagggag acaccggatg tggagaacta     780

gtttgggtag gagagcctct cacgctgaga acagcagaaa caattactgg caagtatggt     840

gtgtggatgc gagaccccaa gcccacctac ccctacaccc aggagaccac gtggagaatc     900

gacacagttg gcacggatgt ccgccaggtt tttgagtatg acctcatcag ccagtttatg     960

cagggctacc cttctaaggt tcacatactg cctaggccac tggaaagcac gggtgctgtg    1020

gtgtactcgg ggagcctcta tttccagggc gctgagtcca gaactgtcat aagatatgag    1080

ctgaataccg agacagtgaa ggctgagaag gaaatccctg gagctggcta ccacggacag    1140

ttcccgtatt cttggggtgg ctacacggac attgacttgg ctgtggatga agcaggcctc    1200

tgggtcattt acagcaccga tgaggccaaa ggtgccattg tcctctccaa actgaaccca    1260

gagaatctgg aactcgaaca aacctgggag acaaacatcc gtaagcagtc agtcgccaat    1320

gccttcatca tctgtggcac cttgtacacc gtcagcagct acacctcagc agatgctacc    1380

gtcaactttg cttatgacac aggcacaggt atcagcaaga ccctgaccat cccattcaag    1440

aaccgctata agtacagcag catgattgac tacaaccccc tggagaagaa gctctttgcc    1500

tgggacaact tgaacatggt cacttatgac atcaagctct ccaagatg                 1548
```

<210> SEQ ID NO 27
<211> LENGTH: 178
<212> TYPE: PRT
<213> ORGANISM: Homo sapiens

<400> SEQUENCE: 27

```
Thr Gly Ala Val Val Tyr Ser Gly Ser Leu Tyr Phe Gln Gly Ala Glu
 1               5                  10                  15

Ser Arg Thr Val Ile Arg Tyr Glu Leu Asn Thr Glu Thr Val Lys Ala
            20                  25                  30

Glu Lys Glu Ile Pro Gly Ala Gly Tyr His Gly Gln Phe Pro Tyr Ser
        35                  40                  45

Trp Gly Gly Tyr Thr Asp Ile Asp Leu Ala Val Asp Glu Ala Gly Leu
    50                  55                  60

Trp Val Ile Tyr Ser Thr Asp Glu Ala Lys Gly Ala Ile Val Leu Ser
65                  70                  75                  80

Lys Leu Asn Pro Glu Asn Leu Glu Leu Glu Gln Thr Trp Glu Thr Asn
                85                  90                  95

Ile Arg Lys Gln Ser Val Ala Asn Ala Phe Ile Ile Cys Gly Thr Leu
            100                 105                 110

Tyr Thr Val Ser Ser Tyr Thr Ser Ala Asp Ala Thr Val Asn Phe Ala
        115                 120                 125

Tyr Asp Thr Gly Thr Gly Ile Ser Lys Thr Leu Thr Ile Pro Phe Lys
    130                 135                 140

Asn Arg Tyr Lys Tyr Ser Ser Met Ile Asp Tyr Asn Pro Leu Glu Lys
145                 150                 155                 160

Lys Leu Phe Ala Trp Asp Asn Leu Asn Met Val Thr Tyr Asp Ile Lys
                165                 170                 175

Leu Ser
```

<210> SEQ ID NO 28
<211> LENGTH: 131

-continued

<212> TYPE: PRT
<213> ORGANISM: Homo sapiens

<400> SEQUENCE: 28

```
Arg Phe Asp Leu Lys Thr Glu Thr Ile Leu Lys Thr Arg Ser Leu Asp
 1               5                  10                  15

Tyr Ala Gly Tyr Asn Asn Met Tyr His Tyr Ala Trp Gly Gly His Ser
            20                  25                  30

Asp Ile Asp Leu Met Val Asp Glu Ser Gly Leu Trp Ala Val Tyr Ala
        35                  40                  45

Thr Asn Gln Asn Ala Gly Asn Ile Val Val Ser Arg Leu Asp Pro Val
    50                  55                  60

Ser Leu Gln Thr Leu Gln Thr Trp Asn Thr Ser Tyr Pro Lys Arg Xaa
65                  70                  75                  80

Pro Gly Xaa Ala Phe Ile Ile Cys Gly Thr Cys Tyr Val Thr Asn Gly
                85                  90                  95

Tyr Ser Gly Gly Thr Lys Val His Tyr Ala Tyr Gln Thr Asn Ala Ser
            100                 105                 110

Thr Tyr Glu Tyr Ile Asp Ile Pro Phe Gln Asn Lys Leu Xaa Pro His
        115                 120                 125

Phe Pro Cys
    130
```

<210> SEQ ID NO 29
<211> LENGTH: 178
<212> TYPE: PRT
<213> ORGANISM: Rattus norvegicus

<400> SEQUENCE: 29

```
Gly Thr Gly Gln Val Val Tyr Asn Gly Ser Ile Tyr Phe Asn Lys Phe
 1               5                  10                  15

Gln Ser His Ile Ile Ile Arg Phe Asp Leu Lys Thr Glu Thr Ile Leu
            20                  25                  30

Lys Thr Arg Ser Leu Asp Tyr Ala Gly Tyr Asn Asn Met Tyr His Tyr
        35                  40                  45

Ala Trp Gly Gly His Ser Asp Ile Asp Leu Met Val Asp Glu Asn Gly
    50                  55                  60

Leu Trp Ala Val Tyr Ala Thr Asn Gln Asn Ala Gly Asn Ile Val Ile
65                  70                  75                  80

Ser Lys Leu Asp Pro Val Ser Leu Gln Ile Leu Gln Thr Trp Asn Thr
                85                  90                  95

Ser Tyr Pro Lys Arg Ser Ala Gly Glu Ala Phe Ile Ile Cys Gly Thr
            100                 105                 110

Leu Tyr Val Thr Asn Gly Tyr Ser Gly Gly Thr Lys Val His Tyr Ala
        115                 120                 125

Tyr Gln Thr Asn Ala Ser Thr Tyr Glu Tyr Ile Asp Ile Pro Phe Gln
    130                 135                 140

Asn Lys Tyr Ser His Ile Ser Met Leu Asp Tyr Asn Pro Lys Asp Arg
145                 150                 155                 160

Ala Leu Tyr Ala Trp Asn Asn Gly His Gln Thr Leu Tyr Asn Val Thr
                165                 170                 175

Leu Phe
```

<210> SEQ ID NO 30
<211> LENGTH: 177
<212> TYPE: PRT

<213> ORGANISM: Rana catesbeiana

<400> SEQUENCE: 30

```
Gly Ala Gly Val Val Val His Asn Asn Asn Leu Tyr Tyr Asn Cys Phe
 1               5                  10                  15

Asn Ser His Asp Met Cys Arg Ala Ser Leu Thr Ser Gly Val Tyr Gln
            20                  25                  30

Lys Lys Pro Leu Leu Asn Ala Leu Phe Asn Asn Arg Phe Ser Tyr Ala
        35                  40                  45

Gly Thr Met Phe Gln Asp Met Asp Phe Ser Ser Asp Glu Lys Gly Leu
    50                  55                  60

Trp Val Ile Phe Thr Thr Glu Lys Ser Ala Gly Lys Ile Val Val Gly
65                  70                  75                  80

Lys Val Asn Val Ala Thr Phe Thr Val Asp Asn Ile Trp Ile Thr Thr
                85                  90                  95

Gln Asn Lys Ser Asp Ala Ser Asn Ala Phe Met Ile Cys Gly Val Leu
            100                 105                 110

Tyr Val Thr Arg Ser Leu Gly Pro Lys Met Glu Glu Val Phe Tyr Met
        115                 120                 125

Phe Asp Thr Lys Thr Gly Lys Glu Gly His Leu Ser Ile Met Met Glu
    130                 135                 140

Lys Met Ala Glu Lys Val His Ser Leu Ser Tyr Asn Ser Asn Asp Arg
145                 150                 155                 160

Lys Leu Tyr Met Phe Ser Glu Gly Tyr Leu Leu His Tyr Asp Ile Ala
                165                 170                 175

Leu
```

<210> SEQ ID NO 31
<211> LENGTH: 74
<212> TYPE: PRT
<213> ORGANISM: Artificial sequence
<220> FEATURE:
<223> OTHER INFORMATION: Consensus homology of SEQ ID NO: 27, 28, 29 and 30

<400> SEQUENCE: 31

```
Gly Val Val Tyr Ser Arg Leu Thr Glu Thr Leu Ala Gly Tyr Asn Asn
 1               5                  10                  15

Tyr Ala Trp Gly Gly Asp Ile Asp Leu Val Asp Glu Gly Leu Trp Tyr
            20                  25                  30

Thr Ala Gly Ile Val Ser Lys Leu Pro Leu Gln Thr Trp Thr Lys Ala
        35                  40                  45

Phe Ile Ile Cys Gly Thr Leu Tyr Val Thr Tyr Val Tyr Ala Tyr Thr
    50                  55                  60

Ile Tyr Asp Tyr Asn Pro Lys Leu Tyr Leu
65                  70
```

<210> SEQ ID NO 32
<211> LENGTH: 504
<212> TYPE: PRT
<213> ORGANISM: Homo sapiens

<400> SEQUENCE: 32

```
Met Arg Phe Phe Cys Ala Arg Cys Cys Ser Phe Gly Pro Glu Met Pro
 1               5                  10                  15

Ala Val Gln Leu Leu Leu Leu Ala Cys Leu Val Trp Asp Val Gly Ala
            20                  25                  30
```

-continued

```
Arg Thr Ala Gln Leu Arg Lys Ala Asn Asp Gln Ser Gly Arg Cys Gln
        35                  40                  45

Tyr Thr Phe Ser Val Ala Ser Pro Asn Glu Ser Ser Cys Pro Glu Gln
    50                  55                  60

Ser Gln Ala Met Ser Val Ile His Asn Leu Gln Arg Asp Ser Ser Thr
65                  70                  75                  80

Gln Arg Leu Asp Leu Glu Ala Thr Lys Ala Arg Leu Ser Ser Leu Glu
                85                  90                  95

Ser Leu Leu His Gln Leu Thr Leu Asp Gln Ala Ala Arg Pro Gln Glu
            100                 105                 110

Thr Gln Glu Gly Leu Gln Arg Glu Leu Gly Thr Leu Arg Arg Glu Arg
        115                 120                 125

Asp Gln Leu Glu Thr Gln Thr Arg Glu Leu Glu Thr Ala Tyr Ser Asn
    130                 135                 140

Leu Leu Arg Asp Lys Ser Val Leu Glu Glu Glu Lys Lys Arg Leu Arg
145                 150                 155                 160

Gln Glu Asn Glu Asn Leu Ala Arg Arg Leu Glu Ser Ser Ser Gln Glu
                165                 170                 175

Val Ala Arg Leu Arg Arg Gly Gln Cys Pro Gln Thr Arg Asp Thr Ala
            180                 185                 190

Arg Ala Val Pro Pro Gly Ser Arg Glu Val Ser Thr Trp Asn Leu Asp
        195                 200                 205

Thr Leu Ala Phe Gln Glu Leu Lys Ser Glu Leu Thr Glu Val Pro Ala
    210                 215                 220

Ser Arg Ile Leu Lys Glu Ser Pro Ser Gly Tyr Leu Arg Ser Gly Glu
225                 230                 235                 240

Gly Asp Thr Gly Cys Gly Glu Leu Val Trp Val Gly Glu Pro Leu Thr
                245                 250                 255

Leu Arg Thr Ala Glu Thr Ile Thr Gly Lys Tyr Gly Val Trp Met Arg
            260                 265                 270

Asp Pro Lys Pro Thr Tyr Pro Tyr Thr Gln Glu Thr Thr Trp Arg Ile
        275                 280                 285

Asp Thr Val Gly Thr Asp Val Arg Gln Val Phe Glu Tyr Asp Leu Ile
    290                 295                 300

Ser Gln Phe Met Gln Gly Tyr Pro Ser Lys Val His Ile Leu Pro Arg
305                 310                 315                 320

Pro Leu Glu Ser Thr Gly Ala Val Val Tyr Ser Gly Ser Leu Tyr Phe
                325                 330                 335

Gln Gly Ala Glu Ser Arg Thr Val Ile Arg Tyr Glu Leu Asn Thr Glu
            340                 345                 350

Thr Val Lys Ala Glu Lys Glu Ile Pro Gly Ala Gly Tyr His Gly Gln
        355                 360                 365

Phe Pro Tyr Ser Trp Gly Gly Tyr Thr Asp Ile Asp Leu Ala Val Asp
    370                 375                 380

Glu Ala Gly Leu Trp Val Ile Tyr Ser Thr Asp Glu Ala Lys Gly Ala
385                 390                 395                 400

Ile Val Leu Ser Lys Leu Asn Pro Glu Asn Leu Glu Leu Glu Gln Thr
                405                 410                 415

Trp Glu Thr Asn Ile Arg Lys Gln Ser Val Ala Asn Ala Phe Ile Ile
            420                 425                 430

Cys Gly Thr Leu Tyr Thr Val Ser Ser Tyr Thr Ser Ala Asp Ala Thr
        435                 440                 445

Val Asn Phe Ala Tyr Asp Thr Gly Thr Gly Ile Ser Lys Thr Leu Thr
```

```
    450                 455                 460

Ile Pro Phe Lys Asn Arg Tyr Lys Tyr Ser Ser Met Ile Asp Tyr Asn
465                 470                 475                 480

Pro Leu Glu Lys Lys Leu Phe Ala Trp Asp Asn Leu Asn Met Val Thr
                485                 490                 495

Tyr Asp Ile Lys Leu Ser Lys Met
            500


<210> SEQ ID NO 33
<211> LENGTH: 20
<212> TYPE: DNA
<213> ORGANISM: Homo sapiens

<400> SEQUENCE: 33

caaacagact tccggaaggt                                                 20


<210> SEQ ID NO 34
<211> LENGTH: 5271
<212> TYPE: DNA
<213> ORGANISM: Homo sapiens

<400> SEQUENCE: 34

atctttgttc agtttacctc agggctatta tgaaatgaaa tgagataacc aatgtgaaag     60

tcctataaac tgtatagcct ccattcggat gtatgtcttt ggcaggatga taaagaatca    120

ggaagaagga gtatccacgt tagccaagtg tccaggctgt gtctgctctt attttagtga    180

cagatgttgc tcctgacaga agctattctt caggaaacat cacatccaat atggtaaatc    240

catcaaacag gagctaagaa acaggaatga gatgggcact tgcccaagga aaaatgccag    300

gagagcaaat aatgatgaaa aataaacttt tccctttgtt tttaatttca ggaaaaaatg    360

atgaggacca aaatcaatga ataaggaaaa cagctcagaa aaaagatgtt tccaaattgg    420

taattaagta tttgttcctt gggaagagac ctccatgtga gcttgatggg aaaatgggaa    480

aaacgtcaaa agcatgatct gatcagatcc caaagtggat tattatttta aaaaccagat    540

ggcatcactc tggggaggca agttcaggaa ggtcatgtta gcaaaggaca taacaataac    600

agcaaaatca aaattccgca aatgcaggag gaaaatgggg actgggaaag ctttcataac    660

agtgattagg cagttgacca tgttcgcaac acctccccgt ctataccagg gaacacaaaa    720

attgactggg ctaagcctgg actttcaagg gaaatatgaa aaactgagag caaaacaaaa    780

gacatggtta aaaggcaacc agaacattgt gagccttcaa agcagcagtg cccctcagca    840

gggaccctga ggcatttgcc tttaggaagg ccagttttct taaggaatct taagaaactc    900

ttgaaagatc atgaatttta accattttaa gtataaaaca aatatgcgat gcataatcag    960

tttagacatg ggtcccaatt ttataaagtc aggcatacaa ggataacgtg tcccagctcc   1020

ggataggtca gaaatcatta gaaatcactg tgtccccatc ctaacttttt cagaatgatc   1080

tgtcatagcc ctcacacaca ggcccgatgt gtctgaccta caaccacatc tacaacccaa   1140

gtgcctcaac cattgttaac gtgtcatctc agtaggtccc attacaaatg ccacctcccc   1200

tgtgcagccc atcccgctcc acaggaagtc tccccactct agacttctgc atcacgatgt   1260

tacagccaga agctccgtga gggtgagggt ctgtgtctta cacctacctg tatgctctac   1320

acctgagctc actgcaacct ctgcctccca ggttcaagca attctcctgt ctcagcctcc   1380

cgcgtagctg ggactacagg cgcacgcccg gctaattttt gtattgttag tagagatggg   1440

gtttcaccat attagcccgg ctggtcttga actcctgacc tcaggtgatc cacccacctc   1500
```

-continued

```
agcctcctaa agtgctggga ttacaggcat gagtcaccgc gcccggccaa gggtcagtgt   1560
ttaataagga ataacttgaa tggtttacta aaccaacagg gaaacagaca aaagctgtga   1620
taatttcagg gattcttggg atggggaatg gtgccatgag ctgcctgcct agtcccagac   1680
cactggtcct catcactttc ttccctcatc ctcattttca ggctaagtta ccattttatt   1740
caccatgctt ttgtggtaag cctccacatc gttactgaaa taagagtata cataaactag   1800
ttccatttgg ggccatctgt gtgtgtgtat aggggaggag ggcatacccc agagactcct   1860
tgaagccccc ggcagaggtt tcctctccag ctgggggagc cctgcaagca cccggggtcc   1920
tgggtgtcct gagcaacctg ccagcccgtg ccactggttg ttttgttatc actctctagg   1980
gacctgttgc tttctatttc tgtgtgactc gttcattcat ccaggcattc attgacaatt   2040
tattgagtac ttatatctgc cagacaccag agacaaaatg gtgagcaaag cagtcactgc   2100
cctaccttcg tggaggtgac agtttctcat ggaagacgtg cagaagaaaa ttaatagcca   2160
gccaacttaa acccagtgct gaaagaaagg aaataaacac catcttgaag aattgtgcgc   2220
agcatccctt aacaaggcca cctccctagc gccccctgct gcctccatcg tgcccggagg   2280
cccccaagcc cgagtcttcc aagcctcctc ctccatcagt cacagcgctg cagctggcct   2340
gcctcgcttc ccgtgaatcg tcctggtgca tctgagctgg agactccttg gctccaggct   2400
ccagaaagga aatggagagg gaaactagtc taacggagaa tctggagggg acagtgtttc   2460
ctcagaggga aaggggcctc cacgtccagg agaattccag gaggtgggga ctgcagggag   2520
tggggacgct ggggctgagc gggtgctgaa aggcaggaag gtgaaaaggg caaggctgaa   2580
gctgcccaga tgttcagtgt tgttcacggg gctgggagtt ttccgttgct tcctgtgagc   2640
ctttttatct tttctctgct tggaggagaa gaagtctatt tcatgaaggg atgcagtttc   2700
ataaagtcag ctgttaaaat tccagggtgt gcatgggttt tccttcacga aggcctttat   2760
ttaatgggaa tataggaagc gagctcattt cctaggccgt taattcacgg aagaagtgac   2820
tggagtcttt tctttcatgt cttctgggca actactcagc cctgtggtgg acttggctta   2880
tgcaagacgg tcgaaaacct tggaatcagg agactcggtt ttctttctgg ttctgccatt   2940
ggttggctgt gcgaccgtgg gcaagtgtct ctccttccct gggccatagt cttctctgct   3000
ataaagaccc ttgcagctct cgtgttctgt gaacacttcc ctgtgattct ctgtgagggg   3060
ggatgttgag aggggaagga ggcagagctg gagcagctga gccacagggg aggtggaggg   3120
ggacaggaag gcaggcagaa gctgggtgct ccatcagtcc tcactgatca cgtcagactc   3180
caggaccgag agccacaatg cttcaggaaa gctcaatgaa cccaacagcc acattttcct   3240
tccctaagca tagacaatgg catttgccaa taaccaaaaa gaatgcagag actaactggt   3300
ggtagctttt gcctggcatt caaaaactgg gccagagcaa gtggaaaatg ccagagattg   3360
ttaaactttt caccctgacc agcaccccac gcagctcagc agtgactgct gacagcacgg   3420
agtgacctgc agcgcagggg aggagaagaa aaagagaggg atagtgtatg agcaagaaag   3480
acagattcat tcaagggcag tgggaattga ccacagggat tatagtccac gtgatcctgg   3540
gttctaggag gcagggctat attgtggggg gaaaaaatca gttcaaggga agtcgggaga   3600
cctgatttct aatactatat ttttccttta caagctgagt aattctgagc aagtcacaag   3660
gtagtaactg aggctgtaag attacttagt ttctccttat taggaactct ttttctctgt   3720
ggagttagca gcacaagggc aatcccgttt cttttaacag gaagaaaaca ttcctaagag   3780
taaagccaaa cagattcaag cctaggtctt gctgactata tgattggttt tttgaaaaat   3840
catttcagcg atgtttacta tctgattcag aaaatgagac tagtaccctt tggtcagctg   3900
```

```
taaacaaaca cccagttgta aatgtctcaa gttcaggctt aactgcagaa ccaatcaaaa   3960

agaatagaat ctttagagca aactgtgttt ctccacatct ggaggtgagt ctgccagggc   4020

agtttggaaa tatttacttc acaagtattg acactgttgt tggtattaac aacataaagt   4080

tgctcaaagg caatcattat ttcaagtggc ttaaagttac ttctgacagt tttggtatat   4140

ttattggcta ttgccatttg ctttttgttt tttctctttg ggtttattaa tgtaaagcag   4200

ggattattaa cctacagtcc agaaagcctg tgaatttgaa tgaggaaaaa attacatttt   4260

tgtttttacc accttctaac taaatttaac attttattcc attgcgaata gagccataaa   4320

ctcaaagtgg taataacagt acctgtgatt ttgtcattac caatagaaat cacagacatt   4380

ttatactata ttacagttgt tgcagatacg ttgtaagtga aatatttata ctcaaaacta   4440

ctttgaaatt agacctcctg ctggatcttg tttttaacat attaataaaa catgtttaaa   4500

attttgatat tttgataatc atatttcatt atcatttgtt tcctttgtaa tctatatttt   4560

atatatttga aaacatcttt ctgagaagag ttccccagat ttcaccaatg aggttcttgg   4620

catgcacaca cacagagtaa gaactgattt agaggctaac attgacattg gtgcctgaga   4680

tgcaagactg aaattagaaa gttctcccaa agatacacag ttgttttaaa gctaggggtg   4740

agggggaaa tctgccgctt ctataggaat gctctccctg gagcctggta gggtgctgtc    4800

cttgtgttct ggctggctgt tatttttctc tgtccctgct acgtcttaaa ggacttgttt   4860

ggatctccag ttcctagcat agtgcctggc acagtgcagg ttctcaatga gtttgcagag   4920

tgaatggaaa tataaactag aaatatatcc ttgttgaaat cagcacacca gtagtcctgg   4980

tgtaagtgtg tgtacgtgtg tgtgtgtgtg tgtgtgtgtg tgtaaaacca ggtggagata   5040

taggaactat tattggggta tgggtgcata aattgggatg ttctttttaa aaagaaactc   5100

caaacagact tctggaaggt tattttctaa gaatcttgct ggcagcgtga aggcaacccc   5160

cctgtgcaca gccccaccca gcctcacgtg gccacctctg tcttccccca tgaagggctg   5220

gctccccagt atatataaac ctctctggag ctcgggcatg agccagcaag g            5271

<210> SEQ ID NO 35
<211> LENGTH: 19
<212> TYPE: DNA
<213> ORGANISM: Homo sapiens

<400> SEQUENCE: 35

aactattatt ggggtatgg                                                  19

<210> SEQ ID NO 36
<211> LENGTH: 19
<212> TYPE: DNA
<213> ORGANISM: Homo sapiens

<400> SEQUENCE: 36

ttggtgaggc ttcctctgg                                                  19

<210> SEQ ID NO 37
<211> LENGTH: 283
<212> TYPE: DNA
<213> ORGANISM: Homo sapiens

<400> SEQUENCE: 37

aactattatt ggggtatggg tgcataaatt gggatgttct ttttaaaaag aaactccaaa     60

cagacttctg gaaggttatt ttctaagaat cttgctggca gcgtgaaggc aacccccctg    120
```

-continued

```
tgcacagccc cacccagcct cacgtggcca cctctgtctt cccccatgaa gggctggctc    180

cccagtatat ataaacctct ctggagctcg ggcatgagcc agcaaggcca cccatccagg    240

cacctctcag cacagcagag ctttccagag gaagcctcac caa                      283


<210> SEQ ID NO 38
<211> LENGTH: 227
<212> TYPE: DNA
<213> ORGANISM: Homo sapiens

<400> SEQUENCE: 38

aactattatt ggggtatggg tgcataaatt gggatgttct ttttaaaaag aaactccaaa     60

cagacttctg gaaggttatt ttctaagaat cttgctggca gcgtgaaggc aacccccctg    120

tgcacagccc cacccagcct cacgtggcca cctctgtctt cccccatgaa gggctggctc    180

cccagtatat ataaacctct ctggagctcg ggcatgagcc agcaagg                  227
```

NUCLEIC ACIDS, KITS, AND METHODS FOR THE DIAGNOSIS, PROGNOSIS AND TREATMENT OF GLAUCOMA AND RELATED DISORDERS

CROSS REFERENCE TO RELATED APPLICATIONS

This application is a continuation-in-part of U.S. patent application Ser. No. 09/227,881, filed Jan. 11, 1999, specifically incorporated herein by reference, which is a continuation-in-part of U.S. patent application Ser. No. 08/938,669, filed Sep. 26, 1997, now issued as U.S. Pat. No. 6,171,788, specifically incorporated by reference herein, which is a continuation-in-part of U.S. patent application Ser. No. 08/791,154, filed Jan. 28, 1997, now abandoned, also specifically incorporated by reference herein.

FIELD OF THE INVENTION

The present invention relates to the field of diagnostic and prognostic methods and kits, treatments, and compositions useful in understanding and identifying glaucoma, related intraocular pressure-disorders, and steroid sensitivity.

BACKGROUND OF THE INVENTION

A group of debilitating eye diseases, the "Glaucomas" represent the leading cause of preventable blindness in the United States and other developed nations. In general, glaucomas are characterized by the alteration of the trabecular meshwork (TM), which consists of specialized endothelial cells and their associated connective tissue. The TM endothelial cells line the path the aqueous humor of the eye filters through during the normal, physiological flux. The cells generate and regulate the TM by producing extracellular molecules, the composition of which is thought to directly control the aqueous fluid flow.

In Primary Open Angle Glaucoma ("POAG"), the most common form of glaucoma, an alteration in the TM leads to an obstruction of the normal ability of aqueous humor to leave its chamber surrounding the iris. However, the specific cells in the chamber between the iris and the cornea, in a region called the iridocorneal angle, remain "open" in that they continue to allow the egress of aqueous fluid (see, Vaughan, D. et al., In: *General Ophthalmology*, Appleton & Lange, Norwalk, Conn., pp. 213–230 (1992); and *Gray's Anatomy*, 37$^{th}$ Ed., Churchill Livingstone, London, pp. 1180–1190 (1989)). As a result of the alteration in the TM and the obstruction, an increased intraocular pressure ("IOP") can be observed. IOP can result in progressive visual loss and blindness if not treated appropriately and in a timely fashion.

Glaucomas are estimated to affect between 0.4% and 3.3% of all adults over 40 years old (Leske, M. C. et al., *Amer. J. Epidemiol.* 113:1843–1846 (1986); Bengtsson, B., *Br. J. Ophthamol.* 73:483–487 (1989); Strong, N. P., *Ophthal. Physiol. Opt.* 12:3–7 (1992)). Moreover, the prevalence of the disease rises to over 6% of those 75 years or older (Strong, N. P., *Ophthal. Physiol. Opt.* 12:3–7 (1992)).

A link between steroid, corticosteroid, or glucocorticoid treatments and the increased IOP found in POAG disease has long been suspected. While only 5% of the normal population have high IOP increases in response to topical glucocorticoids, greater than 40–50% of similarly treated patients with POAG show a high IOP increase (16 mm Hg). In addition, an Open Angle Glaucoma may be induced by exposure to glucocorticoids. This observation has suggested that an increased or abnormal glucocorticoid response in trabecular cells of the TM may be involved in POAG (Zhan, G. L. et al., *Exper. Eye Res.* 54:211–218 (1992); Yun, A. J. et al., *Invest. Ophthamol. Vis. Sci.* 30:2012–2022 (1989); Clark, A. F., *Exper. Eye Res.* 55: 265 (1992); Klemetti, A., *Acta Ophthamol.* 68: 29–33 (1990); Knepper, P. A., U.S. Pat. No. 4,617,299).

The ability of glucocorticoids to induce a glaucoma-like condition has led to efforts to identify genes or gene products induced by the cells of the trabecular meshwork in response (Polansky, J. R. et al., In: *Glaucoma Update IV*, Springer-Verlag, Berlin, pp. 20–29 (1991); Polansky J. R. and Weinrob, R. N., In: *Handbook of Experimental Pharmacology*, Vol. 69, Springer-Verlag, Berlin, pp. 461–538 (1984)). Initial efforts using short-term exposure to dexamethasone revealed only changes in specific protein synthesis. Extended exposure to relatively high levels of dexamethasone was, however, found to induce the expression of related 66 kD and 55 kD proteins that could be visualized by gel electrophoresis (Polansky, J. R. et al., In: *Glaucoma Update IV*, Springer-Verlag, Berlin, pp. 20–29 (1991)). The induction kinetics of these proteins as well as their dose response characteristics were similar to the kinetics that were required for steroid-induced IOP elevation in human subjects (Polansky, J. R. et al., In: *Glaucoma Update IV*, Springer-Verlag, Berlin, pp. 20–29 (1991)). Problems of aggregation and apparent instability or loss of protein in the purification process were obstacles in obtaining a direct protein sequence.

Nguyen et al., U.S. patent application Ser. No: 08/649,432, filed May 17, 1996, now U.S. Pat. No. 5,789,169, the entire disclosure of which is hereby incorporated by reference as if set forth at length herein, disclosed a novel protein sequence (the TIGR, trabecular meshwork inducible glucocorticoid response protein) highly induced by glucocorticoids in the endothelial lining cells of the human trabecular meshwork. Nguyen et al. also disclosed the cDNA sequence for that protein, the protein itself, molecules that bind to it, and nucleic acid molecules that encode it, and provided improved methods and reagents for diagnosing glaucoma and related disorders, as well as for diagnosing other diseases or conditions, such as cardiovascular, immunological, or other diseases or conditions that affect the expression or activity of the protein.

Because increased IOP is a readily measurable characteristic of glaucoma, the diagnosis of the disease is largely screened for by measuring intraocular pressure (tonometry) (Strong, N. P., *Ophthal. Physiol. Opt.* 12:3–7 (1992), Greve, M. et al., *Can. J. Ophthamol.* 28:201–206 (1993)). Unfortunately, because glaucomatous and normal pressure ranges overlap, such methods are of limited value unless multiple readings are obtained (Hitchings, R. A., *Br. J. Ophthamol.* 77:326 (1993); Tuck, M. W. et al., *Ophthal. Physiol. Opt.* 13: 227–232 (1993); Vaughan, D. et al., In: *General Ophthamology*, Appleton & Lange, Norwalk, Conn., pp. 213–230 (1992); Vernon, S. A., *Eye* 7:134–137 (1993)). Patients may also have a differential sensitivity to optic nerve damage at a given IOP. For these reasons, additional methods, such as direct examination of the optic disk and determination of the extent of a patient's visual field loss are often conducted to improve the accuracy of diagnosis (Greve, M. et al., *Can. J. Ophthamol.* 28: 201–206 (1993)). Moreover, these techniques are of limited prognostic value. In some aspects, the present invention fulfills the need for improved diagnostic and prognostic methods.

The elevation of intraocular pressure (IOP) due to topical corticosteroids (and other routes of administration) is an important clinical problem that limits the clinical use of these effective anti-inflammatory agents. If not observed in sufficient time, the IOP elevation (especially in certain individuals who show the high end of steroid-induced IOP elevations) can result in optic nerve damage and permanent visual field loss, termed "steroid glaucoma." Even patients taking inhaled, nasal, rectal, and facial steroids may be at risk. The present invention, in part, provides improved diagnostic agents, prognostic agents, therapeutic agents and methods that address this clinical problem.

SUMMARY OF THE INVENTION

The invention relates to nucleic acids, genes, proteins and cells that can be used in the treatment, diagnosis, prognosis, and identification of glaucoma, IOP-related disorders, or steroid sensitivity. The invention encompasses numerous agents, compositions, and methods, some of which are described by the objects and aspects of the invention detailed below. Others can be devised from the entire contents of this disclosure, and from the detailed description that follows.

In one aspect, the invention relates to nucleic acids comprising non-coding regions or promoter regions associated with the TIGR (trabecular meshwork inducible glucocorticoid response) gene of mammals. These nucleic acids can be used in identifying polymorphisms in the genomes of mammals and humans that predict steroid sensitivity or a susceptibility to glaucomas or diseases related to alterations in IOP. A number of diagnostic or prognostic methods and kits can be designed from these nucleic acids.

In one embodiment, the nucleic acids can be used to identify or detect a single base polymorphism in a genome. In other embodiments, two or more single base polymorphisms or multiple base polymorphisms can be identified or detected. The detection of a known polymorphism can be the basis for diagnostic and prognostic methods and kits of the invention. Various methods of detecting nucleic acids can be used in these methods and with the kits, including, but not limited to, solution hybridization, hybridization to microarrays containing immobilized nucleic acids or other immobilized nucleic acids, amplification-based methods such as PCR and the like, and an appropriate biosensor apparatus comprising a nucleic acid or nucleic acid binding reagent.

In another aspect, the invention relates to specific sequences and variants or mutants from the promoter or 5' regulatory region of the human TIGR gene and nucleic acids incorporating these sequences, variants or mutants. The nucleic acids can be incorporated into the methods and kits of the invention, or used in expression systems, vectors, and cells to produce a protein or polypeptide of interest, or used in methods to identify or detect regulatory proteins or proteins that specifically bind to promoter or regulatory regions of the TIGR gene. While many of the examples below detail work from human tissue, other animals may be used as a source of the sequences.

In one embodiment of this aspect of the invention, for example, nucleic acids having the disclosed TIGRmt11 sequence variant, represented by the change at nucleotide 5113 in SEQ ID NO: 1, 3, or 34 from T to C, or the change in nucleotide 5117 in SEQ ID NO: 2 from T to C. The presence of sequence variant mt11 is linked to the high IOP response to steroid treatments and a nucleic acid incorporating the singe base substitution can be used to identify and determine individuals at risk for developing glaucoma from undergoing a steroid treatment therapy, or a progression from an ocular hypertensive state, or those with a steroid sensitivity. And, because of the link between high IOP responses to steroids and the later development of glaucoma, nucleic acids having the TIGRmt11 sequence variant may also be used to identify the risk of developing glaucomas, such as POAG. The identification of changes in IOP can be done by any known means, however, the "Armaly" criteria is preferred (see Armaly, M. F., *Arch. Ophthalmol.* 70:492 (1963); Armaly, M. F., *Arch Ophtalmol.* 75:32–35 (1966); Kitazawa, Y. et al., *Arch. Ophthalmol.* 99:819–823 (1981); Lewis, J. M. et al., *Amer. J. Ophthalmol.* 106:607–612 (1988); Becker, B. et al. *Amer. J.Ophthalmol.* 57:543 (1967), all of which are specifically incorporated herein by reference in their entireties).

An object of the invention is to provide a method for diagnosing glaucoma in a patient which comprises the steps: (A) incubating under conditions permitting nucleic acid hybridization: a marker nucleic acid molecule, said marker nucleic acid molecule comprising a nucleotide sequence of a polynucleotide that specifically hybridizes to a polynucleotide that is linked to a TIGR promoter, and a complementary nucleic acid molecule obtained from a cell or a bodily fluid of said patient, wherein nucleic acid hybridization between said marker nucleic acid molecule, and said complementary nucleic acid molecule obtained from said patient permits the detection of a polymorphism whose presence is predictive of a mutation affecting TIGR response in said patient; (B) permitting hybridization between said marker nucleic acid molecule and said complementary nucleic acid molecule obtained from said patient; and (C) detecting the presence of said polymorphism, wherein the detection of the polymorphism is diagnostic of glaucoma.

Another object of the invention is to provide a method for prognosing glaucoma in a patient which comprises the steps: (A) incubating under conditions permitting nucleic acid hybridization: a marker nucleic acid molecule, said marker nucleic acid molecule comprising a nucleotide sequence of a polynucleotide that specifically hybridizes to a polynucleotide that is linked to a TIGR promoter, and a complementary nucleic acid molecule obtained from a cell or a bodily fluid of said patient, wherein nucleic acid hybridization between said marker nucleic acid molecule, and said complementary nucleic acid molecule obtained from said patient permits the detection of a polymorphism whose presence is predictive of a mutation affecting TIGR response in said patient; (B) permitting hybridization between said marker nucleic acid molecule and said complementary nucleic acid molecule obtained from said patient; and (C) detecting the presence of said polymorphism, wherein the detection of the polymorphism is prognostic of glaucoma.

Another object of the invention is to provide marker nucleic acid molecules capable of specifically detecting TIGRmt1, TIGRmt2, TIGRmt3, TIGRmt4, TIGRmt5, TlGRmt11 and TIGRsv1.

Another object of the invention is to provide a method for diagnosing steroid sensitivity in a patient which comprises the steps: (A) incubating under conditions permitting nucleic acid hybridization: a marker nucleic acid molecule, the marker nucleic acid molecule comprising a nucleotide sequence of a polynucleotide that is linked to a TIGR promoter, and a complementary nucleic acid molecule obtained from a cell or a bodily fluid of the patient, wherein nucleic acid hybridization between the marker nucleic acid molecule, and the complementary nucleic acid molecule obtained from the patient permits the detection of a polymorphism whose presence is predictive of a mutation affecting TIGR response in the patient; (B) permitting hybridization between said TIGR-encoding marker nucleic acid molecule and the complementary nucleic acid molecule obtained from the patient; and (C) detecting the presence of the polymorphism, wherein the detection of the polymorphism is diagnostic of steroid sensitivity.

Further objects of the invention provide a nucleic acid molecule that comprises the sequence of SEQ ID NO: 1 or 34, recombinant DNA molecules containing a polynucleotide that specifically hybridizes to SEQ ID NO: 1 or 34 and substantially purified molecules that specifically bind to a nucleic acid molecule that comprises the sequence of SEQ ID NO: 1 or 34.

Further objects of the invention provide a nucleic acid molecule that comprises the sequence of SEQ ID NO: 3, recombinant DNA molecules containing a polynucleotide that specifically hybridizes to SEQ ID NO: 3 and substantially purified molecules that specifically bind to a nucleic acid molecule that comprises the sequence of SEQ ID NO: 3.

Additional objects of the invention provide a nucleic acid molecule that comprises the sequence of SEQ ID NO: 4, recombinant DNA molecules containing a polynucleotide that specifically hybridizes to SEQ ID NO: 4 and substantially purified molecules that specifically bind to a nucleic acid molecule that comprises the sequence of SEQ ID NO: 4.

Additional objects of the invention provide a nucleic acid molecule that comprises the sequence of SEQ ID NO: 5, recombinant DNA molecules containing a polynucleotide that specifically hybridizes to SEQ ID NO: 5 and substantially purified molecules that specifically bind to a nucleic acid molecule that comprises the sequence of SEQ ID NO: 5.

An additional object of the present invention is to provide a method of treating glaucoma which comprises administering to a glaucomatous patient an effective amount of an agent that inhibits the synthesis of a TIGR protein.

Indeed, the molecules of the present invention may be used to diagnose diseases or conditions which are characterized by alterations in the expression of extracellular proteins.

BRIEF DESCRIPTION OF THE FIGURES

FIGS. 1A, 1B, 1C, 1D and 1E provide the nucleic acid sequence of a TIGR promoter region (SEQ ID NO: 1) from an individual without glaucoma.

FIGS. 2A, 2B, 2C and 2D provide the location and sequence changes highlighted in bold associated with glaucoma mutants TIGRmt1, TIGRmt2, TIGRmt3, TIGRmt4, TIGRmt5, TIGRmt11, and TIGRsv1 (SEQ ID NO: 2).

FIGS. 3A, 3B, 3C, 3D, 3E, 3F, and 3G provide nucleic acid sequences of a TIGR promoter, and TIGR exons, TIGR introns and TIGR downstream sequences (SEQ ID NO: 3, SEQ ID NO: 4, and SEQ ID NO: 5).

FIG. 6 provides a homology analysis of TIGR homology with olfactomedin and olfactomedin-related proteins.

FIG. 7(A & B) shows the nucleotide sequence of TIGR (SEQ ID NO: 26).

FIG. 8(A & B) shows the amino acid sequence of TIGR (SEQ ID NO: 32).

DETAILED DESCRIPTION OF THE INVENTION

I. Agents of the Invention

Figure 4:
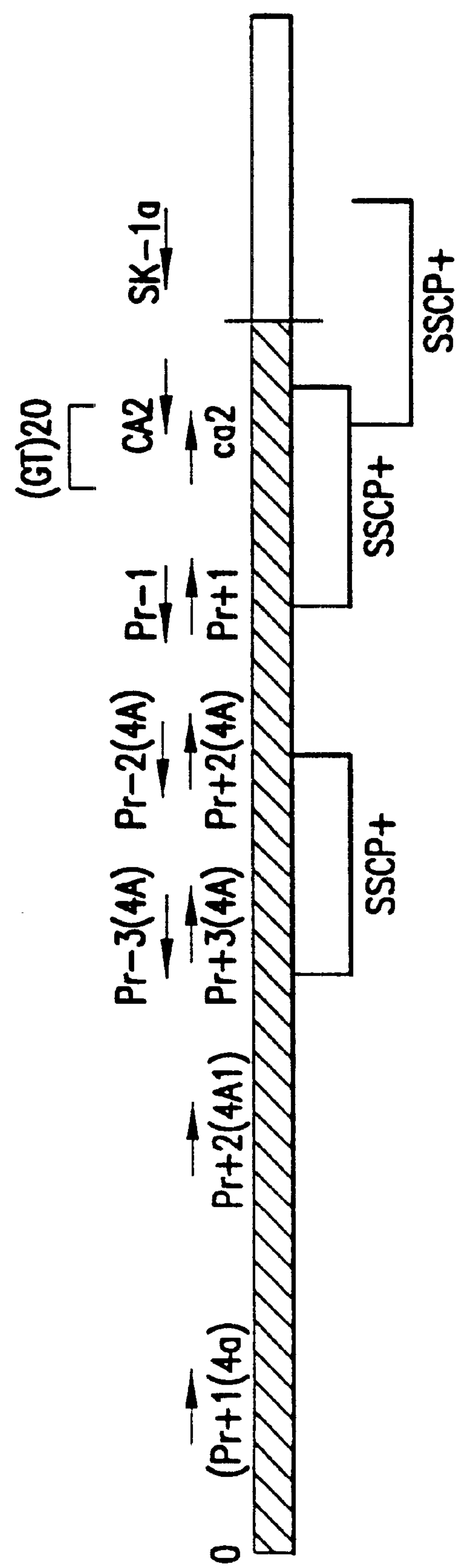
FIG. 4 provides a diagrammatic representation of the location of primers on the TIGR gene promoter for Single Strand Conformational Polymorphism (SSCP) analysis.

As used herein, the term "glaucoma" has its art recognized meaning, and includes both primary glaucomas, secondary glaucomas, juvenile glaucomas, congenital glaucomas, and familial glaucomas, including, without limitation, pigmentary glaucoma, high tension glaucoma and low tension glaucoma and their related diseases. The methods of the present invention are particularly relevant to the diagnosis of POAG, OAG, juvenile glaucoma, and inherited glaucomas. The methods of the present invention are also particularly relevant to the prognosis of POAG, OAG, juvenile glaucoma, and inherited glaucomas. A disease or condition is said to be related to glaucoma if it possesses or exhibits a symptom of glaucoma, for example, an increased intra-ocular pressure resulting from aqueous outflow resistance (see, Vaughan, D. et al., In: *General Ophthamology*, Appleton & Lange, Norwalk, Conn., pp. 213–230 (1992)). The preferred agents of the present invention are discussed in detail below.

The agents of the present invention are capable of being used to diagnose the presence or severity of glaucoma and its related diseases in a patient suffering from glaucoma (a "glaucomatous patient"). The agents of the present invention are also capable of being used to prognose the presence or severity of glaucoma and its related diseases in a person not yet suffering from any clinical manifestations of glaucoma. Such agents may be either naturally occurring or non-naturally occurring. As used herein, a naturally occurring molecule may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

As used herein, the term "TIGR protein" refers to a protein having the amino acid sequence of SEQ ID NO: 32. As used herein, the agents of the present invention comprise nucleic acid molecules, proteins, and organic molecules.

As indicated above, the trabecular meshwork has been proposed to play an important role in the normal flow of the aqueous, and has been presumed to be the major site of outflow resistance in glaucomatous eyes. Human trabecular meshwork (HTM) cells are endothelial like cells which line the outflow channels by which aqueous humor exits the eye; altered synthetic function of the cells may be involved in the pathogenesis of steroid glaucoma and other types of glaucoma. Sustained steroid treatment of these cells are interesting because it showed that a major difference was observed when compared to 1–2 day glucocorticoid (GC)

exposure. This difference appears relevant to the clinical onset of steroid glaucoma (1–6 weeks).

Although trabecular meshwork cells had been found to induce specific proteins in response to glucocorticoids (see, Polansky, J. R., In: "*Basic Aspects of Glaucoma Research III*", Schattauer, N.Y. 307–318 (1993)), efforts to purify the expressed protein were encumbered by insolubility and other problems. Nguyen, T. D. et al., (In: "*Basic Aspects of Glaucoma Research III*", Schattauer, N.Y., 331–343 (1993), herein incorporated by reference) used a molecular cloning approach to isolate a highly induced mRNA species from glucocorticoid-induced human trabecular cells. The mRNA exhibited a time course of induction that was similar to the glucocorticoid-induced proteins. The clone was designated "II.2" (ATCC No: 97994, American Type Culture Collection, Manassas, Va.).

Nguyen et al., U.S. patent application Ser. No: 08/649,432 filed May 17, 1996, now U.S. Pat. No. 5,789,169, isolated a II.2 clone which encoded a novel secretory protein that is induced in cells of the trabecular meshwork upon exposure to glucocorticoids. It has been proposed that this protein may become deposited in the extracellular spaces of the trabecular meshwork and bind to the surface of the endothelial cells that line the trabecular meshwork, thus causing a decrease in aqueous flow. Quantitative dot blot analysis and PCR evaluations have shown that the mRNA exhibits a progressive induction with time whereas other known GC-inductions from other systems and found in HTM cells (metallothionein, alpha-1 acid glycoprotein and alpha-1 antichymotrypsin) reached maximum level at one day or earlier. Of particular interest, the induction level of this clone was very high (4–6% total cellular mRNA) with control levels undetectable without PCR method. Based on studies of $^{35}$S methionine cell labeling, the clone has the characteristics recently discovered for the major GC-induced extracellular glycoprotein in these cells, which is a sialenated, N-glycosylated molecule with a putative inositol phosphate anchor. The induction of mRNA approached 4% of the total cellular mRNA. The mRNA increased progressively over 10 days of dexamethasone treatment. The 11.2 clone is 2.0 Kb whereas the Northern blotting shows a band of 2.5 Kb. Although not including a poly A tail, the 3' end of the clone contains two consensus polyadenylation signals.

A genomic clone was isolated and designated $P_1$TIGR clone (ATCC No: 97570, American Type Culture Collection, Rockville, Md.). In-situ hybridization using the $P_1$ TIGR clone shows a TIGR gene and/or a sequence or sequences that specifically hybridize to the TIGR gene located at chromosome 1, q21–27, and more preferably to the TIGR gene located at chromosome 1, q22–26, and most preferably to the TIGR gene located at chromosome 1, q24. Clone $P_1$TIGR comprises human genomic sequences that specifically hybridize to the TIGR gene cloned into the BamHI site of vector pCYPAC (Ioannou et al., *Nature Genetics*, 6:84–89 (1994) herein incorporated by reference).

As used herein, the term "TIGR gene" refers to the region of DNA involved in producing a TIGR protein; it includes, without limitation, regions preceeding and following the coding region as well as intervening sequences between individual coding regions.

As used herein, the term "TIGR exon" refers to any interrupted region of the TIGR gene that serves as a template for a mature TIGR mRNA molecule. As used herein, the term "TIGR intron" refers to a region of the TIGR gene which is non-coding and serves as a template for a TIGR mRNA molecule.

Localization studies using a Stanford G3 radiation hybrid panel mapped the TIGR gene near the D1S2536 marker with a LOD score of 6.0 (Richard et al., *American Journal of Human Genetics* 52.5: 915–921 (1993), herein incorporated by reference); Frazer et al., Genomics 14.3: 574–578 (1992), herein incorporated by reference; Research Genetics, Huntsville, Ala.). Other markers in this region include: D1S210; D1S1552; D1S2536; D1S2790; SHGC-12820; and D1S2558.

Sequences located upstream of the TIGR coding region are isolated and sequenced in a non-glaucornic individual. The upstream sequence is set forth in SEQ ID. No. 1 and 34. Sequence comparisons of the upstream region of a non-glaucoma individual and individuals with glaucoma identify a number of mutations in individuals with glaucoma. Some of these mutations are illustrated in FIG. 2, the sequence of which can be used to identify the exact changes in the human genomic sequences from the upstream region of the TIGR gene disclosed here (SEQ ID NO: 1, 2, 3, and 34). SEQ ID NO: 3 includes the regions through the start of transcription and the start of translation, as evident from a sequence comparison to the figures. SEQ ID NO: 34 ends before the transcription start site, again as evident from a sequence comparison with the figures. Six mutations are specifically disclosed here. TIGRmt1 is the result of a replacement of a cytosine with a guanine at position 4337 (SEQ ID NO: 1, SEQ ID NO: 2, and SEQ ID NO: 3). TIGRmt2 is the result of a replacement of a cytosine with a thymine at position 4950 (SEQ ID NO: 1, SEQ ID NO: 2, and SEQ ID NO: 3). TIGRmt3 is the result of an addition in the following order of a guanine, a thymine, a guanine, and a thymine (GTGT) at position 4998 (SEQ ID NO: 1, SEQ ID NO: 2, and SEQ ID NO: 3). TIGRmt4 is the result of a replacement of an adenine with a guanine at position 4256 (SEQ ID NO: 1, SEQ ID NO: 2, and SEQ ID NO: 3). TIGRmt5 is the result of a replacement of a guanine with an adenine at position 4262 (SEQ ID NO: 1, SEQ ID NO: 2 and SEQ ID NO: 3). TIGRmt1 (not pictured in FIG. 2) is the result of a replacement of a thymine with a cytosine at position 5113 (SEQ ID NO: 1, 3, or 34) and at the equivalent position in SEQ ID NO: 2, at nucleotide 5117. One or more of TIGRmt1, TIGRmt2, TIGRmt3, TIGRmt4, TIGRmt5, and TIGTmt11 can be homozygous or heterozygous.

Sequence comparisons of the upstream region of a non-glaucoma individual and individuals with glaucoma identify at least one sequence variation in individuals with glaucoma. One such sequence variant is illustrated in FIG. 2. TIGRsv1 is the result of a replacement of an adenine with a guanine at position 4406 (SEQ ID NO: 1, SEQ ID NO: 2 and SEQ ID NO: 3). Also, the presence of TIGRmt11 is associated with steroid sensitivity or an increased susceptibility to developing glaucoma or IOP-related disorders during steroid or corticosteroid treatment.

Molecules comprising sequences upstream of the TIGR coding region provide useful markers for polymorphic studies. Such molecules include primers suitable for single strand conformational polymorphic studies, examples of which are as follows: forward primer "Sk-1a": 5'-TGA GGC TTC CTC TGG AAA C-3' (SEQ ID NO: 6); reverse primer "ca2": 5'-TGA AAT CAG CAC ACC AGT AG-3' (SEQ ID NO: 7); forward primer "CA2": 5'-GCA CCC ATA CCC CAA TAA TAG-3' (SEQ ID NO: 8); reverse primer "Pr+1": 5'-AGA GTT CCC CAG ATT TCA CC-3' (SEQ ID NO: 9); forward primer "Pr−1": 5'-ATC TGG GGA ACT CTT CTC AG-3' (SEQ ID NO: 10); reverse primer "Pr+2(4A2)": 5'-TAC AGT TGT TGC AGA TAC G-3' (SEQ ID NO: 11); forward primer "Pr−2(4A)": 5'-ACA ACG TAT CTG CAA CAA CTG-3' (SEQ ID NO: 12); reverse primer “Pr+3(4A)”: 5'-TCA GGC TTA ACT GCA GAA CC-3' (SEQ ID NO: 13); forward primer “Pr−3(4A)”: 5'-TTG GTT CTG CAG TTA AGC C-3' (SEQ ID NO: 14); reverse primer “Pr+2(4A1)”: 5'-AGC AGC ACA AGG GCA ATC C-3' (SEQ ID NO: 15); reverse primer “Pr+1(4A)”: 5'-ACA GGG CTA TAT TGT GGG-3' (SEQ ID NO: 16).

In addition, molecules comprising sequences within TIGR exons provide useful markers for polymorphic studies. Such molecules include primers suitable for single strand conformational polymorphic studies, examples of which are as follows: forward primer “KS 1X”: 5'-CCT GAG ATG CCA GCT GTC C-3' (SEQ ID NO: 17); reverse primer “SK1XX”: 5'-CTG AAG CAT TAG AAG CCA AC-3' (SEQ ID NO: 18); forward primer “KS2a1”: 5'-ACC TTG GAC CAG GCT GCC AG-3' (SEQ ID NO: 19); reverse primer “SK3” 5'-AGG TTT GTT CGA GTT CCA G-3' (SEQ ID NO: 20); forward primer “KS4”: 5'-ACA ATT ACT GGC AAG TAT GG-3' (SEQ ID NO: 21); reverse primer “SK6A”: 5'-CCT TCT CAG CCT TGC TAC C-3' (SEQ ID NO: 22); forward primer “KS5”: 5'-ACA CCT CAG CAG ATG CTA CC-3' (SEQ ID NO: 23); reverse primer “SK8”: 5'-ATG GAT GAC TGA CAT GGC C-3' (SEQ ID NO: 24); forward primer “KS6”: 5'-AAG GAT GAA CAT GGT CAC C-3' (SEQ ID NO: 25).

Figure 5:
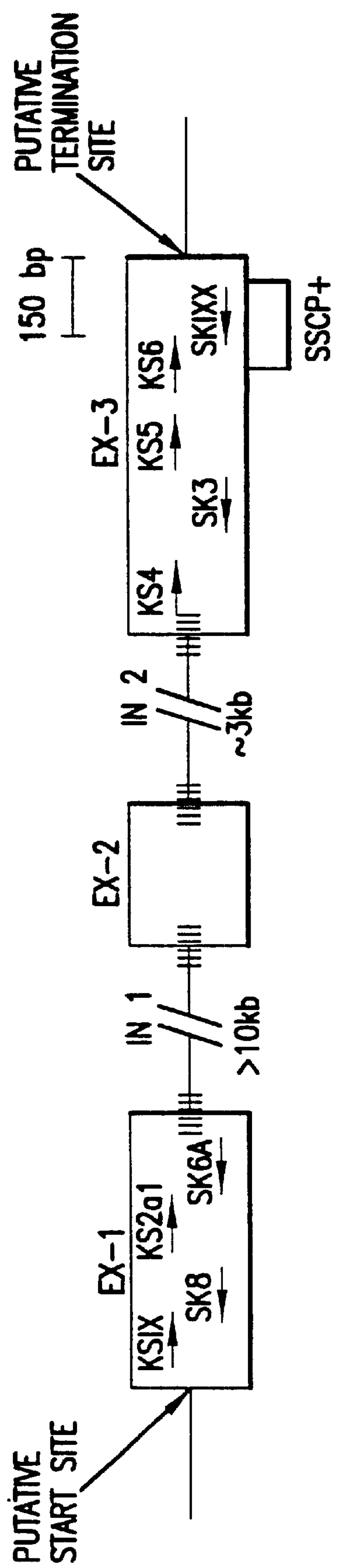
FIG. 5 provides a diagrammatic representation of the TIGR exons and the arrangement of SSCP primers.

The locations of primers: Sk-1a, ca2, CA2, Pr+1, Pr−1, Pr+2(4A2), Pr−2(4A), Pr+3(4A), Pr−3(4A), Pr−3(4A), Pr+2 (4A1), and Pr+1(4A) are diagrammatically set forth in FIG. 4. The location of primers: KS1X, SK1XX, Ks2a1, SK3, KS4, SK6A, KS5, SK8, and KS6 are diagramatically set forth in FIG. 5.

The primary structure of the TIGR coding region initiates from an ATG initiation site (SEQ ID NO:3, residues 5337–5339) and includes a 20 amino acid consensus signal sequence a second ATG (SEQ ID NO: 3, residues 5379–5381), indicating that the protein is a secretory protein. The nucleotide sequence for the TIGR coding region is depicted in FIG. 7 (SEQ ID NO: 26). The protein contains an N-linked glycosylation site located in the most hydrophilic region of the molecule. The amino terminal portion of the protein is highly polarized and adopts alpha helical structure as shown by its hydropathy profile and the Garnier-Robison structure analysis. In contrast, the protein contains a 25 amino acid hydrophobic region near its carboxy terminus. This region may comprise a glucocorticoid-induced protein (GIP) anchoring sequence. The amino acid sequence of TIGR is depicted in FIG. 8 (SEQ ID NO: 32).

Study of cyclohexamide treatment in the absence and presence of GC suggest that the induction of TIGR may involve factors in addition to the GC receptor. The TIGR gene may be involved in the cellular stress response since it is also induced by stimulants such as $H_2O_2$, 12-O-tetradecanolyphorbol-13-acetate (TPA), and high glucose; this fact may relate to glaucoma pathogenesis and treatment.

A preferred class of agents comprises TIGR nucleic acid molecules (“TIGR molecules”) or fragments thereof. Such molecules may be either DNA or RNA. A second preferred class of agents (“TIGR molecules”) comprises the TIGR protein, its peptide fragments, fusion proteins, and analogs.

TIGR nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the “complement” of another nucleic acid molecule if the molecules exhibit complete complementarity. As used herein, molecules are said to exhibit “complete complementarity” when every nucleotide of one of the molecules is complementary to a nucleotide of the other. Two molecules are said to be “minimally complementary” if they can hybridize to one another with sufficient stability to permit them to remain annealed to one another under at least conventional “low-stringency” conditions. Similarly, the molecules are said to be “complementary” if they can hybridize to one another with sufficient stability to permit them to remain annealed to one another under conventional “high-stringency” conditions. Conventional stringency conditions are described by Sambrook et al., In: Molecular Cloning, A Laboratory Manual, 2nd Edition, Cold Spring Harbor Press, Cold Spring Harbor, N.Y. (1989)), and by Haymes et al., In: Nucleic Acid Hybridization, A Practical Approach, IRL Press, Washington, D.C. (1985), the entirety of which is herein incorporated by reference. Departures from complete complementarity are therefore permissible, as long as such departures do not completely preclude the capacity of the molecules to form a double-stranded structure. In order for an nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1–5 or 34, or complements thereof, or fragments of about 20 to about 200 bases of either, under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO: 1–5 or 34, or complements or fragments of either under high stringency conditions.

In one aspect of the present invention, a preferred marker nucleic acid molecule of the present invention has the nucleic acid sequence set forth in SEQ ID NO: 6–25 or 33, or complements thereof or fragments of either. In another aspect of the present invention, a preferred marker nucleic acid molecule of the present invention shares between about 80% to about 100% or about 90% to about 100% sequence identity with the nucleic acid sequence set forth in SEQ ID NO: 6–25 or 33, or complement thereof or fragments of either. In a further aspect of the present invention, a preferred marker nucleic acid molecule of the present invention shares between about 95% to about 100% sequence identity with the sequence set forth in SEQ ID NO: 6–25 or 33, or complement thereof or fragments of either. In a more preferred aspect of the present invention, a preferred marker nucleic acid molecule of the present invention shares between 98% and about 100% sequence identity with the nucleic acid sequence set forth in SEQ ID NO:6–25 or 33, or complement thereof or fragments of either.

Regulatory Regions and Agents that Bind to the Regions or Agents that Alter the Binding of a Molecule that Binds to the Regions Sequence comparisons of the upstream region identify a number of DNA motifs (cis elements) or regulatory regions. These DNA motifs or cis elements are shown in FIG. 1. These motifs include, without limitation, glucocorticoid response motif(s), shear stress response motif(s), NFκB recognition motif(s), and AP1 motif(s). The locations of these and other motifs, discussed below, are diagramatically set forth in FIG. 1.

As used herein, the term "cis elements capable of binding" refers to the ability of one or more of the described cis elements to specifically bind an agent. Such binding may be by any chemical, physical or biological interaction between the cis element and the agent, including, but not limited, to any covalent, steric, agostic, electronic and ionic interaction between the cis element and the agent. As used herein, the term "specifically binds" refers to the ability of the agent to bind to a specified cis element but not to wholly unrelated nucleic acid sequences. Regulatory region refers to the ability of a nucleic acid fragment, region or length to functionally perform a biological activity. The biological activity may be binding to the nucleic or specific DNA sequence. The biological activity may also modulate, enhance, inhibit or alter the transcription of a nearby coding region. The biological activity may be identified by a gel shift assay, in which binding to a nucleic acid fragment can be detected. Other methods of detecting the biological activity in a nucleic acid regulatory region are known in the art (see *Current Protocols in Molecular Biology*, for example).

In an embodiment to identify or detect regulatory proteins or proteins or compounds that specifically bind to promoter or regulatory regions of the TIGR gene, a number of vector systems employing reporter genes can be useful. The promoter or 5' regulatory regions can be linked to control expression of the reporter gene so that the presence of the reporter gene indicates the transcriptional activity from the promoter or 5' regulatory region. The DNA constructs, vectors, and cells made for this aspect of the invention, and the methods employing them, can be useful in a variety of ways. For example, they can detect the presence or absence of tissue-specific factors that modulate TIGR gene expression. Modulating expression can mean increasing or decreasing transcription, increasing or decreasing translation, or otherwise effecting the amount of TIGR mRNA or protein present in a cell. They can also be used to identify compounds that affect TIGR gene expression, IOP-related disorders, or steroid sensitivity. These identified compounds can then be used to development therapeutic or diagnostic treatments, especially for glaucoma and IOP-related disorders.

The types of expression systems and reporter genes that can be used or adapted for use are well known in the art. For example, vectors containing genes for a luciferase activity, an alkaline phosphatase activity, or a green fluorescent protein activity are commonly used. See Ausubel et al., Current Protocols in Molecular Biology, John Wiley & Sons, N.Y. (1989), and supplements through May 1999. Inserting a 5' regulatory region of the TIGR gene into a vector of this type puts the expression of the reporter gene under the control of the TIGR sequence. The vector or vectors can then be inserted into various cell types to examine differences in tissue specific expression, which can then lead to identification of tissue specific factors that modulate TIGR expression as well as compounds that affect the activity of the tissue specific factors. The vectors can also be used to detect compounds that affect the transcription modulating activity of a TIGR 5' regulatory region. Alternatively, the 5' regulatory region and reporter gene constructs can be used in homologous recombination techniques to produce cells. When properly inserted into the genome of a cell, the reporter gene will be under the control of the TIGR regulatory region. Homologously recombinant cells can than be used, as discussed above, to detect changes in and modulation of expression due to various treatments or in separate cells.

For example, human trabecular meshwork cells (HTM) can be transiently or permanently transfected with a vector containing various 5' regulatory sequences from the TIGR gene that control expression of an alkaline phosphatase activity (AP). The expression of AP, or change in expression versus a control, indicates the presence of transcription-modulating sequences. By comparing the expression in HTM cells with the expression in other cells, such as Cos or HeLa cells, one can detect the presence of cell-specific compounds that influence transcriptional activity from the TIGR gene. Also, by treating the cells with test compounds, one can detect a compound that affects transcription.

Additionally, once cell types have been characterized for the presence of expression modulating activity, further uses of the 5' regulatory regions can identify the presence of specific DNA binding by cellular components or proteins within particular cells. Assays and methods for detection DNA binding include, but are not limited to, gel shift assays and equivalent techniques known in the art. In gel shift assays, the presence of a compound that binds to a DNA is detected by observing a shift in the mobility of the DNA through an agarose, polyacrylamide, or other gel matrix. Thus, by running the DNA through the gel in the presence of one or more cellular components or cell extracts and comparing to controls, specific binding to the DNA can be detected. In a similar way, various compounds can be tested for their ability to affect binding of a cellular component to the DNA by treating the sample with one or more test compounds before running the DNA through the gel. Of course, the cells used in these assays need not be primary cultured cells or established cell lines. Any type of manipulated cell can be used, even those where deliberate changes to DNA binding proteins or transcription factors contained in the cell have been made.

The TIGR gene sequences that may be used in the DNA constructs, cells, vectors, or in methods for detecting useful promoter regions, tissue or cell-specific components that bind TIGR gene sequences, or in the related methods to detect compounds affecting DNA binding or promoter activity, can be large, for example at least as big as 1.6 kb, or much smaller, on the order of about 10 to 300 bp. A preferred region is the 283 bp region from 5340 to 5044 of SEQ ID NO: 3, designated SEQ ID NO: 37, or a 227 bp region from 5044 to 5271 (end) of SED ID NO: 34, which is identified as SEQ ID NO: 38.

Other preferred regions are identified in the Figures and SEQ IDs listed or are inherently disclosed by comparing the Figures and SEQ IDs. To illustrate, the TATA boxes in SEQ ID NO: 3 and 34 both start at position 5232. Particular regions from SEQ ID NO: 3 and 34 can be correlated with the identified regulatory regions in FIG. 1, where the TATA box begins at 5230. Thus, additional preferred 5' regions can incorporate one or more regulatory regions identified and discussed herein as well as the many sequence variations given in the consensus regulatory sequences listed in FIG. 1. For example, SEQ ID NO: 37 can be changed at various places in the nGRE-Prl regulatory sequence, beginning at base 39 of SEQ ID NO: 37, to coincide with the consensus sequence given in FIG. 1. Base 67 of SEQ ID NO: 37 can be changed from T to G, and bases 57 and 65 from C to A. These changes would not effect the basic regulatory activity of these sequences, but may affect the degree of regulatory modulation possible. Similar substitutions using any one or more of the listed regulatory regions can be made to a region from SEQ ID NO: 1–3, or 34. Also, substitutions that incorporate one or more of the mutant sequences identified herein may also be made. For example, base 69 of SEQ ID NO: 37 can be changed from a T to a C to correlate with the TIGR.mt11 mutant herein. Numerous variants in the 5' regulatory regions incorporating one or both of the consensus sequences changes and the changes from the identified TIGR mutants can be made. Bases may also be added or deleted without effecting the region's basic ability to modulate expression.

The following discussion identifies some of the regulatory regions identified in the TIGR 5'region or other well known regulatory activities. As noted, these regions or sequences, or variants of them, can be incorporated into the DNA constructs, vectors, cells, and methods of the invention. Any combination of them, with or without the above identified regions in SEQ ID NO: 37 and 18, or variants thereof, can be tested for the ability to confer tissue specific, or cell-type specific expression of an attached gene. As shown in Example 5, below, SEQ ID NO: 37 confers tissue specific expression of an attached reporter gene. The expression of AP activity is much higher in the HTM cells than in HeLa or Cos cells. Thus, tissue specific promoter or regulatory activity can be identified by detecting a change of expression levels from one cell type compared to another.

Expression of the rat PRL gene is highly restricted to pituitary lactotroph cells and is induced by the cAMP-dependent protein kinase A pathway. At least one of the redundant pituitary specific elements (PRL-FP111) of the proximal rat PRL promotor is required for this protein kinase A effect (Rajnarayan et al., *Molecular Endocrinology* 4: 502–512 (1995), herein incorporated by reference). A sequence corresponding to an upstream motif or cis element characteristic of PRL-FP111 is set forth in FIG. 1 at residues 370–388 and 4491–4502, respectively. In accordance with the embodiments of the present invention, transcription of TIGR molecules can be effected by agents capable of altering the biochemical properties or concentration of molecules that bind the PRL-FP111 upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence (GR/PR), recognized by both the glucocorticoid receptor of rat liver and the progesterone receptor from rabbit uterus, has been reported to be involved in glucocorticoid and progesterone-dependent gene expression (Von der Ahe et al., *Nature* 313: 706–709 (1985), herein incorporated by reference). A sequence corresponding to a GC/PR upstream motif or cis element is set forth in FIG. 1 at residues 433–445. In accordance with the embodiments of the present invention, transcription of TIGR molecules can be effected by agents capable of altering the biochemical properties or concentration of glucocorticoid or progesterone or their homologues, including, but not limited to, the concentration of glucocorticoid or progesterone or their homologues bound to an GC/PR upstream motif or cis element. Such agents can be used in the study of glaucoma pathogenesis. In another embodiment, such agents can also be used in the study of glaucoma prognosis. In another embodiment such agents can be used in the treatment of glaucoma.

Shear stress motif (SSRE) or cis element has been identified in a number of genes including platelet-derived growth factor B chain, tissue plasminogen activator (tPA), ICAM-1 and TGF-β1 (Resnick et al., *Proc. Natl. Acad. Sci.* (USA) 80: 4591–4595 (1993), herein incorporated by reference). Transcription of these genes has been associated with humoral stimuli such as cytokines and bacterial products as well as hemodynamic stress forces. Sequences corresponding to a upstream shear stress motif or cis element are set forth in FIG. 1 at residues 446–451, 1288–1293, 3597–3602, 4771–4776, and 5240–5245, respectively. In accordance with the embodiments of the present invention, transcription of TIGR molecules can be effected by agents capable of altering the biochemical properties or concentration of molecules capable of binding the shear stress motif. Such agents can be used in the study of glaucoma pathogenesis. In another embodiment, such agents can also be used in the study of glaucoma prognosis. In another embodiment such agents can be used in the treatment of glaucoma.

A consensus sequence for a glucocorticoid response upstream motif (GRE) or cis element has been characterized (Beato, *Cell* 56:335–344 (1989); Becker et al., *Nature* 324: 686–688 (1986), herein incorporated by reference; Sakai et al., *Genes and Development* 2:1144–1154 (1988), herein incorporated by reference). Genes containing this upstream motif or cis element are regulated by glucocorticoids, progesterone, androgens and mineral corticoids (Beato, *Cell* 56: 335–344 (1989)). Sequences corresponding to glucocorticoid response upstream motif or cis element are set forth in FIG. 1 at residues 574–600, 1042–1056, 2444–2468, 2442–2269, 3536–3563, 4574–4593, 4595–4614, 4851–4865, 4844–4864, 5079–5084, and 5083–5111, respectively. In accordance with the embodiments of the present invention, transcription of TIGR molecules can be effected by agents capable of altering the biochemical properties or concentration of molecules capable of binding a glucocorticoid response upstream motif or cis element. Such agents can be used in the study of glaucoma pathogenesis. In another embodiment, such agents can also be used in the study of glaucoma prognosis. In another embodiment such agents can be used in the treatment of glaucoma.

A sequence specific binding site (CBE) for the wild type nuclear phosphoprotein, p53, has been identified and appears to be associated with replication origins (Kern et al. *Science* 252: 1708–1711 (1991), herein incorporated by reference). A sequence corresponding to an CBE upstream motif or cis element is set forth in FIG. 1 at residues 735–746. In accordance with the embodiments of the present invention, transcription of TIGR molecules can be effected by agents capable of altering the biochemical properties or concentration of p53 or its homologues, including, but not limited to, the concentration of p53 or its homologues bound to an CBE upstream motif or cis element. Such agents can be used in the study of glaucoma pathogenesis. In another embodiment, such agents can also be used in the study of glaucoma prognosis. In another embodiment such agents can be used in the treatment of glaucoma.

Nuclear factor ets-like (NFE), a transcriptional activator that facilitates p50 and c-Rel-dependent IgH 3' enhancer activity has been shown to bind to an NFE site in the Rel-dependent IgH 3' enhancer (Linderson et al., *European J. Immunology* 27:468–475 (1997), herein incorporated by reference). A sequence corresponding to an NFE upstream motif or cis element is set forth in FIG. 1 at residues 774–795. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an NFE upstream motif or cis element. Such agents can be used in the study of glaucoma pathogenesis. In another embodiment, such agents can also be used in the study of glaucoma prognosis. In another embodiment such agents can be used in the treatment of glaucoma.

An upstream motif or cis element (KTF.1-CS) for a control element 3' to the human keratin 1 gene that regulates cell type and differentiation-specific expression has been identified (Huff et al., *J. Biological Chemistry* 268:377–384 (1993), herein incorporated by reference). A sequence corresponding to an upstream motif or cis element characteristic of KTF.1-CS is set forth in FIG. 1 at residues 843–854. In accordance with the embodiments of the present invention, transcription of TIGR molecules can be effected by agents capable of altering the biochemical properties or concentration of KTF.1-CS or its homologues, including, but not limited to, the concentration of KTF.1-CS or its homologues bound to a KTF.1-CS upstream motif or cis element Such agents can be used in the study of glaucoma pathogenesis. In another embodiment, such agents can also be used in the study of glaucoma prognosis. In another embodiment such agents can be used in the treatment of glaucoma.

A progesterone responsive element (PRE) that maps to the far upstream steroid dependent DNase hypersensitive site of chicken lysozyme chromatin has been characterized (Hecht et al., *EMBO J.* 7:2063–2073 (1988), herein incorporated by reference). The element confers hormonal regulation to a heterologous promoter and is composed of a cluster of progesterone receptor binding sites. A sequence corresponding to an upstream motif or cis element characteristic of PRE is set forth in FIG. 1 at residues 987–1026. In accordance with the embodiments of the present invention, transcription of TIGR molecules can be effected by agents capable of altering the biochemical properties or concentration of molecules capable of binding a progesterone responsive PRE upstream motif or cis element. Such agents may be useful in the study of glaucoma pathogenesis. In another embodiment, such agents can also be used in the study of glaucoma prognosis. In another embodiment such agents can be used in the treatment of glaucoma.

A sequence (ETF-EGFR) has been characterized which serves as a motif for a transactive transcription factor that regulates expression of the epidermal growth factor receptor (Regec et al., *Blood* 85:2711–2719 (1995), herein incorporated by reference). A sequence corresponding to an ETF-EGFR upstream motif or cis element is set forth in FIG. 1 at residues 1373–1388. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an ETF-EGFR upstream motif or cis element. Such agents can be used in the study of glaucoma pathogenesis. In another embodiment, such agents can also be used in the study of glaucoma prognosis. In another embodiment such agents can be used in the treatment of glaucoma.

A common trans-acting factor (SRE-cFos) has been shown to regulate skeletal and cardiac alpha-Actin gene transcription in muscle (Muscat et al., *Molecular and Cellular Biology* 10:4120–4133 (1988), herein incorporated by reference). A sequence corresponding to an SRE-cFos upstream motif or cis element is set forth in FIG. 1 at residues 1447–1456. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an SRE-cFos upstream motif or cis element. Such agents can be used in the study of glaucoma pathogenesis. In another embodiment, such agents can also be used in the study of glaucoma prognosis. In another embodiment such agents can be used in the treatment of glaucoma.

Alu repetitive elements are unique to primates and are interspersed within the human genome with an average spacing of 4Kb. While some Alu sequences are actively transcribed by polymerase Im, normal transcripts may also contain Alu-derived sequences in 5' or 3' untranslated regions (Jurka and Mikahanljaia, *J. Mol. Evolution* 32:105–121 (1991), herein incorporated by reference, Claveria and Makalowski, *Nature* 371:751–752 (1994), herein incorporated by reference). A sequence corresponding to an Alu upstream motif or cis element is set forth in FIG. 1 at residues 1331–1550. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an Alu upstream motif or cis element. Such agents can be used in the study of glaucoma pathogenesis. hn another embodiment, such agents can also be used in the study of glaucoma prognosis. In another embodiment such agents can be used in the treatment of glaucoma.

A consensus sequence for a vitellogenin gene-binding protein (VBP) upstream motif or cis element has been characterized (Iyer et al., *Molecular and Cellular Biology* 11:4863–4875 (1991), herein incorporated by reference). Expression of the VBP gene commences early in liver ontogeny and is not subject to circadian control. A sequence corresponding to an upstream motif or cis element capable of binding VBP is set forth in FIG. 1 at residues 1786–1797. In accordance with the embodiments of the present invention, transcription of TIGR molecules can be effected by agents capable of altering the biochemical properties or concentration of VBP or its homologues, including, but not limited to, the concentration of VBP or its homologues bound to an VBP upstream motif or cis element Such agents can be used in the study of glaucoma pathogenesis. In another embodiment, such agents can also be used in the study of glaucoma prognosis. In another embodiment such agents can be used in the treatment of glaucoma.

A structural motif (Malt-CS) or cis element involved in the activation of all promoters of the maltose operons in *Escherichia coli* and *Klebsiella pneumoniae* has been characterized (Vidal-Ingigliardi et al., *J. Mol. Biol.* 218:323–334 (1991), herein incorporated by reference). A sequence corresponding to a upstream Malt-CS motif or cis element is set forth in FIG. 1 at residues 1832–1841. In accordance with the embodiments of the present invention, transcription of TIGR molecules can be effected by agents capable of altering the biochemical properties or concentration of molecules capable of binding the upstream Malt-CS motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for an estrogen receptor upstream motif or cis element has been characterized (ERE) (Forman et al., *Mol. Endocrinology* 4:1293–1301 (1990), herein incorporated by reference; de Vemeuil et al., *Nucleic Acid Res*. 18:4489–4497 (1990), herein incorporated by reference; Gaub et al., *Cell* 63:1267–1276 (1990), herein incorporated by reference. A sequence corresponding to half an upstream motif or cis element capable of binding estrogen receptor is set forth in FIG. 1 at residues 2166–2195, 3413–3429, and 3892–3896, respectively. In accordance with the embodiments of the present invention, transcription of TIGR molecules can be effected by agents capable of altering the biochemical properties or concentration, of the estrogen receptor or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Certain protein-binding sites (NF-mutagen) in Ig gene enhancers which determine transcriptional activity and inducibility have been shown to interact with nuclear factors (Lenardo et al., *Science* 236:1573–1577 (1987), herein incorporated by reference). A sequence corresponding to an NF-mutagen upstream motif or cis element is set forth in FIG. 1 at residues 2329–2338. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an NF-mutagen upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for a transcriptional repressor of c-myc (myc-PRF) upstream motif or cis element has been identified (Kakkis et al., *Nature* 339:718–719 (1989), herein incorporated by reference). Myc-PRF interacts with another widely distributed protein, myc-CF1 (common factor 1), which binds nearby and this association may be important in myc-PRF repression. A sequence corresponding to an upstream motif or cis element capable of binding myc-PRF is set forth in FIG. 1 at residues 2403–2416. In accordance with the embodiments of the present invention, transcription of TIGR molecules can be effected by agents capable of altering the biochemical properties or concentration of myc-PRF or its homologues, including, but not limited to, the concentration of myc-PRF or its homologues bound to an myc-PRF upstream motif or cis element Such agents can be used in the study of glaucoma pathogenesis. In another embodiment, such agents can also be used in the study of glaucoma prognosis. In another embodiment such agents can be used in the treatment of glaucoma.

Human transcription factor activator protein 2 (AP2) is a transcription factor that has been shown to bind to Sp1, nuclear factor 1 (NF1) and simian virus 40 transplantation (SV40 T) antigen binding sites. It is developmentally regulated (Williams and Tijan, *Gene Dev*. 5: 670–682 (1991), herein incorporated by reference; Mitchell et al., *Genes Dev*. 5:105–119 (1991), herein incorporated by reference; Coutois et al., *Nucleic Acid Research* 18:57–64 (1990), herein incorporated by reference; Comb et al., *Nucleic Acid Research* 18:3975–3982 (1990), herein incorporated by reference; Winings et al., *Nucleic Acid Research* 19:3709–3714 (1991), herein incorporated by reference). Sequences corresponding to an upstream motif or cis element capable of binding AP2 are set forth in FIG. 1 at residues 2520–2535, and 5170–5187, respectively. In accordance with the embodiments of the present invention, transcription of TIGR molecules can be effected by agents capable of altering the biochemical properties or concentration of AP2 or its homologues, including, but not limited to, the concentration of AP2 or its homologues bound to an upstream motif or cis element. Such agents may be useful in the study of glaucoma pathogenesis. In another embodiment, such agents can also be used in the study of glaucoma prognosis. In another embodiment such agents can be used in the treatment of glaucoma.

Drosophila RNA polymerase II heat shock transcription factor (HSTF) is a transcription factor that has been shown to be required for active transcription of an hsp 70 gene (Parker and Topol, *Cell* 37:273–283 (1984), herein incorporated by reference). Sequences corresponding to an upstream motif or cis element capable of binding HSTF are set forth in FIG. 1 at residues 2622–2635, and 5105–5132. In accordance with the embodiments of the present invention, transcription of TIGR molecules can be effected by agents capable of altering the biochemical properties or concentration of HSTF or its homologues, including, but not limited to, the concentration of HSTF or its homologues bound to an HSTF upstream motif or cis element. Such agents can be used in the study of glaucoma pathogenesis. In another embodiment, such agents can also be used in the study of glaucoma prognosis. In another embodiment such agents can be used in the treatment of glaucoma.

A sequence corresponding to an upstream motif or cis element characteristic of SBF is set forth in FIG. 1 at residues 2733–2743 (Shore et al., *EMBO J*. 6:461–467 (1987), herein incorporated by reference). In accordance with the embodiments of the present invention, transcription of TIGR molecules can be effected by agents capable of altering the biochemical properties or concentration of molecules that bind the SBF upstream motif or cis element. Such agents can be used in the study of glaucoma pathogenesis. In another embodiment, such agents can also be used in the study of glaucoma prognosis. In another embodiment such agents can be used in the treatment of glaucoma.

An NF1 motif or cis element has been identified which recognizes a family of at least six proteins (Courtois, et al., *Nucleic Acid Res*. 18:57–64 (1990), herein incorporated by reference; Mul et al., *J. Virol*. 64:5510–5518 (1990), herein incorporated by reference; Rossi et al., *Cell* 52: 405–414 (1988), herein incorporated by reference; Gounari et al., *EMBO J*. 10:559–566 (1990), herein incorporated by reference; Goyal et al., *Mol. Cell Biol*. 10:1041–1048 (1990); herein incorporated by reference; Mermond et al., *Nature* 332:557–561 (1988), herein incorporated by reference; Gronostajski et al., *Molecular and Cellular Biology* 5:964–971 (1985), herein incorporated by reference; Hennighausen et al., *EMBO J*. 5:1367–1371 (1986), herein incorporated by reference; Chodosh et al., *Cell* 53:11–24 (1988), herein incorporated by reference). The NF1 protein will bind to an NF1 motif or cis element either as a dimer (if the motif is palindromic) or as an single molecule (if the motif is not palindromic). The NF1 protein is induced by TGFβ (Faisst and Meyer, *Nucleic Acid Research* 20:3–26 (1992), herein incorporated by reference). Sequences corresponding to an upstream motif or cis element capable of binding NF1 are set forth in FIG. 1 at residues 2923–2938, 4143–4167, and 4886–4900, respectively. In accordance with the embodiments of the present invention, transcription of TIGR molecules can be effected by agents capable of altering the biochemical properties or concentration of NF1 or its homologues, including, but not limited to, the concentration of NF1 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Conserved regulatory sequences (NF-MHCIIA/B) of a rabbit major histocompatability complex (MHC) class II gene are responsible for binding two distinct nuclear factors NF-MHCIIA and NF-MHCIIB and are believed to be involved in the regulation of coordinate expression of the class II genes—eg. MHC class II gene in B lymphocytes (Sittisombut *Molecular and Cellular Biology* 5:2034–2041 (1988), herein incorporated by reference). A sequence corresponding to an NF-MHCIILAB upstream motif or cis element is set forth in FIG. 1 at residues 2936–2944. In accordance with the embodiments of the present invention, transcription of TIGR molecules can be effected by agents capable of altering the biochemical properties or concentration of NF-MHCIIA or NF-MHCIIB or their homologues, including, but not limited to, the concentration of NF-MHCIIA or NF-MICIIB or their homologues bound to an NF-MHCIIA/B upstream motif or cis element. Such agents can be used in the study of glaucoma pathogenesis. In another embodiment, such agents can also be used in the study of glaucoma prognosis. In another embodiment such agents can be used in the treatment of glaucoma.

PEA 1 binding motifs or cis elements have been identified (Piette and Yaniv, *EMBO J.* 5:1331–1337 (1987), herein incorporated by reference). The PEA1 protein is a transcription factor that is reported to bind to both the polyoma virus and c-fos enhancers. A sequence corresponding to an upstream motif or cis element capable of binding PEAL is set forth in FIG. 1 at residues 3285–3298. In accordance with the embodiments of the present invention, transcription of TIGR molecules can be effected by agents capable of altering the biochemical properties or concentration of PEA1 or its homologues, including, but not limited to, the concentration of PEA1 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

A conserved cis-acting regulatory element (ICS) has been shown to bind trans-acting constituitive nuclear factors present in lymphocytes and fibroblasts which are involved in the interferon (IFN)-mediated transcriptional enhancement of MHC class I and other genes (Shirayoshi et al., *Proc. Natl. Acad. Sci.* (*USA*) 85:5884–5888 (1988), herein incorporated by reference). A sequence corresponding to an ICS upstream motif or cis element is set forth in FIG. 1 at residues 3688–3699. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an ICS upstream motif or cis element. Such agents can be used in the study of glaucoma pathogenesis. In another embodiment, such agents can also be used in the study of glaucoma prognosis. In another embodiment such agents can be used in the treatment of glaucoma.

A consensus sequence for an ISGF2 upstream motif or cis element has been characterized (Iman et al., *Nucleic Acids Res.* 18:6573–6580 (1990), herein incorporated by reference; Harada et al., *Cell* 63:303–312 (1990), herein incorporated by reference; Yu-Lee et al., *Mol. Cell Biol.* 10:3087–3094 (1990), herein incorporated by reference; Pine et al., *Mol. Cell Biol.* 10: 32448–2457 (1990), herein incorporated by reference). ISGF2 is induced by interferon $\alpha$ and $\gamma$, prolactin and virus infections. A sequence corresponding to an upstream motif or cis element capable of binding ISGF2 is set forth in FIG. 1 at residues 4170–4179. In accordance with the embodiments of the present invention, transcription of TIGR molecules can be effected by agents capable of altering the biochemical properties or concentration of ISGF2 or its homologues, including, but not limited to, the concentration of ISGF2 or its homologues bound to an upstream motif or cis element Such agents can be used in the study of glaucoma pathogenesis. In another embodiment, such agents can also be used in the study of glaucoma prognosis. In another embodiment such agents can be used in the treatment of glaucoma.

A sequence corresponding to an upstream motif or cis element capable of binding zinc is set forth in FIG. 1 at residues 4285–4292. In accordance with the embodiments of the present invention, transcription of TIGR molecules can be effected by agents capable of altering the biochemical properties or concentration of zinc. Such agents can be used in the study of glaucoma pathogenesis. In another embodiment, such agents can also be used in the study of glaucoma prognosis. In another embodiment such agents can be used in the treatment of glaucoma.

A sequence corresponding to an upstream motif or cis element characteristic of CAP/CRP-galO is set forth in FIG. 1 at residues 4379–4404 (Taniguchi et al., *Proc. Natl. Acad. Sci* (USA) 76:5090–5094 (1979), herein incorporated by reference). In accordance with the embodiments of the present invention, transcription of TIGR molecules can be effected by agents capable of altering the biochemical properties or concentration of molecules that bind the CAP/CRP-galO upstream motif or cis element. Such agents can be used in the study of glaucoma pathogenesis. In another embodiment, such agents can also be used in the study of glaucoma prognosis. In another embodiment such agents can be used in the treatment of glaucoma.

Human transcription factor activator protein 1 (AP1) is a transcription factor that has been shown to regulate genes which are highly expressed in transformed cells such as stromelysin, c-fos, $\alpha_1$-anti-trypsin and collagenase (Gutman and Wasylyk, *EMBO J.* 9.7: 2241–2246 (1990), herein incorporated by reference; Martin et al., *Proc. Natl. Acad. Sci. USA* 85: 5839–5843 (1988), herein incorporated by reference; Jones et al., *Genes and Development* 2: 267–281 (1988), herein incorporated by reference; Faisst and Meyer, *Nucleic Acid Research* 20: 3–26 (1992), herein incorporated by reference; Kim et al., *Molecular and Cellular Biology* 10: 1492–1497 (1990), herein incorporated by reference: Baumhueter et al., *EMBO J.* 7:2485–2493 (1988), herein incorporated by reference). The AP1 transcription factor has been associated with genes that are activated by 12-O-tetradecanolyphorbol-13-acetate (TPA) (Gutman and Wasylyk, *EMBO J.* 7:2241–2246 (1990)). Sequences corresponding to an upstream motif or cis element capable of binding AP1 are set forth in FIG. 1 at residues 4428–4434 and 4627–4639, respectively. In accordance with the embodiments of the present invention, transcription of TIGR molecules can be effected by agents capable of altering the biochemical properties or concentration of AP1 or its homologues, including, but not limited to, the concentration of AP1 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

The sex-determining region of the Y chromosome gene, sry, is expressed in the fetal mouse for a brief period, just prior to testis differentiation. SRY is a DNA binding protein known to bind to a CACA-rich region in the sry gene (Vriz et al., *Biochemistry and Molecular Biology International* 37:1137–1146 (1995), herein incorporated by reference). A sequence corresponding to an upstream motif or cis element capable of binding SRY is set forth in FIG. 1 at residues 4625–4634. In accordance with the embodiments of the present invention, transcription of TIGR molecules can be effected by agents capable of altering the biochemical properties or concentration of SRY or its homologues, including, but not limited to, the concentration of SRY or its homologues bound to an upstream motif or cis element. Such agents may be useful in the study of glaucoma pathogenesis. In another embodiment, such agents can also be used in the study of glaucoma prognosis. In another embodiment such agents can be used in the treatment of glaucoma.

A sequence corresponding to an upstream motif or cis element characteristic of GC2-GH is set forth in FIG. 1 at residues 4689–4711 (West et al., *Molecular and Cellular Biology* 7: 1193–1197 (1987), herein incorporated by reference). In accordance with the embodiments of the present invention, transcription of TIGR molecules can be effected by agents capable of altering the biochemical properties or concentration of GC2-GH or its homologues, including, but not limited to, the concentration of GC2-GH or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

PEA3 binding motifs or cis elements have been identified (Martin et al., *Proc. Natl. Acad. Sci.* (*USA*) 85:5839–5843 (1988), herein incorporated by reference; Gutman and Wasylyk, *EMBO J*: 7:2241–2246 (1990), herein incorporated by reference). The PEA3 protein is a transcription factor that is reported to interact with AP1 like proteins (Martin et al., *Proc. Natl. Acad. Sci.* (*USA*) 85:5839–5843 (1988), herein incorporated by reference). Sequences corresponding to an upstream motif or cis element capable of binding PEA3 is set forth in FIG. 1 at residues 4765–4769. In accordance with the embodiments of the present invention, transcription of TIGR molecules can be effected by agents capable of altering the biochemical properties or concentration of PEA3 or its homologues, including, but not limited to, the concentration of PEA3 or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Mammalian interspersed repetitive (MIR) is an element involved in the coding and processing sequences of mammalian genes. The MIR element is at least 260 bp in length and numbers about $10^5$ copies within the mammalian genome (Mumane et al., *Nucleic Acids Research* 15:2837–2839 (1995), herein incorporated by reference). A sequence corresponding to an MIR upstream motif or cis element is set forth in FIG. 1 at residues 4759–4954. In accordance with the embodiments of the present invention, transcription of TIGR molecules can be effected by agents capable of altering the biochemical properties or concentration of nuclear factors or their homologues, including, but not limited to, the concentration of nuclear factors or their homologues bound to an MIR upstream motif or cis element. Such agents can be used in the study of glaucoma pathogenesis. In another embodiment, such agents can also be used in the study of glaucoma prognosis. In another embodiment such agents can be used in the treatment of glaucoma.

Normal liver and differentiated hepatoma cell lines contain a hepatocyte-specific nuclear factor (HNF-1) which binds cis-acting element sequences within the promoters of the alpha and beta chains of fibrinogen and alpha 1-antitrypsin (Baumhueter et al., *EMBO J.* 8:2485–2493, herein incorporated by reference). A sequence corresponding to an HNF- 1 upstream motif or cis element is set forth in FIG. 1 at residues 4923–4941. In accordance with the embodiments of the present invention, transcription of TIGR molecules can be effected by agents capable of altering the biochemical properties or concentration of HNF-1 or its homologues, including, but not limited to, the concentration of HNF-1 or its homologues bound to an HNF-1 upstream motif or cis element. Such agents can be used in the study of glaucoma pathogenesis. In another embodiment, such agents can also be used in the study of glaucoma prognosis. In another embodiment such agents can be used in the treatment of glaucoma.

A number of cis elements or upstream motifs have been associated with gene regulation by steroid and thyroid hormones (e.g. glucocorticoid and estrogen)(Beato, *Cell* 56:335–344 (1989), herein incorporated by reference; Brent et al., *Molecular Endocrinology* 89:1996–2000 (1989), herein incorporated by reference; Glass et al., *Cell* 54:313–323 (1988), herein incorporated by reference; Evans, *Science* 240:889–895 (1988), herein incorporated by reference).

A consensus sequence for a thyroid receptor upstream motif or cis element (TRE) has been characterized (Beato, *Cell* 56:335–344 (1989), herein incorporated by reference). A sequence corresponding to a thyroid receptor upstream motif or cis element is set forth in FIG. 1 at residues 5151–5156. Thyroid hormones are capable of regulating genes containing a thyroid receptor upstream motif or cis element (Glass et al., *Cell* 54:313–323 (1988), herein incorporated by reference). Thyroid hormones can negatively regulate TIGR. In accordance with the embodiments of the present invention, transcription of TIGR molecules can be effected by agents capable of altering the biochemical properties or concentration of molecules capable of binding a thyroid receptor upstream motif or cis element. Such agents can be used in the study of glaucoma pathogenesis. In another embodiment, such agents can also be used in the study of glaucoma prognosis. In another embodiment such agents can be used in the treatment of glaucoma.

NFκB is a transcription factor that is reportedly associated with a number of biological processes including T-cell activation and cytokine regulation (Lenardo et al., *Cell* 58:227–229 (1989), herein incorporated by reference). A consensus upstream motif or cis element capable of binding NFκB has been reported (Lenardo et al., *Cell* 58:227–229 (1989)). Sequences corresponding to an upstream motif or cis element capable of binding NFKdB are set forth in FIG.

1 at residues 5166–5175. In accordance with the embodiments of the present invention, transcription of TIGR molecules can be effected by agents capable of altering the biochemical properties or concentration of NFκB or its homologues, including, but not limited to, the concentration of NFκB or its homologues bound to an upstream motif or cis element. Such agents can be used in the study of glaucoma pathogenesis. In another embodiment, such agents can also be used in the study of glaucoma prognosis. In another embodiment such agents can be used in the treatment of glaucoma.

Illustrative Uses of the Nucleic Acids of the Invention

Where one or more of the agents is a nucleic acid molecule, such nucleic acid molecule may be sense, antisense or triplex oligonucleotides corresponding to any part of the TIGR promoter, TIGR cDNA, TIGR intron, TIGR exon or TIGR gene. In some embodiments these nucleic acids may be about 20 bases in length, as for example, SEQ. ID NO: 6–25 or 33. In some circmstances, the nucleic acids may be only about 8 bases in length. Short nucleic acids may be particularly useful in hybridization to immobilized nucleic acids in order to determine the presence of specific sequences, such as by the known methods of sequencing by hybridization.

The TIGR promoter, or fragment thereof, of the present invention may be cloned into a suitable vector and utilized to promote the expression of a marker gene (e.g. firefly luciferase (de Wet, *Mol. Cell Biol.* 7:725–737 (1987), herein incorporated by reference) or GUS (Jefferson et al., *EMBO J.* 6:3901–3907 (1987), herein incorporated by reference)).

In another embodiment of the present invention, a TIGR promoter may be cloned into a suitable vector and utilized to promote the expression of a TIGR gene in a suitable eukaryotic or prokaryotic host cell (e.g. human trabecular cell, chinese hamster cell, *E. coli*). In another embodiment of the present invention, a TIGR promoter may be cloned into a suitable vector and utilized to promote the expression of a homologous or heterologous gene in a suitable eukaryotic or prokaryotic host cells (e.g. human trabecular cell lines, chinese hamster cells, *E. coli*).

Similarly, the TIGR promoter, regions of the TIGR 5' regulatory region from about 10 bp to about 1.6 kb, or regions of the TIGR 5' regulatory region that confer tissue specific expression can be used in DNA constructs, vectors, and cells to express an operably linked gene. For example, these TIGR sequences can control expression of a linked gene in a vector used for producing transgenic animals. In this way, cells or animals can be produced that express a gene in a tissue specific manner. One embodiment involves a gene therapy approach to treating glaucoma or IOP-disorder, where a transgene having the TIGR 5'regulatory sequence is used to direct expression of a therapeutic gene into the trabecular meshwork or the cells of the trabecular meshwork. Experimental animal models can also be produced using the transgenic technology. These animal models, or cells from them or comprising these TIGR sequences, can be used in methods to screen for compounds that modulate expression of TIGR, and especially compounds that affect the steroid regulation of TIGR expression. These methods will produce therapeutic or diagnostic agents, which agents are specifically included in the invention.

Thus, transgenic animals having an introduced DNA that comprises at least a portion of the TIGR 5' regulatory region are specifically included in this invention. Preferred embodiments have 5' regulatory sequences of SEQ ID NO: 37 or 38, or variant thereof, or a region of SEQ ID NO: 3 or 34, especially those that confer tissue specific expression. One skilled in the art is familiar with the production of transgenic construct, vectors, and animals (See, Ausubel et al., Current Protocols in Molecular Biology).

In addition, as noted above, the 5' regulatory regions can be used to screen and identify DNA binding proteins. The specific binding of proteins or cellular components to the 5' regulatory regions can be detected, see Example 5. Screening methods for compounds that modulate the binding can also be produced using the 5' regulatory regions of the invention, or vectors or cells comprising those regions. DNA binding proteins that increase or decrease expression can be identified. For example, cells that do not show native expression of TIGR, such as HeLa cells, may possess proteins or cellular components that inhibit expression of TIGR. While cells like TM cells may possess DNA binding proteins or cellular components that allow expression of TIGR or increase the level of TIGR expression in response to other agents, such as steroids or dexamethasone. Thus, the invention encompasses a number of methods to detect and identify proteins or cellular components that modulate expression of TIGR, or the expression of a gene under the control of the TIGR 5' regulatory region. Also, methods to detect compounds that effect that modulation are similarly encompassed, as well as therapeutic and diagnostic agents that are identified from those methods.

Practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., In *Molecular Cloning: A Laboratory Manual*, Cold Spring Harbor Press (1989), herein incorporated by reference in its entirety; Old and Primrose, In Principles of Gene Manipulation: An Introduction To Genetic Engineering, Blackwell (1994), herein incorporated by reference).

The TIGR promoter, or any portion thereof, or an about 10 to about 500 bases fragment thereof, of the present invention may be used in a gel-retardation or band shift assay (Old and Primrose, In Principles of Gene Manipulation: An Introduction To Genetic Engineering, Blackwell (1994)). Nucleic acids or fragments comprising any of the cis elements identified in the present invention may be used in a gel-retardation or band shift assay to isolate proteins capable of binding the cis element. Suitable DNA fragments or molecules comprise or consist of one or more of the following: sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEA 1 as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175.

A preferred class of agents of the present invention comprises nucleic acid molecules encompassing all or a fragment of the "TIGR promoter" or 5' flanking gene sequences. As used herein, the terms "TIGR promoter" or "promoter" is used in an expansive sense to refer to the regulatory sequence(s) that control mRNA production. Thus, TIGR promoter sequences can be identified by those sequences that functionally effect the intiation, rate, or amount of transcription of the TIGR gene product mRNA. Such sequences include RNA polymerase binding sites, glucocorticoid response elements, enhancers, etc. These sequences may preferably be found within the specifically disclosed 5' upstream region sequences disclosed here, and most preferably within an about 500 base region 5' to the start of transcription or within an about 300 base region 5' of the transcription start site. However, other genomic sequences may be a TIGR promoter. Methods known in the art to identify distant promoter elements can be used with the disclosed sequences and nucleic acids to identify and define these distant TIGR promoter sequences. Such TIGR molecules may be used to diagnose the presence of glaucoma and the severity of or susceptibility to glaucoma. Such molecules may be either DNA or RNA.

A functional regulatory region of the TIGR gene may be a TIGR promoter sequence. It may also include transcription enhancer sites and transcription inhibitor sites or binding sites for a number of known proteins or molecules demonstrated as effecting transcription. A number of regulatory elements are discussed below, and the equivalent of those activities can represent the functional regulatory region of the TIGR gene. The methods for identifying and detecting the activity and function of these regulatory regions are known in the art.

Fragment nucleic acid molecules may encode significant portion(s) of, or indeed most of, SEQ ID NO: 1 or SEQ ID NO: 3 or SEQ ID NO: 4 or SEQ ID NO: 5. Alternatively, the fragments may comprise smaller oligonucleotides (having from about 15 to about 250 nucleotide residues, and more preferably, about 15 to about 30 nucleotide residues.). Such oligonucleotides include SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25.

Alternatively such oligonucleotides may derive from either the TIGR promoter, TIGR introns, TIGR exons, TIGR cDNA and TIGR downstream sequences comprise or consist of one or more of the following: sequences corresponding to an upstream motif or cis element characteristic of PRLFP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEA1 as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175. For such purpose, the oligonucleotides must be capable of specifically hybridizing to a nucleic acid molecule genetically or physically linked to the TIGR gene. As used herein, the term "linked" refers to genetically, physically or operably linked.

As used herein, two nucleic acid molecules are said to be capable of specifically hybridizing to one another if the two molecules are capable of forming an anti-parallel, double-stranded nucleic acid structure, whereas they are unable to form a double-stranded structure when incubated with a non-TIGR nucleic acid molecule. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook, J., et al., (In: *Molecular Cloning, a Laboratory Manual*, *2nd Edition*, Cold Spring Harbor Press, Cold Spring Harbor, N.Y. (1989)), and by Haymes, B. D., et al. (In: *Nucleic Acid Hybridization, A Practical Approach*, IRL Press, Washington, D.C. (1985)), both herein incorporated by reference). Departures from complete complementarity are therefore permissible, as long as such departures do not completely preclude the capacity of the molecules to form a double-stranded structure. Thus, in order for an oligonucleotide to serve as a primer it need only be sufficiently complementary in sequence to be able to form a stable double-stranded structure under the particular solvent and salt concentrations employed.

Apart from their diagnostic or prognostic uses, such oligonucleotides may be employed to obtain other TIGR nucleic acid molecules. Such molecules include the TIGR-encoding nucleic acid molecule of non-human animals (particularly, cats, monkeys, rodents and dogs), fragments thereof, as well as their promoters and flanking sequences. Such molecules can be readily obtained by using the above-described primers to screen cDNA or genomic libraries obtained from non-human species. Methods for forming such libraries are well known in the art. Such analogs may differ in their nucleotide sequences from that of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: I1, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or from molecules consisting of sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream otif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEA1 as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 because complete complementarity is not needed for stable hybridization. The TIGR nucleic acid molecules of the present invention therefore also include molecules that, although capable of specifically hybridizing with TIGR nucleic acid molecules may lack "complete complementarity." Any of a variety of methods may be used to obtain the above-described nucleic acid molecules (Elles, Methods in Molecular Medicine: Molecular Diagnosis of Genetic Diseases, Humana Press (1996), herein incorporated by reference). SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8,SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 33, sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEA1 as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 may be used to synthesize all or any portion of the TIGR promoter or any of the TIGR upstream motifs or portions the TIGR cDNA (Zamechik et al, *Proc. Natl. Acad. Sci.* (*U.S.A.*) 83:4143 (1986); Goodchild et al., *Proc. Natl. Acad. Sci.* (*U.S.A.*) 85:5507 (1988); Wickstrom et al., *Proc. Natl. Acad. Sci.* (*U.S.A.*) 85:1028; Holt, J. T. et al., *Molec. Cell. Biol.* 8:963 (1988); Gerwirtz, A. M. et al., *Science* 242:1303 (1988); Anfossi, G., et al., *Proc. Natl. Acad. Sci.* (*U.S.A.*) 86:3379 (1989); Becker, D., et al., *EMBO J.* 8:3679 (1989); all of which references are incorporated herein by reference).

Automated nucleic acid synthesizers may be employed for this purpose. In lieu of such synthesis, the disclosed SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14,SEQID NO: 15,SEQID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 33, sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786–1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAl as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 may be used to define a pair of primers that can be used with the polymerase chain reaction (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)) to amplify and obtain any desired TIGR gene DNA molecule or fragment.

The TIGR promoter sequence(s) and TIGR flanking sequences can also be obtained by incubating oligonucleotide probes of TIGR oligonucleotides with members of genomic human libraries and recovering clones that hybridize to the probes. In a second embodiment, methods of "chromosome walking," or 3' or 5' RACE may be used (Frohman, M. A. et al., *Proc. Natl. Acad. Sci.* (*U.S.A.*) 85: 8998–9002 (1988), herein incorporated by reference); Ohara, O. et al., *Proc. Natl. Acad. Sci.* (*U.S.A.*) 86:5673–5677 (1989), herein incorporated by reference) to obtain such sequences.

II. Uses of the Molecules of the Invention in the Diagnosis and Prognosis of Glaucoma and Related Diseases A particularly desired use of the present invention relates to the diagnosis of glaucoma, POAG, pigmentary glaucoma, high tension glaucoma and low tension glaucoma and their related diseases. Another particularly desired use of the present invention relates to the prognosis of glaucoma, POAG, pigmentary glaucoma, high tension glaucoma and low tension glaucoma and their related diseases. As used herein the term "glaucoma" includes both primary glaucomas, secondary glaucomas, juvenile glaucomas, congenital glaucomas, and familial glaucomas, including, without limitation, pigmentary glaucoma, high tension glaucoma and low tension glaucoma and their related diseases. As indicated above, methods for diagnosing or prognosing glaucoma suffer from inaccuracy, or require multiple examinations. The molecules of the present invention may be used to define superior assays for glaucoma. Quite apart from such usage, the molecules of the present invention may be used to diagnosis or predict an individual's sensitivity to elevated intraocular pressure upon administration of steroids such as glucocorticoids or corticosteroids, or anti-inflammatory steroids). Dexamethasone, cortisol and prednisolone are preferred steroids for this purpose. Medical conditions such as inflammatory and allergic disorders, as well as organ transplantation recipients, benefit from treatment with glucocorticoids. Certain individuals exhibit an increased IOP response to such steroids (i.e., "steroid sensitivity"), which is manifested by an undesired increase in intraocular pressure. The present invention may be employed to diagnosis or predict such sensitivity, as well as glaucoma and related diseases.

In a first embodiment, the TIGR molecules of the present invention are used to determine whether an individual has a mutation affecting the level (i.e., the concentration of TIGR mRNA or protein in a sample, etc.) or pattern (i.e., the kinetics of expression, rate of decomposition, stability profile, etc.) of the TIGR expression (collectively, the "TIGR response" of a cell or bodily fluid) (for example, a mutation in the TIGR gene, or in a regulatory region(s) or other gene(s) that control or affect the expression of TIGR), and being predictive of individuals who would be predisposed to glaucoma (prognosis), related diseases, or steroid sensitivity. As used herein, the TIGR response manifested by a cell or bodily fluid is said to be "altered" if it differs from the TIGR response of cells or of bodily fluids of normal individuals. Such alteration may be manifested by either abnormally increased or abnormally diminished TIGR response. To determine whether a TIGR response is altered, the TIGR response manifested by the cell or bodily fluid of the patient is compared with that of a similar cell sample (or bodily fluid sample) of normal individuals. As will be appreciated, it is not necessary to re-determine the TIGR response of the cell sample (or bodily fluid sample) of normal individuals each time such a comparison is made; rather, the TIGR response of a particular individual may be compared with previously obtained values of normal individuals.

In one sub-embodiment, such an analysis is conducted by determining the presence and/or identity of polymorphism (s) in the TIGR gene or its flanking regions which are associated with glaucoma, or a predisposition (prognosis) to glaucoma, related diseases, or steroid sensitivity. As used herein, the term "TIGR flanking regions" refers to those regions which are located either upstream or downstream of the TIGR coding region.

Any of a variety of molecules can be used to identify such polymorphism(s). In one embodiment, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 33, sequences corresponding to an upstream motif or cis element characteristic of PRL-FP111 as set forth in FIG. 1 at residues 370–388, and 4491–4502, respectively, a sequence corresponding to an upstream motif or cis element capable of binding GR/PR as set forth in FIG. 1 at residues 433–445, sequences corresponding to an upstream shear stress motif or cis element as set forth in FIG. 1 at residues 446–451, 1288–1293, 3597–3602, 4771–4776, and 5240–5245, respectively, sequences corresponding to glucocorticoid response upstream motif or cis element as set forth in FIG. 1 at residues 574–600, 1042–1056, 2444–2468, 2442–2269, 3536–3563, 4574–4593, 4595–4614, 4851–4865, 4844–4864, 5079–5084, 5083–5111, respectively, a sequence corresponding to an upstream motif or cis element capable of binding CBE as set forth in FIG. 1 at residues 735–746, a sequence corresponding to an upstream motif or cis element capable of binding NFE as set forth in FIG. 1 at residues 774–795, a sequence corresponding to an upstream motif or cis element capable of binding KTF.1-CS as set forth in FIG. 1 at residues 843–854, a sequence corresponding to an upstream motif or cis element capable of binding PRE is set forth in FIG. 1 at residues 987–1026, a sequence corresponding to an upstream motif or cis element capable of binding ETF-EGFR as set forth in FIG. 1 at residues 1373–1388, a sequence corresponding to an upstream motif or cis element capable of binding SRE-cFos as set forth in FIG. 1 at residues 1447–1456, a sequence corresponding to an upstream motif or cis element capable of binding Alu as set forth in FIG. 1 at residues 1331–1550, a sequence corresponding to an upstream motif or cis element capable of binding VBP as set forth in FIG. 1 at residues 1786- 1797, a sequence corresponding to an upstream motif or cis element capable of binding Malt-CS as set forth in FIG. 1 at residues 1832–1841, sequences corresponding to an upstream motif or cis element capable of binding ERE as set forth in FIG. 1 at residues 2167–2195, 3413–3429, and 3892–3896, respectively, a sequence corresponding to an upstream motif or cis element capable of binding NF-mutagen as set forth in FIG. 1 at residues 2329–2338, a sequence corresponding to an upstream motif or cis element capable of binding myc-PRF as set forth in FIG. 1 at residues 2403–2416, sequences corresponding to an upstream motif or cis element capable of binding AP2 as set forth in FIG. 1 at residues 2520–2535 and 5170–5187, respectively, sequences corresponding to an upstream motif or cis element capable of binding HSTF as set forth in FIG. 1 at residues 2622–2635, and 5105–5132, respectively, a sequence corresponding to an upstream motif or cis element characteristic of SBF as set forth in FIG. 1 at residues 2733–2743, sequences corresponding to an upstream motif or cis element capable of binding NF-1 as set forth in FIG. 1 at residues 2923–2938, 4144–4157, and 4887–4900, respectively, a sequence corresponding to an upstream motif or cis element capable of binding NF-MHCIIA/B as set forth in FIG. 1 at residues 2936–2944, a sequence corresponding to an upstream motif or cis element capable of binding PEAl as set forth in FIG. 1 at residues 3285–3298, a sequence corresponding to an upstream motif or cis element capable of binding ICS as set forth in FIG. 1 at residues 3688–3699, a sequence corresponding to an upstream motif or cis element capable of binding ISGF2 as set forth in FIG. 1 at residues 4170–4179, a sequence corresponding to an upstream motif or cis element capable of binding zinc as set forth in FIG. 1 at residues 4285–4293, a sequence corresponding to an upstream motif or cis element characteristic of CAP/CRP-galO as set forth in FIG. 1 at residues 4379–4404, sequences corresponding to an upstream motif or cis element capable of binding AP1 as set forth in FIG. 1 at residues 4428–4434, and 4627–4639, respectively, a sequence corresponding to an upstream motif or cis element capable of binding SRY as set forth in FIG. 1 at residues 4625–4634, a sequence corresponding to an upstream motif or cis element characteristic of GC2 as set forth in FIG. 1 at residues 4678–4711, a sequence corresponding to an upstream motif or cis element capable of binding PEA3 as set forth in FIG. 1 at residues 4765–4769, a sequence corresponding to an upstream motif or cis element capable of MIR as set forth in FIG. 1 at residues 4759–4954, a sequence corresponding to an upstream motif or cis element capable of binding NF-HNF-1 as set forth in FIG. 1 at residues 4923–4941, a sequence corresponding to a thyroid receptor upstream motif or cis element as set forth in FIG. 1 at residues 5151–5156, and a sequence corresponding to an upstream motif or cis element capable of binding NFκB as set forth in FIG. 1 at residues 5166–5175 (or a subsequence thereof) may be employed as a marker nucleic acid molecule to identify such polymorphism(s).

Alternatively, such polymorphisms can be detected through the use of a marker nucleic acid molecule or a marker protein that is genetically linked to (i.e., a polynucleotide that co-segregates with) such polymorphism(s). As stated above, the TIGR gene and/or a sequence or sequences that specifically hybridize to the TIGR gene have been mapped to chromosome 1q, 21–32, and more preferably to the TIGR gene located at chromosome 1, q21–27, and more preferably to the TIGR gene located at chromosome 1, q22–26, and most preferably to the TIGR gene located at chromosome 1, q24. In a preferred aspect of this embodiment, such marker nucleic acid molecules will have the nucleotide sequence of a polynucleotide that is closely genetically linked to such polymorphism(s) (e.g., markers located at chromosome 1, q19–25 (and more preferably chromosome 1, q23–25, and most preferably chromosome 1, q24.

Localization studies using a Stanford G3 radiation hybrid panel mapped the TIGR gene with the D1S2536 marker nucleic acid molecules at the D1S2536 locus with a LOD score of 6.0. Other marker nucleic acid molecules in this region include: D1S210; D1S1552; D1S2536; D1S2790; SHGC-12820; and D1S2558. Other polynucleotide markers that map to such locations are known and can be employed to identify such polymorphism(s).

The genomes of animals and plants naturally undergo spontaneous mutation in the course of their continuing evolution (Gusella, J. F., Ann. Rev. Biochem. 55:831–854 (1986)). A "polymorphism" in the TIGR gene or its flanking regions is a variation or difference in the sequence of the TIGR gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e. the original "allele") whereas other members may have the variant sequence (i.e. the variant "allele"). In the simplest case, only one variant sequence may exist, and the polymorphism is thus said to be di-allelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity and paternity analysis (Weber, J. L., U.S. Pat. No. 5,075,217; Armour, J. A. L. et al., *FEBS Lett*. 307:113–115 (1992); Jones, L. et al., *Eur. J. Haematol*. 39:144–147 (1987); Horn, G. T. et al., PCT Application WO91/14003; Jeffreys, A. J., European Patent Application 370,719; Jeffreys, A. J., U.S. Pat. No. 5,175,082); Jeffreys. A. J. et al., *Amer. J. Hum. Genet*. 39:11–24 (1986); Jeffreys. A. J. et al., *Nature* 316:76–79 (1985); Gray, I. C. et al., *Proc. R. Acad. Soc. Lond*. 243:241–253 (1991); Moore, S. S. et al., *Genomics* 10:654–660 (1991); Jeffreys, A. J. et al., *Anim. Genet*. 18:1–15 (1987); Hillel, J. et al., *Anim. Genet*. 20:145–155 (1989); Hillel, J. et al., *Genet*. 124:783–789 (1990)).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s), and more preferably within 100 kb of the polymorphism(s), and most preferably within 10 kb of the polymorphism(s) can be employed. Examples of such marker nucleic acids are set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25.

In another embodiment a marker nucleic acid will be used that is capable of specifically detecting TIGRmt1, TIGRmt2, TIGRmt3, TIGRmt4, TIGRmt5, TIGRmt11, TIGRsv1, or a combination of these mutations. Methods to detect base(s) substitutions, base(s) deletions and base(s) additions are known in the art (i.e. methods to genotype an individual). For example, "Genetic Bit Analysis ("GBA") method is disclosed by Goelet, P. et al., WO 92/15712, herein incorporated by reference, may be used for detecting the single nucleotide polymorphisms of the present invention. GBA is a method of polymorphic site interrogation in which the nucleotide sequence information surrounding the site of variation in a target DNA sequence is used to design an oligonucleotide primer that is complementary to the region immediately adjacent to, but not including, the variable nucleotide in the target DNA. The target DNA template is selected from the biological sample and hybridized to the interrogating primer. This primer is extended by a single labeled dideoxynucleotide using DNA polymerase in the presence of two, and preferably all four chain terminating nucleoside triphosphate precursors. Cohen, D. et al., (PCT Application WO91/02087) describes a related method of genotyping.

Other primer-guided nucleotide incorporation procedures for assaying polymorphic sites in DNA have been described (Komher, J. S. et al., *Nucl. Acids. Res.* 17:7779–7784 (1989), herein incorporated by reference; Sokolov, B. P., *Nucl. Acids Res.* 18:3671 (1990), herein incorporated by reference; Syv änen, A.-C., et al., *Genomics* 8:684–692 (1990), herein incorporated by reference; Kuppuswamy, M. N. et al., *Proc. Natl. Acad. Sci.* (*U.S.A.*) 88:1143–1147 (1991), herein incorporated by reference; Prezant, T. R. et al., *Hum. Mutat.* 1:159–164 (1992), herein incorporated by reference; Ugozzoli, L. et al., *GATA* 9:107–112 (1992), herein incorporated by reference; Nyrén, P. et al., *Anal. Biochem.* 208:171–175 (1993), herein incorporated by reference).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

Another preferred method of achieving such amplification employs the polymerase chain reaction ("PCR") (Mullis, K. et al., *Cold Spring Harbor Symp. Quant. Biol.* 51:263–273 (1986); Erlich H. et al., European Patent Appln. 50,424; European Patent Appln. 84,796, European Patent Application 258,017, European Patent Appln. 237,362; Mullis, K., European Patent Appln. 201,184; Mullis K. et al., U.S. Pat. No. 4,683,202; Erlich, H., U.S. Pat. No. 4,582,788; and Saiki, R. et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, F., *Proc. Natl. Acad. Sci.* (*U.S.A.*) 88:189–193 (1991). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, D., PCT Application WO 90/01069).

The "Oligonucleotide Ligation Assay" ("OLA") may alternatively be employed (Landegren, U. et al., *Science* 241:1077–1080 (1988)). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson, D. A. et al., have described a nucleic acid detection assay that combines attributes of PCR and OLA (Nickerson, D. A. et al., *Proc. Natl. Acad. Sci.* (*U.S.A.*) 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu, D. Y. et al., *Genomics* 4:560 (1989)), and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek, L. T. et al., U.S. Pat. No. 5,130,238; Davey, C. et al., European Patent Application 329,822; Schuster et al., U.S. Pat. No. 5,169,766; Miller, H. I. et al., PCT appln. WO 89/06700; Kwoh, D. et al., *Proc. Natl. Acad. Sci.* (*U.S.A.*) 86:1173 (1989); Gingeras, T. R. et al., PCT application WO 88/10315; Walker, G. T. et al., *Proc. Natl. Acad. Sci.* (*U.S.A.*) 89:392–396 (1992)). All the foregoing nucleic acid amplification methods could be used to predict or diagnose glaucoma.

The identification of a polymorphism in the TIGR gene, or flanking sequences up to about 5,000 base from either end of the coding region, can be determined in a variety of ways. By correlating the presence or absence of glaucoma in an individual with the presence or absence of a polymorphism in the TIGR gene or its flanking regions, it is possible to diagnose the predisposition (prognosis) of an asymptomatic patient to glaucoma, related diseases, or steroid sensitivity. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and animal genetic analyses (Glassberg, J., UK patent Application 2135774; Skolnick, M. H. et al., Cytogen. Cell Genet. 32:58–67 (1982); Botstein, D. et al., Ann. J. Hum. Genet. 32:314–331 (1980); Fischer, S. G et al. (PCT Application WO90/13668); Uhlen, M., PCT Application WO90/11369)). The role of TIGR in glaucoma pathogenesis indicates that the presence of genetic alterations (e.g., DNA polymorphisms) that affect the TIGR response can be employed to predict glaucoma.

A preferred method of achieving such identification employs the single-strand conformational polymorphism (SSCP) approach. The SSCP technique is a method capable of identifying most sequence variations in a single strand of DNA, typically between 150 and 250 nucleotides in length (Elles, Methods in Molecular Medicine: Molecular Diagnosis of Genetic Diseases, Humana Press (1996), herein incorporated by reference); Orita et al., *Genomics* 5:874–879 (1989), herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to Lee et al., *Anal. Biochem.* 205:289–293 (1992), herein incorporated by reference; Suzuki et al., *Anal. Biochem.* 192:82–84 (1991), herein incorporated by reference; Lo et al., *Nucleic Acids Research* 20:1005–1009 (1992), herein incorporated by reference; Sarkar et al., *Genomics* 13:441–443 (1992), herein incorporated by reference).

In accordance with this embodiment of the invention, a sample DNA is obtained from a patient. In a preferred embodiment, the DNA sample is obtained from the patient's blood. However, any source of DNA may be used. The DNA is subjected to restriction endonuclease digestion. TIGR is used as a probe in accordance with the above-described RFLP methods. By comparing the RFLP pattern of the TIGR gene obtained from normal and glaucomatous patients, one can determine a patient's predisposition (prognosis) to glaucoma. The polymorphism obtained in this approach can then be cloned to identify the mutation at the coding region which alters the protein's structure or regulatory region of the gene which affects its expression level. Changes involving promoter interactions with other regulatory proteins can be identified by, for example, gel shift assays using HTM cell extracts, fluid from the anterior chamber of the eye, serum, etc. Interactions of TIGR protein in glaucomatous cell extracts, fluid from the anterior chamber of the eye, serum, etc. can be compared to control samples to thereby identify changes in those properties of TIGR that relate to the pathogenesis of glaucoma. Similarly such extracts and fluids as well as others (blood, etc.) can be used to diagnosis or predict steroid sensitivity.

Several different classes of polymorphisms may be identified through such methods. Examples of such classes include: (1) polymorphisms present in the TIGR cDNA of different individuals; (2) polymorphisms in non-translated TIGR gene sequences, including the promoter or other regulatory regions of the TIGR gene; (3) polymorphisms in genes whose products interact with TIGR regulatory sequences; (4) polymorphisms in gene sequences whose products interact with the TIGR protein, or to which the TIGR protein binds.

In an alternate sub-embodiment, the evaluation is conducted using oligonucleotide "probes" whose sequence is complementary to that of a portion of SEQ ID NO: 1, SEQ ID NO: 2 SEQ ID NO: 3, SEQ ID NO: 4, or SEQ ID NO: 5. Such molecules are then incubated with cell extracts of a patient under conditions sufficient to permit nucleic acid hybridization.

In one sub-embodiment of this aspect of the present invention, one can diagnose or predict glaucoma, related diseases and steroid sensitivity by ascertaining the TIGR response in a biopsy (or a macrophage or other blood cell sample), or other cell sample, or more preferably, in a sample of bodily fluid (especially, blood, serum, plasma, tears, buccal cavity, etc.). Since the TIGR gene is induced in response to the presence of glucocorticoids, a highly preferred embodiment of this method comprises ascertaining such TIGR response prior to, during and/or subsequent to, the administration of a glucocorticoid. Thus, by way of illustration, glaucoma could be diagnosed or predicted by determining whether the administration of a glucocorticoid (administered topically, intraocularly, intramuscularly, systemically, or otherwise) alters the TIGR response of a particular individual, relative to that of normal individuals. Most preferably, for this purpose, at least a "TIGR gene-inducing amount" of the glucocorticoid will be provided. As used herein, a TIGR gene-inducing amount of a glucocorticoid is an amount of glucocorticoid sufficient to cause a detectable induction of TIGR expression in cells of glaucomatous or non-glaucomatous individuals.

Generating Cells, Vectors, and Expressed Proteins Using Agents of the Invention

The present invention also relates to methods for obtaining a recombinant host cell, especially a mammalian host cell, comprising introducing into a host cell exogenous genetic material comprising a nucleic acid of the invention. The present invention also relates to an insect cell comprising a recombinant vector having a nucleic acid of the invention. The present invention also relates to methods for obtaining a recombinant host cell, comprising introducing exogenous genetic material comprising a nucleic acid of the invention via homologous recombination. Through homologous recombination, the promoter and 5' flanking sequences of the TIGR gene described here can be used in gene activation methods to produce a desired gene product in host cells (see, for example, U.S. Pat. No. 5,733,746, specifically incorporated herein by reference). The specific expression of the TIGR gene in TM cells afforded by the TIGR promoter region DNA can, thus, be transferred via homologous recombination to express other gene products in a similar fashion. Some of these other gene products may be therapeutic proteins that address diseases related to increased IOP or glaucoma. Methods for selecting and using the promoter and 5' flanking sequence for the gene targeting technique involved in the gene activation method are known in the art. Depending upon the nature of the modification and associated targeting construct, various techniques may be employed for identifying targeted integration. Conveniently, the DNA may be digested with one or more restriction enzymes and the fragments probed with an appropriate DNA fragment, which will identify the properly sized restriction fragment associated with integration.

The sequence to be integrated into the host may be introduced by any convenient means, which includes calcium precipitated DNA, spheroplast fusion, transformation, electroporation, biolistics, lipofection, microinjection, or other convenient means. Where an amplifiable gene is being employed, the amplifiable gene may serve as the selection marker for selecting hosts into which the amplifiable gene has been introduced. Alternatively, one may include with the amplifiable gene another marker, such as a drug resistance marker, e.g. neomycin resistance (G418 in mammalian cells), hygromycin resistance etc., or an auxotrophy marker (HIS3, TRP1, LEU2, URA3, ADE2, LYS2, etc.) for use in yeast cells.

For example, homologous recombination constructs can be prepared where the amplifiable gene will be flanked, normally on both sides, with DNA homologous with the DNA of the target region, here the TIGR sequences. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. The homologous DNA may include the 5'-upstream region outside of the transcriptional regulatory region or enhancer sequences, transcriptional initiation sequences, adjacent sequences, or the like. The homologous region may include a portion of the coding region, where the coding region may be comprised only of an open reading frame or of combination of exons and introns. The homologous region may also comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., *E. coli*, and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary host.

DNA comprising a nucleic acid of the invention can be introduced into a host cell by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming cells are well known (see Keown et al., *Methods Enzymol.* (1989), Keown et al., *Methods Enzymol.* 185:527–537 (1990); Mansour et al., *Nature* 336:348–352, (1988); all of which are herein incorporated by reference in their entirety).

In a preferred aspect, the invention relates to recombinant insect vectors and insect cells comprising a nucleic acid of the invention. In a particularly preferred aspect, a Baculovirus expression vector is used, introduced into an insect cell, and recombinant TIGR protein expressed. The recombinant TIGR protein may be the full length protein from human TM endothelial cells, a fusion protein comprising a substantial fragment of the full length protein, for example, at least about 20 contiguous amino acids to about 100 contiguous amino acids of the full length protein, or a variant TIGR protein or fusion protein produced by site-directed mutagenesis, DNA shuffling, or a similar technique. Generally, the variant TIGR proteins and the fusion proteins will retain at least one structural or functional characteristic of the full length TIGR protein, such as the ability to bind the same antibody, the presence of the substantially similar leucine zipper region, or the ability to bind the same ligand or receptor on TM cells (see Nguyen et al., *J. Biol. Chem.* 273:6341–6350 (1998), specifically incorporated herein by reference). Nucleic acids comprising the leucine zipper-encoding regions of the TIGR gene can be identified by methods known in the art and can be used in combination with recombinant or synthetic methods to create ligand-receptor assays.

Examples of the preferred, recombinant insect vector, host cell, and TIGR protein of the invention were generated by ligating TIGR cDNA into the PVL1393 vector [Invitrogen]. This vector was transferred into Sf9 cells, the TIGR protein expressed and then purified (see U.S. Pat. No. 5,789,169 and Nguyen et al., *J. Biol. Chem.* 273:6341–6350 (1998), both of which are specifically incorporated herein by reference in their entirety). An SDS-PAGE gel of the resulting proteins showed protein bands in the 55 kDa range, which were sequenced to confirm correct identity.

In preferred embodiments of the vectors, cells and related methods of the invention, a TIGR fusion protein with GFP (green fluorescent protein) can be expressed in a TM cell line (see Nguyen, et al., *J. Biol. Chem.* 273:6341–6350 (1998) and the references cited therein for primary TM cell culture and transfection methods). Transformed, cultured TM cells at log phase were transfected with a TIGR-GFP fusion protein-encoding vector. The vector includes the CMV promoter to allow high expression, TIGR cDNA from the first ATG to the end of the protein-encoding region, a fluorescent protein tag (GFP) fused to the carboxy terminus of the TIGR-encoding sequence, and the G418 resistance gene. These elements, and their use, is known in the art or provided by this disclosure and its incorporated references. The construct is termed TIGR1-GFP. The transfection was performed using calcium phosphate or Lipofectin techniques, as known in the art. Incubation at growth condition of 37° C., 8% $CO_2$, for 6–18 hours followed. After the transfection, the DNA media was replaced by fresh growth media including G418, which was changed twice weekly, until resistant colonies of cells outgrew the monolayer cells (about 10–15 days). The cell colonies were collected and propagated several passes to select for resistant, transformed cells. The expression of fluorescent TIGR-GFP fusion protein was tested for after several passes. One out of twenty selected colonies expressed high levels of the TIGR-GFP fusion protein.

In other preferred embodiments of the cells and methods of the invention, a transformed, immortalized TM cell line can be prepared using an SV40-derived vector. Primary cultured TM cells are transfected with an SV40 vector with a defect in the PsvOri, as known in the art. Briefly, primary cultured cells at log phase are transfected with PsvOri DNA using calcium phosphate or Lipofectin and incubated at growth condition of 37° C., 8% $CO_2$ for 6–18 hours. The DNA media was replaced by fresh growth media and changed twice weekly until colonies of immortalized cells outgrow the dying monolayer (about 10–15 days). The cell colonies are collected and propagated several passes to select for transformed cells.

III. Methods of Administration

Some of the agents of the present invention can be formulated according to known methods to prepare pharmacologically acceptable compositions, whereby these materials, or their functional derivatives, having the desired degree of purity are combined in admixture with a physiologically acceptable carrier, excipient, or stabilizer. Such materials are non-toxic to recipients at the dosages and concentrations employed. The active component of such compositions may be agents, analogs or mimetics of such molecules. Where nucleic acid molecules are employed, such molecules may be sense, antisense or triplex oligonucleotides of the TIGR promoter, TIGR cDNA, TIGR intron, TIGR exon or TIGR gene.

A composition is said to be "pharmacologically acceptable" if its administration can be tolerated by a recipient patient. An agent is physiologically significant if its presence results in a detectable change in the physiology of a recipient patient.

Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the TIGR molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable articles. For preparing sustained-release compositions, the TIGR molecule(s) of the composition is preferably incorporated into a biodegradable matrix or microcapsule. A suitable material for this purpose is a polylactide, although other polymers of poly-(a-hydroxycarboxylic acids), such as poly-D-(−)-3-hydroxybutyric acid (EP 133,988A), can be used. Other biodegradable polymers include poly(lactones), poly (orthoesters), polyamino acids, hydrogels, or poly (orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al., *Chem. Tech.* 12:98 (1982).

Alternatively, instead of incorporating the TIGR molecule (s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art, see, for example, Chicz, R. M. et al. (PCT Application WO 94/04557), Jaysena, S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

Having now generally described the invention, the same will be more readily understood through reference to the following examples which are provided by way of illustration, and are not intended to be limiting of the present invention, unless specified.

EXAMPLE 1

Illustrative Single Strand Conformational Polymorphism Assay

Single strand conformational polymorphism (SSCP) screening is carried out according to the procedure of Hue et al., *The Journal of Investigative Ophthalmology* 105.4:529–632 (1995), herein incorporated by reference. SSCP primers are constructed corresponding to sequences found within the TIGR promoter and two of exons of TIGR. The following primers are constructed: forward primer "Sk-1a": 5'-TGA GGC TTC CTC TGG AAA C-3' (SEQ ID NO: 6); reverse primer "ca2": 5'-TGA AAT CAG CAC ACC AGT AG-3' (SEQ ID NO: 7); forward primer "CA2": 5'-GCA CCC ATA CCC CAA TAA TAG-3' (SEQ ID NO: 8); reverse primer "Pr+1": 5'-AGA GTT CCC CAG ATT TCA CC-3' (SEQ ID NO: 9); forward primer "Pr−1": 5'-ATC TGG GGA ACT CTT CTC AG-3' (SEQ ID NO: 10); reverse primer "Pr+2(4A2)": 5'-TAC AGT TGT TGC AGA TAC G-3' (SEQ ID NO: 11); forward primer "Pr−2(4A)": 5'-ACA ACG TAT CTG CAA CAA CTG-3' (SEQ ID NO: 12); reverse primer "Pr+3(4A)": 5'-TCA GGC TTA ACT GCA GAA CC-3' (SEQ ID NO: 13); forward primer "Pr−3(4A)": 5'-TTG GTT CTG CAG TTA AGC C-3' (SEQ ID NO: 14); reverse primer "Pr+2(4A1)": 5'-AGC AGC ACA AGG GCA ATC C-3' (SEQ ID NO: 15); reverse primer "Pr+1(4A)":

5'-ACA GGG CTA TAT TGT GGG-3' (SEQ ID NO: 16); forward primer "KS1X": 5'-CCT GAG ATG CCA GCT GTC C-3' (SEQ ID NO: 17); reverse primer "SK1XX": 5'-CTG AAG CAT TAG AAG CCA AC-3' (SEQ ID NO: 18); forward primer "KS2a1": 5'-ACC TTG GAC CAG GCT GCC AG-3' (SEQ ID NO: 19); reverse primer "SK3"5'-AGG TTT GTT CGA GTT CCA G-3' (SEQ ID NO: 20); forward primer "KS4": 5'-ACA ATT ACT GGC AAG TAT GG-3' (SEQ ID NO: 21); reverse primer "SK6A": 5'-CCT TCT CAG CCT TGC TAC C-3' (SEQ ID NO: 22); forward primer "KS5": 5'-ACA CCT CAG CAG ATG CTA CC-3' (SEQ ID NO: 23); reverse primer "SK8": 5'-ATG GAT GAC TGA CAT GGC C-3' (SEQ ID NO: 24); forward primer "KS6": 5'-AAG GAT GAA CAT GGT CAC C-3' (SEQ ID NO: 25).

The locations of primers: Sk-1a, ca2, CA2, Pr+1, Pr−1, Pr+2(4A2), Pr−2(4A), Pr+3(4A), Pr−3 (4A), Pr−3(4A), Pr+2(4A1), and Pr+1(4A) are diagramatically set forth in FIG. 4. The location of primers: KS1X, SK1XX, Ks2a1, SK3, KS4, SK6A, KS5, SK8, and KS6 are diagramatically set forth in FIG. 5.

Families with a history of POAG in Klamath Falls, Ore., are screened by SSCP according to the method of Hue et al., *The Journal of Investigative Ophthalmology* 105.4:529–632 (1995), herein incorporated by reference). SSCP primers SK-1a, ca2, CA2, Pr+1, Pr-2(4A), Pr+3(4A), SK1XX, and KS6 detect single strand conformational polymorphisms in this population. An SSCP is detected using SSCP primers Pr+3(4A) and Pr−2(4A). 70 family members of the Klamath Fall, Oregon are screened with these primers and the results are set forth in Table 1.

TABLE 1

| | Total | SSCP+ | SSCP− |
|---|---|---|---|
| Glaucoma positive individuals[1] | 12 | 12 | 0 |
| Glaucoma negative individuals | 13 | 0 | 13 |
| Spouses (glaucoma negative) | 16 | 2 | 14 |
| Others[2] | 29 | 6 | 23 |

1 = glaucoma positive individuals as determined by IOP of greater than 25 mmHg
2 = unidentified glaucoma due to the age of the individual.

A second SSCP is detected using SSCP primers Pr+1 and CA2.14 family members of the Klamath Fall, Oreg. are screened with these primers. A characteristic polymorphism is found in the 6 affected family members but absent in the 8 unaffected members. A third SSCP is detected using SSCP primers ca2 and sk-1a. The same 14 family members of the Klamath Fall, Oregon that are screened with Pr+1 and CA2 are screened with ca2 and sk-1a primers. A characteristic polymorphism is found in the 6 affected family members but absent in the 8 unaffected members. A fourth SSCP is detected using SSCP primers KS6 and SK1XX. 22 family members of the Klamath Fall, Oreg. and 10 members of a Portland, Oreg. pedigree are screened with these primers. A polymorphism is found in exon 3. The results are as set forth in Table 2.

TABLE 2

| | Total | SSCP+ | SSCP− |
|---|---|---|---|
| Klamath Fall, Oregon | | | |
| Glaucoma positive individuals[1] | 3 | 3 | 0 |
| Glaucoma negative individuals | 6 | 0 | 6 |
| Others[2] | 13 | 6 | 7 |
| Portland, Oregon | | | |
| Glaucoma positive individuals[1] | 6 | 6 | 0 |
| Glaucoma negative individuals | 4 | 0 | 4 |
| Others[2] | 0 | 0 | 0 |

1 = glaucoma positive individuals as determined by IOP of greater than 25 mmHg
2 = unidentified glaucoma due to the age of the individual.

EXAMPLE 2

TIGR Homologies

A novel "myosin-like" acidic protein termed myocilin is expressed predominantly in the photoreceptor cells of retina and is localized particularly in the rootlet and basal body of connecting cilium (Kubota et al., Genomics 41:360–369 (1997), herein incorporated by reference). The myocilin gene is mapped to human chromosome 1q23–q24. The coding region of myocilin is 100 percent homologous with TIGR.

Homology searches are performed by GCG (Genetics Computer Group, Madison, Wis.) and include the GenBank, EMBL, Swiss-Prot databases and EST analysis. Using the Blast search, the best fits are found with a stretch of 177 amino acids in the carboxy terminals for an extracellular mucus protein of the olfactory, olfactomedin and three olfactomedin-like species. The alignment presented in FIG. 6 shows the TIGR homology (SEQ ID NO. 27) to an expressed sequence tag (EST) sequence from human brain (ym08h12.r1)(SEQ ID NO. 28)(The WashU-Merck EST Project, 1995); the Z domain of olfactomedin-related glycoprotein from rat brain (1B426bAMZ)(SEQ ID NO. 29) (Danielson et al., *Journal of Neuroscience Research* 38: 468–478 (1994), herein incorporated by reference) and the olfactomedin from olfactory tissue of bullfrogs (ranofm) (SEQ ID NO. 30)(Yokoe and Anholt, *Proc. Natl. Acad. Sci.* 90:4655–4659 (1993), herein incorporated by reference; Snyder and Anholt, *Biochemistry* 30:9143–9153 (1991), herein incorporated by reference). These domains share very similar amino acid positions as depicted in the consensus homology of FIG. 6 (SEQ ID NO. 31), with the exception being the truncated human clone in which the position with respect to its full length sequence has not been established. No significant homology is found for the amino termini of these molecules.

EXAMPLE 3

Identification of TIGRmt11

DNA samples were obtained from individuals noted for having elevated IOP in response to the administration of topical corticosteroids. Typically, the "Armaly" criteria is used to register IOP changes.

Genomic DNA from blood or buccal swabs were used for PCR amplification. The PCR reaction includes 95° C. for 30 sec, for denaturation, 55° C. for 30 sec, for annealing and 72° C. for 30 sec for synthosis. The reaction was performed for 30 cycles with an additional cycle of 72° C. for 5 min at the end.

The primer pair for the PCR reaction can include any pair that amplifies a specific region targeted for analyzing mutants or polymorphisms. Preferably, the amplified region will be from about 500 base pairs 5' of the start of transcription to the start of translation. More preferably, it will include an amplified region about 200 bp 5' of the start of transcription to about 10 base pairs 5' to the start of translation. Methods for determining amplification primer sequences from within a known sequence region are well known in the art. Examplary methods include, but are not limited to, computer generated searches using programs such as Primer3 (www-genome.wi.mit.edu/cgi-bin/primer/primer3.cgi), STSPipeline (www-genome.wi.mit.edu/cgi-bin/www-STS_Pipeline), or GeneUp (Pesole, et al., *Bio-Techniques* 25:112–123 (1998)).

In an especially preferred embodiment, this amplified region will be from position 5044 of SEQ ID NO: 3 to about 5327 of SEQ ID NO: 3, which will thus employ primers of the sequence of about 5044 to about 5066 and the sequence of about 5309 to about 5327 of SEQ ID NO: 3, or the complement. In one embodiment, the complement of the sequence from about 5309 to about 5327 is used as one of the primers and the sequence from about 5044 to about 5066 is used as the other primer.

For this example, the following primers were used: forward primer CA-2R (SEQ ID NO: 35—5' AACTATTATT GGGGTATGGG) and reverse primer Sk-1a (SEQ ID NO: 36—5' TTGGTGAGGC TTCCTCTGC). The primers were labeled with a fluorescent dye IRD-800 by Li-Cor Technology and the PCR product (about 300 bp) was denatured by heat and subject to BESS assays to detect mutations.

BESS, or Base Excision Sequence Scanning, employed specific restriction enzyme that cleaves T position of single strand DNA. The cleavage will produce DNA fragments that could be observed by acrylamide gels. Based on this, a 'T mutation' will produce different cleavage pattern for the mutated strand compared to the normal strand. Since 95% of mutations involve a T mutation, this method is very practical. In addition to BESS, the amplified fragments can also be sequenced or compared by hybridization methods (microarray hybridization techniques or the sequencing-by-hybridization technique) in order to determine the exact nucleotide sequence, as known in the art.

Using this assay, patients exhibiting an increased IOP in response to topical corticosteroid treatments had an elevated level of a T mutation in one particular position, at about 160 bases 5' to the start of the TIGR coding region. The presence of this particular mutation, called TIGRmt11, therefore, indicated a specific genetic linkage to steroid sentivity that manifests in at least a higher risk of increased IOP, and thus glaucoma, in response to steroid treatment.

TABLE 3

| Subject | Duration of CS Treatment | IOP (OD/OS) | Genotype (mt.11) |
|---|---|---|---|
| 1 | 1 year | 38/30 | +/− |
| 2 | 3 weeks | 25/28 | +/+ |
| 3 | 2 weeks | 28/28 | +/+ |

CS = corticosteroid, topical treatment (1 year) CS treatment 38/30 mm Hg, OD/OS; (3 weeks) CS treatment 25/28 mm Hg, OD/OS; (2 weeks) CS treatment 28/38 mm Hg, OD/OS The sequence in SEQ ID NO: 33 (CAAACAGACT TC CGGAAGGT) identifies bases immediately adjacent to the single base polymorphism, which represents bases 5101 to 5120 of SEQ ID NO: 1, except that the underlined C in the TIGRmt11 sequence variant is substituted for the 'wild type' T, found in SEQ ID NO: 1.

EXAMPLE 4

Verification of Linkage Between TIGRmt11 and Risk of Glaucoma

Subjects are given standard topical dexamethasone eye drops (0.1%) four times a day, for four weeks. Pre-treatment and post-treatment IOP readings are taken and patients are classified as having high (>16 mmHg), intermediate (6–16 mmHg) or low (<6 mmHg) IOP responses under the "Armaly" criteria. DNA samples are obtained from four subjects having high or intermediate IOP changes. Samples from several non-responder patients were also taken. The DNA samples were analyzed for the presence of the TIGRmt11 variant sequence, as discussed above. The results are given in Table 4.

TABLE 4

| Subject | Age | Classification | CS-IOP Response | Genotype (mt.11) |
|---|---|---|---|---|
| 1 | 47 | OHT | Intermediate | +/+ |
| 2 | 28 | POAG | High | +/+ |
| 3 | 46 | POAG/OHT | High | +/+ |
| 4 | 15 | Stevens-Johnson | High | +/+ |
| 5 | Nr | Normal | Low | −/− |
| 6 | Nr | Normal | Low | −/− |
| 7 | Nr | Normal | Low | −/− |

OHT = Ocular Hypertensive (began with a mild IOP elevation, no POAG)
POAG = Original diagnosis is primary open-angle glaucoma
POAG/OHT = Converted to POAG, from original diagnosis OHT The data obtained indicates the association of TIGRmt.11 and the response to topical CS. Clearly, all the subjects with clinically identifiable responses to the CS treatment possessed the TIGRmt11 variant sequence while none of the subjects with the 'wild type'sequence, or a sequence that did not possess the TIGRmt11 variant, did not.

While the invention has been described in connection with specific embodiments thereof, it understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

EXAMPLE 5

TIGR 5' Region/Promoter Activity Assays and Methods for Detecting Cell Components Binding to TIGR Gene Sequences The 283 base 5' fragment of the TIGR 5' region (SEQ ID NO: 37) is amplified from genomic DNA of a normal human subject as discusssed in Example 3. The DNA is cloned into a pSEAP vector (Clontech, Calif.) so that transcription was under the control of the TIGR sequences. More specifically, pSEAP2-enhancer vector is digested with Srfl to produce a blunt end. The 283 bp fragment is blunt end ligated to the vector using T4 ligase for 2 hours. The vector is transfected into DH5 cells to establish a plasmid clone, TMRE-1/pSEAP. PCR sequencing is used to verify the clone sequence as correct. Similarly, the equivalent genomic fragment amplified from a steroid responder sample, identified as mutant TIGR.mt11, is cloned in pSEAP2-enhancer and called clone TIGR.mt11/pSEAP.

HTM cells, Cos cells (COS-7), and HeLa cells (HeLa 229) are seeded at $10^6$ cells per well and incubated with 1 ug of the plasmid DNA to transfect using Lipofectin reagent (GIBCO, Life Technologies, Md.). Some samples of cells were also treated with dexamethasone (DEX). Then, 24, 48, and 72 hours after transfection, AP activity was measured. Cells are collected using a buffer containing L-homoarginine and the chemiluminescent substrate CSPD and a chemiluminescent enhancer added to the samples. The expression levels are then recorded using a luminometer or by brief exposure to X-ray film. The results show that AP activity is present in HTM transfected cells within 24 hours and that the levels increase over 50 fold 48 and 72 hours after transfection. In contrast, HeLa and Cos cells show insignificant AP activity at the same time points.

Figure 9:
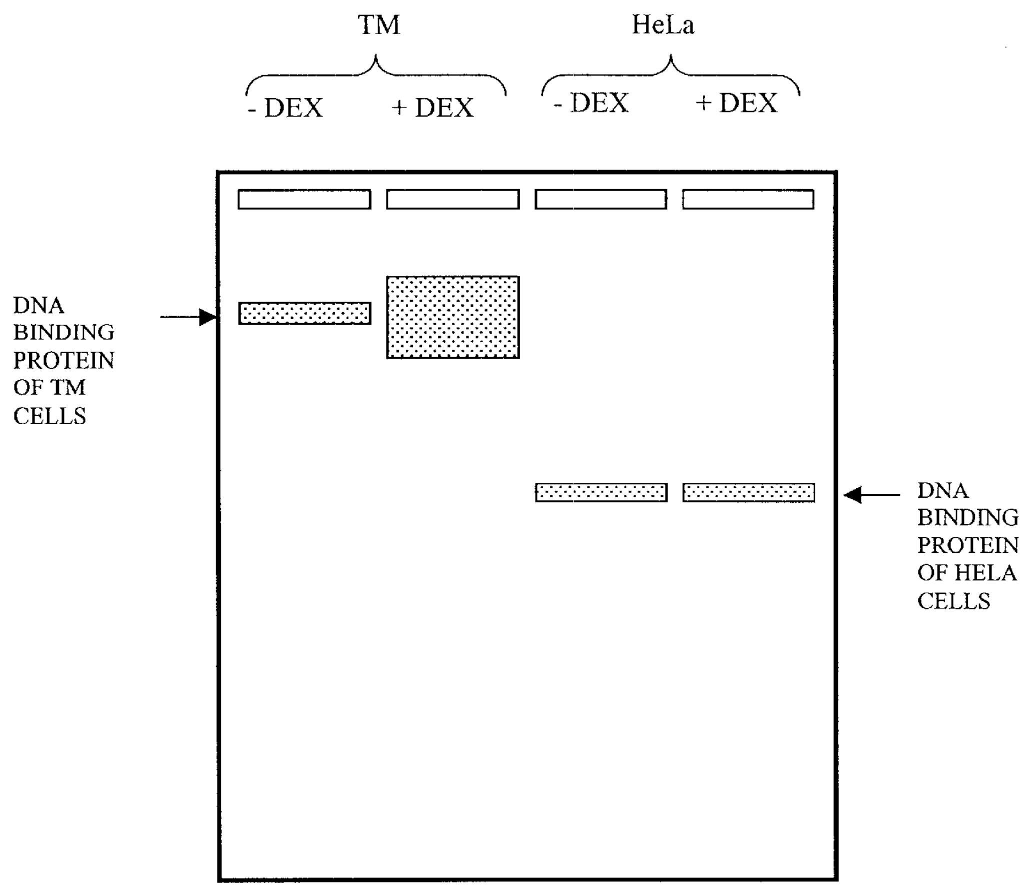
FIG. 9 shows a diagrammatic representation of the results of a gel shift assay. Lanes labeled "TM" represent the binding of cellular components from human trabecular meshwork cells to the 283 base pair TIGR 5' regulatory region. Lanes labeled "HeLa" represent the binding of cellular components from HeLa cells to the same nucleic acid. A much higher amount of cellular component binds in the +DEX (dexamethasone) treated TM cells than in the DEX TM cells (no dexamethasone).

To detect cell components that specifically bind to TIGR sequences, the amplified genomic fragments are suitably labeled, such as by end-labeling with $^{32}$PdATP using T4 Kinase. Labeled fragments are then incubated with nuclear extracts of TM cells, +/−treatment with DEX (500 nM) for 10 days, and HeLa cell extract (Stratagene, Calif.) for 15 minutes at 0° C. The samples are then run on a low ionic strength, non-denaturing polyacrylamide gel. The gel is then dried and exposed to X-ray film overnight. The shift in mobility, apparent in FIG. 9, demonstrates the presence of DNA binding components from HTM cells, and that treatment with DEX changes the amount or strength of binding.

What is claimed is:

1. A method for detecting the specific binding of a molecule to a nucleic acid comprising:

providing said nucleic acid, wherein said nucleic acid comprises the nucleotide sequence of SEQ ID NO: 3, and wherein the nucleotide sequence comprises a functional regulatory region;

contacting said nucleic acid with a sample containing said molecule to be tested; and identifying binding of said molecule to said nucleic acid.

2. The method of claim 1, wherein the identifying step comprises a gel shift assay.

3. The method of claim 1, wherein the nucleic acid is labeled.

4. The method of claim 1, wherein the sample comprises a cell extract.

5. The method of claim 1, wherein the sample comprises a single compound.

6. The method of claim 1, wherein the sample comprises more than one compound.

* * * * *

UNITED STATES PATENT AND TRADEMARK OFFICE

CERTIFICATE OF CORRECTION

PATENT NO. : 6,475,724 B1

DATED : November 5, 2002

INVENTOR(S) : Thai D. Nguyen et al.

It is certified that error appears in the above-identified patent and that said Letters Patent is hereby corrected as shown below:

Column 8,
Line 38, should read:
-- TIGRmt11 (not pictured in FIG. 2) is the result of a replace- --

Signed and Sealed this

Twenty-ninth Day of July, 2003

JAMES E. ROGAN
*Director of the United States Patent and Trademark Office*